United States Patent
Erwin et al.

(10) Patent No.: US 6,846,968 B1
(45) Date of Patent: Jan. 25, 2005

(54) PRODUCTION OF LYSOSOMAL ENZYMES IN PLANTS BY TRANSIENT EXPRESSION

(75) Inventors: Robert L. Erwin, Davis, CA (US); Laurence K. Grill, Vacaville, CA (US); Gregory P. Pogue, Vacaville, CA (US); Thomas H. Turpen, Vacaville, CA (US); Monto H. Kumagai, Kailua, HI (US)

(73) Assignee: Large Scale Biology Corporation, Vacaville, CA (US)

( * ) Notice: Subject to any disclaimer, the term of this patent is extended or adjusted under 35 U.S.C. 154(b) by 21 days.

(21) Appl. No.: 09/626,127

(22) Filed: Jul. 26, 2000

Related U.S. Application Data

(63) Continuation-in-part of application No. 09/316,572, filed on May 21, 1999, now abandoned, which is a continuation of application No. 08/324,003, filed on Oct. 14, 1994, now Pat. No. 5,977,438, which is a continuation-in-part of application No. 08/176,414, filed on Dec. 29, 1993, now Pat. No. 5,811,653, which is a continuation-in-part of application No. 07/997,733, filed on Dec. 30, 1992, now abandoned, said application No. 08/324,003, is a continuation-in-part of application No. 08/184,237, filed on Jan. 19, 1994, now Pat. No. 5,589,367, which is a continuation-in-part of application No. 07/923,692, filed on Jul. 31, 1992, now Pat. No. 5,316,931, which is a continuation-in-part of application No. 07/739,143, filed on Aug. 1, 1991, now abandoned, and a continuation-in-part of application No. 07/737,899, filed on Jul. 26, 1991, now abandoned, and a continuation-in-part of application No. 07/641,617, filed on Jan. 16, 1991, now abandoned, and a continuation-in-part of application No. 07/600,244, filed on Oct. 22, 1990, now abandoned, which is a continuation of application No. 07/310,881, filed on Feb. 17, 1989, now abandoned, which is a continuation-in-part of application No. 07/160,766, filed on Feb. 26, 1988, now abandoned, and a continuation-in-part of application No. 07/160,771, filed on Feb. 26, 1988, now abandoned, said application No. 07/641,617, is a continuation of application No. 07/347,637, filed on May 5, 1989, now abandoned, which is a continuation of application No. 07/737,899, which is a continuation of application No. 07/363,138, filed on Jun. 8, 1989, now abandoned, which is a continuation-in-part of application No. 07/219,279, filed on Jul. 15, 1988, now abandoned, said application No. 07/739,143, is a continuation-in-part of application No. 07/737,899, and a continuation-in-part of application No. 07/641,617, and a continuation-in-part of application No. 07/600,244.

(51) Int. Cl.[7] .............................. A01H 1/02; A01H 1/00; C07H 21/00; C12N 15/00; C12N 15/82
(52) U.S. Cl. ...................... 800/260; 800/277; 800/278; 536/23.1; 536/24.1; 435/440; 435/468; 435/320.1; 435/419
(58) Field of Search ................................ 800/260, 277, 800/278; 536/231, 241; 435/440, 468, 320.1, 419

(56) References Cited

U.S. PATENT DOCUMENTS

| | | | |
|---|---|---|---|
| 4,956,282 A | * 9/1990 | Goodman et al. | 435/69.51 |
| 5,082,778 A |   1/1992 | Overbeek et al. | 435/172.3 |
| 5,179,023 A |   1/1993 | Calhoun et al. | 435/320.1 |
| 5,401,650 A | * 3/1995 | Desnick et al. | 435/208 |
| 5,580,757 A | * 12/1996 | Desnick et al. | 435/69.7 |
| 5,597,945 A | * 1/1997 | Jaynes et al. | 800/205 |
| 5,929,304 A |   7/1999 | Radin et al. | 800/288 |

FOREIGN PATENT DOCUMENTS

| | | |
|---|---|---|
| WO | WO 90/10076 | 9/1990 |
| WO | WO 97/10359 | 3/1997 |

OTHER PUBLICATIONS

Murray G. J., et al., "Production of Recombinant Human Glucocerebrosidase in Plants", *Fed. of American Soc. for Experimental Biology*, p. A1126, vol. 10, No. 6, Apr. 30, 1996, Journal, Fed. of American Soc. for Experimental Biology, Bethesda, Maryland.

Coppola G., et al., "Characterization of glycoylated and catalytically active recombinant human a–galactosidase A using a baculovirus vector", *Gene*, pp. 197–203, 144 (1994), Elsevier Science B.V., Netherlands.

Hondred D. and Vierstra R. D., "Novel applications of the ubiquitin–dependent proteolytic pathway in plant genetic engineering", *Current Opinion in Biotechnology*, pp. 147–151, vol. 3, (Apr. 1992), Current Biology Ltd.

Vierstra R. D., "Protein Degradation in Plants", *Annual Review of Plant Physiology and Plant Molecular Biology*, pp. 385–410, vol. 44 (1993), Annual Reviews Inc., Palo Alto, California.

Kenward K D., et al., "Accumulation of type I fish antifreeze protein in transgenic tobacco is cold–specific", *Plant Molecular Biology*, pp. 377–385, vol. 23, No. 2 (Oct. 1993), Kluwer Academic Publishers, Belgium.

Lee H. I. and Raikhel N. V., "Prohevein is poorly processed but shows enhanced resistance to a chitin–binding fungus in transgenic tomato plants", *Brazilian Journal of Medical and Biological Research*, pp. 743–750, vol. 28 (Jul. 1995).

\* cited by examiner

*Primary Examiner*—Jezia Riley
(74) *Attorney, Agent, or Firm*—Thomas Gallegos; John C. Robbins

(57) ABSTRACT

The invention relates to the production of enzymatically active recombinant human and animal lysosomal enzymes involving construction and expression of recombinant expression constructs comprising coding sequences of human or animal lysosomal enzymes in a plant expression system. The plant expression system provides for post-translational modification and processing to produce a recombinant gene product exhibiting enzymatic activity. The invention is demonstrated by working examples in which transgenic tobacco plants express recombinant expression constructs comprising human glucocerebrosidase nucleotide sequences. The invention is also demonstrated by working examples in which transfected tobacco plants express recombinant viral expression constructs comprising human α galactosidase nucleotide sequences. The recombinant lysosomal enzymes produced in accordance with the invention may be used for a variety of purposes, including but not limited to enzyme replacement therapy for the therapeutic treatment of human and animal lysosomal storage diseases.

7 Claims, 18 Drawing Sheets

Tobamovirus Vector for rGal-A Expression

Accumulation and Activity of WT and ER-Targeted rGal-A

FIG. 5
Carboxy-Modifications to rGal-A

| | -30 - 20 -10 |
|---|---|
| WT | T*SRLRSHINPTGTVLLQLENTMQMSLKDLL |
| WTR | TSRLRSHINPTGTVLLQLENTMQMSLKDLLSEKDEL |
| Δ4 | TSRLRSHINPTGTVLLQLENTMQMSL |
| Δ4R | TSRLRSHINPTGTVLLQLENTMQMSLSEKDEL |
| Δ8 | TSRLRSHINPTGTVLLQLENTM |
| Δ8R | TSRLRSHINPTGTVLLQLENTMSEKDEL |
| Δ12 | TSRLRSHINPTGTVLLQL |
| Δ12R | TSRLRSHINPTGTVLLQLSEKDEL |
| Δ25 | TSRLR |
| Δ25R | TSRLRSEKDEL |

Control virus (GFP, AMP, IFN g)

*potential CTPP cleavage (Gene 58:177,1987).

Western Blot Analysis of Carboxy-modified rGal-A

FIG. 7 Enzymatic Activity of Carboxy-Modified rGal-A

Schematic of rGal-A Secretion

FIG. 12-1

```
GTATTTTTACAACAATTACCAACAACAACAAACAACAAACAACATTACAATTACTATTTACAATTACAATGGCATACACA
CAGACAGCTACCACATCAGCTTTGCTGGACACTGTCCGAGGAAACAACTCCTTGGTCAATGATCTAGCAAAGCGTCGTCT
TTACGACACAGCGGTTGAAGAGTTTAACGCTCGTGACCGCAGGCCCAAGGTGAACTTTTCAAAAGTAATAAGCGAGGAGC
AGACGCTTATTGCTACCCGGCGTATCCAGAATTCCAAATTACATTTTATAACACGCAAAATGCCGTGCATTCGCTTGCA
GGTGGATTGCGATCTTTAGAACTGGAATATCTGATGATGCAAATTCCCTACGGATCATTGACTTATGACATAGGCGGGAA
TTTTGCATCGCATCTGTTCAAGGGACGAGCATATGTACACTGCTGTATGCCCAACCTGGACGTTCGAGACATCATGCGGC
ACGAAGGCCAGAAAGACAGTATTGAACTATACCTTTCTAGGCTAGAGAGAGGGGGGAAAACAGTCCCCAACTTCCAAAAG
GAAGCATTTGACAGATACGCAGAAATTCCTGAAGACGCTGTCGTCACAATACTTTCCAGACAATGCGACATCAGCCGAT
GCAGCAATCAGGCAGAGTGTATGCCATTGCGCTACACAGCATATATGACATACCAGCCGATGAGTTCGGGGCGGCACTCT
TGAGGAAAAATGTCCATACGTGCTATGCCGCTTTCCACTTCTCTGAGAACCTGCTTCTTGAAGATTCATACGTCAATTTG
GACGAAATCAACGCGTGTTTTTCGCGCGATGGAGACAAGTTGACCTTTTCTTTTGCATCAGAGAGTACTCTTAATTATTG
TCATAGTTATTCTAATATTCTTAAGTATGTGTGCAAAACTTACTTCCCGGCCTCTAATAGAGAGGTTTACATGAAGGAGT
TTTTAGTCACCAGAGTTAATACCTGGTTTTGTAAGTTTTCTAGAATAGATACTTTTCTTTTGTACAAAGGTGTGGCCCAT
AAAAGTGTAGATAGTGAGCAGTTTTATACTGCAATGGAAGACGCATGGCATTACAAAAAGACTCTTGCAATGTGCAACAG
CGAGAGAATCCTCCTTGAGGATTCATCATCAGTCAATTACTGGTTTCCCAAAATCAGGGATATGGTCATCGTACCATTAT
TCGACATTTCTTTGGAGACTAGTAAGAGGACGCGCAAGGAAGTCTTAGTGTCCAAGGATTTCGTGTTTACAGTGCTTAAC
CACATTCGAACATACCAGGCGAAAGCTCTTACATACGCAAATGTTTTGTCCTTTGTCGAATCGATTCGATCGAGGGTAAT
CATTAACGGTGTGACAGCGAGGTCCGAATGGGATGTGGACAAATCTTTGTTACAATCCTTGTCCATGACGTTTTACCTGC
ATACTAAGCTTGCCGTTCTAAAGGATGACTTACTGATTAGCAAGTTTAGTCTCGGTTCGAAAACGGTGTGCCAGCATGTG
TGGGATGAGATTTCGCTGGCGTTTGGGAACGCATTTCCCTCCGTGAAAGAGAGGCTCTTGAACAGGAAACTTATCAGAGT
GGCAGGCGACGCATTAGAGATCAGGGTGCCTGATCTATATGTGACCTTCCACGACAGATTAGTGACTGAGTACAAGGCCT
CTGTGGACATGCCTGCGCTTGACATTAGGAAGAAGATGGAAGAAACGGAAGTGATGTACAATGCACTTTCAGAGTTATCG
GTGTTAAGGGAGTCTGACAAATTCGATGTTGATGTTTTTTCCCAGATGTGCCAATCTTTGGAAGTTGACCCAATGACGGC
AGCGAAGGTTATAGTCGCGGTCATGAGCAATGAGAGCGGTCTGACTCTCACATTTGAACGACCTACTGAGGCGAATGTTG
CGCTAGCTTTACAGGATCAAGAGAAGGCTTCAGAAGGTGCTTGTAGTTACCTCAAGAGAAGTTGAAGAACCGTCCATG
AAGGGTTCGATGGCCAGAGGAGAGTTACAATTAGCTGGTCTTGCTGGAGATCATCCGGAGTCGTCCTATTCTAAGAACGA
GGAGATAGAGTCTTTAGAGCAGTTTCATATGGCAACGGCAGATTCGTTAATTCGTAAGCAGATGAGCTCGATTCTGTACA
CGGGTCCGATTAAAGTTCAGCAAATGAAAAACTTTATCGATAGCCTGGTAGCATCACTATCTGCTGCGGTGTCGAATCTC
GTCAAGATCCTCAAAGATACAGCTGCTATTGACCTTGAAACCCGTCAAAAGTTTGGAGTCTTGGATGTTGCATCTAGGAA
GTGGTTAATCAAACCAACGGCCAAGAGTCATGCATGGGTGTTGTTGAAACCCACGCGAGGAAGTATCATGTGGCGCTTT
TGGAATATGATGAGCAGGGTGTGGTGACATGCGATGATTGGAGAAGAGTAGCTGTCAGCTCTGAGTCTGTTGTTTATTCC
GACATGGCGAAACTCAGAACTCTGCGCAGACTGCTTCGAAACGGAGAACCGCATGTCAGTAGCGCAAAGGTTGTTCTTGT
GGACGGAGTTCCGGGCTGTGGGAAAACCAAAGAAATTCTTTCCAGGGTTAATTTTGATGAAGATCTAATTTTAGTACCTG
GCAAGCAAGCCGCGGAAATGATCAGAAGACGTGCGAATTCCTCAGGGATTATTGTGGCCACGAAGGACAACGTTAAACC
GTTGATTCTTTCATGATGAATTTTGGGAAAAGCACACGCTGTCAGTTCAAGAGGTTATTCATTGATGAAGGGTTGATGTT
GCATACTGGTTGTGTTAATTTTCTTGTGGCGATGTCATTGTGCGAAATTGCATATGTTTACGGAGACACACAGCAGATTC
CATACATCAATAGAGTTTCAGGATTCCCGTACCCCGCCCATTTTGCCAAATTGGAAGTTGACGAGGTGGAGACACGCAGA
ACTACTCTCCGTTGTCCAGCCGATGTCACACATTATCTGAACAGGAGATATGAGGGCTTTGTCATGAGCACTTCTTCGGT
TAAAAAGTCTGTTTCGCAGGAGATGGTCGGCGGAGCCGCCGTGATCAATCCGATCTCAAAACCCTTGCATGGCAAGATCC
TGACTTTTACCCAATCGGATAAAGAAGCTCTGCTTTCAAGAGGGTATTCAGATGTTCACACTGTGCATGAAGTGCAAGGC
GAGACATACTCTGATGTTTCACTAGTTAGGTTAACCCCTACACCAGTCTCCATCATTGCAGGAGACAGCCCACATGTTTT
GGTCGCATTGTCAAGGCACACCTGTTCGCTCAAGTACTACACTGTTGTTATGGATCCTTTAGTTAGTATCATTAGAGATC
TAGAGAAACTTAGCTCGTACTTGTTAGATATGTATAAGGTCGATGCAGGAACACAATAGCAATTACAGATTGACTCGGTG
TTCAAAGGTTCCAATCTTTTTGTTGCAGCGCCAAAGACTGGTGATATTTCTGATATGCAGTTTTACTATGATAAGTGTCT
CCCAGGCAACAGCACCATGATGAATAATTTTGATGCTGTTACCATGAGGTTGACTGACATTTCATTGAATGTCAAAGATT
GCATATTGGATATGTCTAAGTCTGTTGCTGCGCCTAAGGATCAAATCAAACCACTAATACCTATGGTACGAACGGCGGCA
GAAATGCCACGCCAGACTGGACTATTGGAAAATTTAGTGGCCATCATTAAAAGGAACTTTAACGCACCCGAGTTGTCTGG
CATCATTGATATTGAAAATACTGCATCTTTAGTTGTAGATAAGTTTTTTTGATAGTTATTTGCTTAAAGAAAAAAGAAAC
CAAATAAAAATGTTTCTTTGTTCAGTAGAGAGTCTCTCAATAGATGGTTAGAAAAGCAGGAACAGGTAACAATAGGCCAG
CTCGCAGATTTTGATTTTGTAGATTTGCCAGCAGTTGATCAGTACAGACACATGATTAAAGCACAACCCAAGCAAAAATT
GGACACTTCAATCCAAACGGAGTACCCGGCTTTGCAGACGATTGTGTACCATTCAAAAAAGATCAATGCAATATTTGGCC
CGTTGTTTAGTGAGCTTACTAGGCAATTACTGGACAGTGTTGATTCGAGCAGATTTTTGTTTTTCACAAGAAAGACACCA
GCGCAGATTGAGGATTTCTTCGGAGATCTCGACAGTCATGTGCCGATGGATGTCTTGGAGCTGGATATATCAAAATACGA
```

FIG. 12-2

```
CAAATCTCAGAATGAATTCCACTGTGCAGTAGAATACGAGATCTGGCGAAGATTGGGTTTTGAAGACTTCTTGGGAGAAG
TTTGGAAACAAGGGCATAGAAAGACCACCCTCAAGGATTATACCGCAGGTATAAAAACTTGCATCTGGTATCAAAGAAAG
AGCGGGGACGTCACGACCTTCATTGGAAACACTGTGATCATTGCTGCATGTTTGGCCTCGATGCTTCCGATGGAGAAAAT
AATCAAAGGAGCCTTTTGCGGTGACGATAGTCTGCTGTACTTTCCAAAGGGTTGTGAGTTTCCGGATGTGCAACACTCCG
CGAATCTTATGTGGAATTTTGAAGCAAAACTGTTTAAAAAAACAGTATGGATACTTTTGCGGAAGATATGTAATACATCAC
GACAGAGGATGCATTGTGTATTACGATCCCCTAAAGTTGATCTCGAAACTTGGTGCTAAACACATCAAGGATTGGGAACA
CTTGGAGGAGTTCAGAAGGTCTCTTTGTGATGTTGCTGTTTCGTTGAACAATTGTGCGTATTACACACAGTTGGACGACG
CTGTATCGGAGGTTCATAAGACCGCCCCTCCAGGTTCGTTTGTTTATAAAAGTCTGGTGAAGTATTTGTCTGATAAAGTT
CTTTTTAGAAGTTTGTTTATAGATGGCTCTAGTTGTTAAAGGAAAAGTGAATATCAATGAGTTTATCGACCTGACAAAAA
TGGAGAAGATCTTACCGTCGATGTTTACCCCTGTAAAGAGTGTTATGTGTTCCAAAGTTGATAAAATAATGGTTCATGAG
AATGAGTCATTGTCAGAGGTGAACCTTCTTAAAGGAGTTAAGCTTATTGATAGTGGATACGTCTGTTTAGCCGGTTTGGT
CGTCACGGGCGAGTGGAACTTGCCTGACAATTGCAGAGCAGGTGTGAGCGTGTGTCTGGTGGACAAAAGGATGGAAAGAG
CCGACGAGGCCACTCTCGGATCTTACTACACAGCAGCTGCAAAGAAAAGATTTCAGTTCAAGGTCGTTCCCAATTATGCT
ATAACCACCCAGGACGCGATGAAAAACGTCTGGCAAGTTTTAGTTAATATTAGAAATGTGAAGATGTCAGCGGGTTTCTG
TCCGCTTTCTCTGGAGTTTGTGTCGGTGTGTATTGTTTATAGAAATAATATAAAATTAGGTTTGAGAGAGAAGATTACAA
ACGTGAGAGACGGAGGGCCCATGGAACTTACAGAAGAAGTCGTTGATGAGTTCATGGAAGATGTCCCTATGTCGATCAGG
CTTGCAAAGTTTCGATCTCGAACCGGAAAAAAGAGTGATGTCCGCAAAGGGAAAAATAGTAGTAATGATCGGTCAGTGCC
GAACAAGAACTATAGAAATGTTAAGGATTTTGGAGGAATGAGTTTTAAAAAGAATAATTTAATCGATGATGATTCGGAGG
CTACTGTCGCCGAATCGGATTCGTTTTAAATAGATCTTACAGTATCACTACTCCATCTCAGTTCGTGTTCTTGTCATTAA
TATGCAGGTGCTGAACACCATGGTGAACAAACACTTCTTGTCCCTTTCGGTCCTCATCGTCCTCCTTGGCCTCTCCTCCA
ACTTGACAGCCGGCATGCTGGACAATGGATTGGCAAGGACGCCTACCATGGGCTGGCTGCACTGGGAGCGCTTCATGTGC
AACCTTGACTGCCAGGAAGAGCCAGATTCCTGCATCAGTGAGAAGCTCTTCATGGAGATGGCAGAGCTCATGGTCTCAGA
AGGCTGGAAGGATGCAGGTTATGAGTACCTCTGCATTGATGACTGTTGGATGGCTCCCCAAAGAGATTCAGAAGGCAGAC
TTCAGGCAGACCCTCAGCGCTTTCCTCATGGGATTCGCCAGCTAGCTAATTATGTTCACAGCAAAGGACTGAAGCTAGGG
ATTTATGCAGATGTTGGAAATAAAACCTGCGCAGGCTTCCCTGGGAGTTTTGGATACTACGACATTGATGCCCAGACCTT
TGCTGACTGGGGAGTAGATCTGCTAAAATTTGATGGTTGTTACTGTGACAGTTTGGAAAATTTGGCAGATGGTTATAAGC
ACATGTCCTTGGCCCTGAATAGGACTGGCAGAAGCATTGTGTACTCCTGTGAGTGGCCTCTTTATATGTGGCCCTTTCAA
AAGCCCAATTATACAGAAATCCGACAGTACTGCAATCACTGGCGAAATTTTGCTGACATTGATGATTCCTGGAAAAGTAT
AAAGAGTATCTTGGACTGGACATCTTTTAACCAGGAGAGAATTGTTGATGTTGCTGGACCAGGGGGTTGGAATGACCCAG
ATATGTTAGTGATTGGCAACTTTGGCCTCAGCTGGAATCAGCAAGTAACTCAGATGGCCCTCTGGGCTATCATGGCTGCT
CCTTTATTCATGTCTAATGACCTCCGACACATCAGCCCTCAAGCCAAAGCTCTCCTTCAGGATAAGGACGTAATTGCCAT
CAATCAGGACCCCTTGGGCAAGCAAGGGTACCAGCTTAGACAGGGAGACAACTTTGAAGTGTGGGAACGACCTCTCTCAG
GCTTAGCCTGGGCTGTAGCTATGATAAACCGGCAGGAGATTGGTGGACCTCGCTCTTATACCATCGCAGTTGCTTCCCTG
GGTAAAGGAGTGGCCTGTAATCCTGCCTGCTTCATCACACAGCTCCTCCCTGTGAAAAGGAAGCTAGGGTTCTATGAATG
GACTTCAAGGTTAAGAAGTCACATAAATCCCACAGGCACTGTTTTGCTTCAGCTAtctgaaaaggacgaattatgaCCTA
GGCTCGCAAAGTTTCGAACCAAATCCTCAAAAAGAGGTCCGAAAAATAATAATAATTTAGGTAAGGGGCGTTCAGGCGGA
AGGCCTAAACCAAAAAGTTTTGATGAAGTTGAAAAAGAGTTTGATAATTTGATTGAAGATGAAGCCGAGACGTCGGTCGC
GGATTCTGATTCGTATTAAATATGTCTTACTCAATCACTTCTCCATCGCAATTTGTGTTTTTGTCATCTGTATGGGCTGA
CCCTATAGAATTGTTAAACGTTTGTACAAATTCGTTAGGTAACCAGTTTCAAACACAGCAAGCAAGAACTACTGTTCAAC
AGCAGTTCAGCGAGGTGTGGAAACCTTTCCCTCAGAGCACCGTCAGATTTCCTGGCGATGTTTATAAGGTGTACAGGTAC
AATGCAGTTTTAGATCCTCTAATTACTGCGTTGCTGGGGGCTTTTGATACTAGGAATAGAATAATCGAAGTAGAAAACCA
GCAGAGTCCGACAACAGCTGAAACGTTAGATGCTACCCGCAGGGTAGACGACGCTACGGTTGCAATTCGGTCTGCTATAA
ATAATTTAGTTAATGAACTAGTAAGAGGTACTGGACTGTACAATCAGAATACTTTTGAAAGTATGTCTGGGTTGGTCTGG
ACCTCTGCACCTGCATCTTAAATGCATAGGTGCTGAAATATAAAGTTTGTGTTTCTAAAACACACGTGGTACGTACGATA
ACGTACAGTGTTTTCCCTCCACTTAAATCGAAGGGTAGTGTCTTGGAGCGCGCGGAGTAAACATATATGGTTCATATAT
GTCCGTAGGCACGTAAAAAAAGCGAGGGATTCGAATTCCCCCGGAACCCCCGGTTGGCGCCCAGGTACCAATTCTTGAAG
ACGAAAGGGCCTCGTGATACGCCTATTTTATAGGTTAATGTCATGATAATAATGGTTTCTTAGACGTCAGGTGGCACTT
TTCGGGGAAATGTGCGCGGAACCCCTATTTGTTTATTTTTCTAAATACATTCAAATATGTATCCGCTCATGAGACAATAA
CCCTGATAAATGCTTCAATAATATTGAAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAAAAGATGCTGAAGATCAGTTGGGTGCAC
GAGTGGGTTACATCGAACTGGATCTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTGTTGACGCCGGGCAAGAGCAACTCGGTCGCCGCATACA
CTATTCTCAGAATGACTTGGTTGAGTACTCACCAGTCACAGAAAAGCATCTTACGGATGGCATGACAGTAAGAGAATTAT
```

FIG. 12-3

```
GCAGTGCTGCCATAACCATGAGTGATAACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGGAGCTGAATGAAGCCATACCAAACGA
CGAGCGTGACACCACGATGCCTGCAGCAATGGCAACAACGTTGCGCAAACTATTAACTGGCGAACTACTTACTCTAGCTT
CCCGGCAACAATTAATAGACTGGATGGAGGCGGATAAAGTTGCAGGACCACTTCTGCGCTCGGCCCTTCCGGCTGGCTGG
TTTATTGCTGATAAATCTGGAGCCGGTGAGCGTGGGTCTCGCGGTATCATTGCAGCACTGGGCCAGATGGTAAGCCCTC
CCGTATCGTAGTTATCTACACGACGGGGAGTCAGGCAACTATGGATGAACGAAATAGACAGATCGCTGAGATAGGTGCCT
CACTGATTAAGCATTGGTAACTGTCAGACCAAGTTTACTCATATATACTTTAGATTGATTTAAAACTTCATTTTTAATTT
AAAAGGATCTAGGTGAAGATCCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTTCCGAAGGTAACTGGCTTCAGCAGAGCG
CAGATACCAAATACTGTCCTTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGGGTTGGACTCAAGACGATAGT
TACCGGATAAGGCGCAGCGGTCGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGCGGAGCCTATGGAAAAACGCCAGCAACGCGGCCTTT
TTACGGTTCCTGGCCTTTTGCTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCCAGTCAGTGAGCGAGGAAGCGGAAG
AGCGCCTGATGCGGTATTTTCTCCTTACGCATCTGTGCGGTATTTCACACCGCATATGGTGCACTCTCAGTACAATCTGC
TCTGATGCCGCATAGTTAAGCCAGTATACACTCCGCTATCGCTACGTGACTGGGTCATGGCTGCGCCCCGACACCCGCCA
ACACCCGCTGACGCGCCCTGACGGGCTTGTCTGCTCCCGGCATCCGCTTACAGACAAGCTGTGACCGTCTCCGGGAGCTG
CATGTGTCAGAGGTTTTCACCGTCATCACCGAAACGCGCGAGGCAGCTGCGGTAAAGCTCATCAGCGTGGTCGTGAAGCG
ATTCACAGATGTCTGCCTGTTCATCCGCGTCCAGCTCGTTGAGTTTCTCCAGAAGCGTTAATGTCTGGCTTCTGATAAAG
CGGGCCATGTTAAGGGCGGTTTTTTCCTGTTTGGTCACTTGATGCCTCCGTGTAAGGGGAATTTCTGTTCATGGGGGTA
ATGATACCGATGAAACGAGAGAGGATGCTCACGATACGGGTTACTGATGATGAACATGCCCGGTTACTGGAACGTTGTGA
GGGTAAACAACTGGCGGTATGGATGCGGCGGGACCAGAGAAAAATCACTCAGGGTCAATGCCAGCGCTTCGTTAATACAG
ATGTAGGTGTTCCACAGGGTAGCCAGCAGCATCCTGCGATGCAGATCCGGAACATAATGGTGCAGGGCGCTGACTTCCGC
GTTTCCAGACTTTACGAAACACGGAAACCGAAGACCATTCATGTTGTTGCTCAGGTCGCAGACGTTTTGCAGCAGCAGTC
GCTTCACGTTCGCTCGCGTATCGGTGATTCATTCTGCTAACCAGTAAGGCAACCCCGCCAGCCTAGCCGGGTCCTCAACG
ACAGGAGCACGATCATGCGCACCCGTGGCCAGGACCCAACGCTGCCCGAGATGCGCCGCGTGCGGCTGCTGGAGATGGCG
GACGCGATGGATATGTTCTGCCAAGGGTTGGTTTGCGCATTCACAGTTCTCCGCAAGAATTGATTGGCTCCAATTCTTGG
AGTGGTGAATCCGTTAGCGAGGTGCCGCCGGCTTCCATTCAGGTCGAGGTGGCCCGGCTCCATGCACCGCGACGCAACGC
GGGGAGGCAGACAAGGTATAGGGCGGCGCCTACAATCCATGCCAACCCGTTCCATGTGCTCGCCGAGGCGGCATAAATCG
CCGTGACGATCAGCGGTCCAGTGATCGAAGTTAGGCTGGTAAGAGCCGCGAGCGATCCTTGAAGCTGTCCCTGATGGTCG
TCATCTACCTGCCTGGACAGCATGGCCTGCAACGCGGGCATCCCGATGCCGCCGGAAGCGAGAAGAATCATAATGGGGAA
GGCCATCCAGCCTCGCGTCGCGAACGCCAGCAAGACGTAGCCCAGCGCGTCGGCCGCCATGCCGGCGATAATGGCCTGCT
TCTCGCCGAAACGTTTGGTGGCGGGACCAGTGACGAAGGCTTCAGCGAGGGCGTGCAAGATTCCGAATACCGCAAGCGAC
AGGCCGATCATCGTCGCGCTCCAGCGAAAGCGGTCCTCGCCGAAAATGACCCAGAGCGCTGCCGGCACCTGTCCTACGAG
TTGCATGATAAAGAAGACAGTCATAAGTGCGGCGACGATAGTCATGCCCCGCGCCCACCGCAAGGAGCTGACTGGGTTGA
AGGCTCTCAAGGGCATCGGTCGAGATTTAGGTGACACTATA
```

FIG. 13-1

```
GTATTTTTACAACAATTACCAACAACAACAAACAACAGACAACATTACAATTACTATTTACAATTACAATGGCATACACA
CAGACAGCTACCACATCAGCTTTGCTGGACACTGTCCGAGGAAACAACTCCTTGGTCAATGATCTAGCAAAGCGTCGTCT
TTACGACACAGCGGTTGAAGAGTTTAACGCTCCTGACCGCAGGCCCAAGGTGAACTTTTCAAAAGTAATAAGCGAGGAGC
AGACGCTTATTGCTACCCGGCGTATCCAGAATTCCAAATTACATTTTATAACACGCAAAATGCCGTGCATTCGCTTGCA
GGTGGATTGCGATCTTTAGAACTGGAATATCTGATGATGCAAATTCCCTACGGATCATTGACTTATGACATAGGCGGGAA
TTTTGCATCGCATCTGTTCAAGGGACGAGCATATGTACACTGCTGCATGCCCAACCTGGACGTTCGAGACATCATGCGGC
ACGAAGGCCAGAAAGACAGTATTGAACTATACCTTTCTAGGCTAGAGAGAGGGGGGAAAACAGTCCCCAACTTCCAAAAG
GAAGCATTTGACAGATACGCAGAAATTCCTGAAGACGCTGTCTGTCACAATACTTTCCAGACATGCGAACATCAGCCGAT
GCAGCAATCAGGCAGAGTGTATGCCATTGCGCTACACAGCATATATGACATACCAGCCGATGAGTTCGGGGCGGCACTCT
TGAGGAAAAATGTCCATACGTGCTATGCCGCTTTCCACTTCTCCGAGAACCTGCTTCTTGAAGATTCATGCGTCAATTTG
GACGAAATCAACGCGTGTTTTTCGCGCGATGGAGACAAGTTGACCTTTTCTTTTGCATCAGAGAGTACTCTTAATTACTG
TCATAGTTATTCTAATATTCTTAAGTATGTGTGCAAAACTTACTTCCCGGCCTCTAATAGAGAGGTTTACATGAAGGAGT
TTTTAGTCACCAGAGTTAATACCTGGTTTTGTAAGTTTTCTAGAATAGATACTTTTCTTTTGTACAAAGGTGTGGCCCAT
AAAAGTGTAGATAGTGAGCAGTTTTATACTGCAATGGAAGACGCATGGCATTACAAAAAGACTCTTGCAATGTGCAACAG
CGAGAGAATCCTCCTTGGGGATTCATCATCAGTCAATTACTGGTTTCCCAAAATGAGGGATATGGTCATCGTACCATTAT
TCGACATTTCTTTGGAGACTAGTAAGAGGACGCGCAAGGAACTCTTAGTGTCCAAGGATTTCGTGTTCACAGTGCTTAAC
CACATTCGAACATACCAGGCGAAAGCTCTTACATACGCAAATGTTTTGTCCTTCGTCGAATCGATTCGATCGAGGGTAAT
CATTAACGGTGTGACAGCGAGGTCCGAATGGGATGTGGACAAATCTTTGTTACAATCCTTGTCCATGACGTTTTACCTGC
ATACTAAGCTTGCCGTTCTAAAGGATGACTTACTGATTAGCAAGTTTAGTCTCGGTTCGAAAACGGTGTGCCAGCATGTG
TGGGATGAGATTTCGCTGGCGTTTGGGAACGCATTTCCCTCCGTGAAAGAGAGGCTCTTGAACAGGAAACTTATCAGAGT
GGCAGGCGACGCATTAGAGATCAGGGTGCCTGATCTATATGTGACCTTCCACGACAGATTAGTGACTGAGTACAAGGCCT
CTGTGGACATGCCTGCGCTTGACATTAGGAAGAAGATGGAAGAAACGGAAGTGATGTACAATGCACTTTCAGAATTATCG
GTGTTAAGGGAGTCTGACAAATTCGATGTTGATGTTTTTTCCCAGATGTGCCAATCTTTGGAAGTTGACCCAATGACGGC
AGCGAAGGTTATAGTCGCGGTCATGAGCAATGAGAGCGGTCTGACTCTCACATTTGAACGACCTACTGAGGCGAATGTTG
CGCTAGCTTTACAGGATCAAGAGAAGGCTTCAGAAGGTGCATTGGTAGTTACCTCAAGAGAAGTTGAAGAACCGTCCATG
AAGGGTTCGATGGCCAGAGGAGAGTTACAATTAGCTGGTCTTGCTGGAGATCATCCGGAATCGTCCTATTCTAAGAACGA
GGAGATAGAGTCTTTAGAGCAGTTTCATATGGCGACGGCAGATTCGTTAATTCGTAAGCAGATGAGCTCGATTGTGTACA
CGGGTCCGATTAAAGTTCAGCAAATGAAAAACTTTATCGATAGCCTGGTAGCATCACTATCTGCTGCGGTGTCGAATCTC
GTCAAGATCCTCAAAGATACAGCTGCTATTGACCTTGAAACCCGTCAAAAGTTTGGAGTCTTGGATGTTGCATCTAGGAA
GTGGTTAATCAAACCAACGGCCAAGAGTCATGCATGGGGTGTTGTTGAAACCCACGCGAGGGAGTATCATGTGGCGCTTT
TGGAATATGATGAGCAGGGTGTGGTGACATGCGATGATTGGAGAAGAGTAGCTGTTAGCTCTGAGTCTGTTGTTTATTCC
GACATGGCGAAACTCAGAACTCTGCGCAGACTGCTTCGAAACGGAGAACCGCATGTCAGTAGCGCAAAGGTTGTTCTTGT
GGACGGAGTTCCGGGCTGTGGAAAAACCAAAGAAATTCTTTCCAGGGTTAATTTTGATGAAGATCTAATTTTAGTACCTG
GGAAGCAAGCCGCGGAAATCATCAGAAGACGTGCGAATTCCTCAGGGATTATTGTGGCCACGAAGGACAACGTTAAAACC
GTTGATTCTTTCATGATGAATTTTGGGAAAAGCACACGCTGTCAGTTCAAGAGGTTATTCATTGATGAAGGGTTGATGTT
GCATACTGGTTGTGTTAATTTTCTTGTGGCGATGTCATTGTGCGAAATTGCATATGTTTACGGAGACACACAGCAGATTC
CATACATCAATAGAGTTTCAGGATTCCCGTACCCCGCCCATTTTGCCAAATTGGAAGTTGACGAGGTGGAGACACGCAGA
ACTACTCTCCGTTGTCCAGCCGATGTCACACATTATCTGAACAGGAGATATGAGGGCTTTGTCATGAGCACTTCTTCGGT
TAAAAAGTCTGTTTCGCAGGAGATGGTCGGCGGAGCCGCCGTGATCAATCCGATCTCAAAACCCTTGCATGGCAAGATCC
TGACTTTTACCCAATCGGATAAAGAAGCTCTGCTTTCAAGAGGGTATTCAGATGTTCACACTGTGCATGAAGTGCAAGGC
GAGACATACTCTGATGTTTCACTAGTTAGGTTAACCCCTACACCGGTCTCCATCATTGCAGGAGACAGCCCACATGTTTT
GGTCGCATTGTCAAGGCACACCTGTTCGCTCAAGTACTACACTGTTGTTATGGATCCTTTAGTTAGTATCATTAGAGATC
TAGAGAAACTTAGCTCGTACTTGTTAGATATGTATAAGGTCGATCGGGAACACAATAGCAATTACAGATTGACTCGGTG
TTCAAAGGTTCCAATCTTTTTGTTGCAGCGCCAAAGACTGGTGATATTTCTGATATGCAGTTTTACTATGATAAGTGTCT
CCCAGGCAACAGCACCATGATGAATAATTTTGATGCTGTTACCATGAGGTTGACTGACATTTCATTGAATGTCAAAGATT
GCATATTGGATATGTCTAAGTCTGTTGCTGCACCTAAGGATCAAATCAAACCACTAATACCTATGGTACGAACGGCGGCA
GAAATGCCACGCCAGACTGGACTATTGGAAAATTTAGTGGCGATGATTAAAAGAAACTTTAACGCACCCGAGTTGTCTGG
CATCATTGATATTGAAAATACTGCATCTTTGGTTGTAGATAAGTTTTTTGATAGTTATTGCTTAAAGAAAAAAGAAAAC
CAAATAAAAATGTTTCTTTGTTCAGTAGAGAGTCTCTCAATAGATGGTTAGAAAAGCAGGAACAGGTAACAATAGGCCAG
CTCGCAGATTTTGATTTTGTGGATTTGCCAGCAGTTGATCAGTACAGACACATGATTAAAGCACAACCCAAACAAAAGTT
GGACACTTCAATCCAAACGGAGTACCCGGCTTTGCAGACGATTGTGTACCATTCAAAAAAGATCAATGCAATATTCGGCC
CGTTGTTTAGTGAGCTTACTAGGCAATTACTGGACAGTGTTGATTCGAGCAGATTTTTGTTTTTCACAACAAAGACACCA
GCGCAGATTCAGGATTTCTTCGGAGATCTCGACAGTCATGTGCCGATGGATGTCTTGGAGCTGGATATATCAAAATACGA
```

FIG. 13-2

```
CAAATCTCAGAATGAATTCCACTGTGCAGTAGAATACGAGATCTGGCGAAGATTGGGTTTCGAAGACTTCTTGGGAGAAG
TTTGGAAACAAGGGCATAGAAAGACCACCCTCAAGGATTATACCGCAGGTATAAAAACTTGCATCTGGTATCAAAGAAAG
AGCGGGGACGTCACGACGTTCATTGGAAACACTGTGATCATTGCTGCATGTTTGGCCTCGATGCTTCCGATGGAGAAAAT
AATCAAAGGAGCCTTTTGCGGTGACGATAGTCTGCTGTACTTTCCAAAGGGTTGTGAGTTTCCGGATGTGCAACACTCCG
CGAATCTTATGTGGAATTTTGAAGCAAAACTGTTTAAAAAACAGTATGGATACTTTTGCGGAAGATATGTAATACATCAC
GACAGAGGATGCATTGTGTATTACGATCCCCTAAAGTTGATCTCGAAACTTGGTGCTAAACACATCAAGGATTGGGAACA
CTTGGAGGAGTTCAGAAGGTCTCTTTGTGATGTTGCTGTTTCGTTGAACAATTGTGCGTATTACACACAGTTGGACGACG
CTGTATGGGAGGTTCATAAGACCGCCCCTCCAGGTTCGTTTGTTTATAAAAGTCTGGTGAAGTATTTGTCTGATAAAGTT
CTTTTTAGAAGTTTGTTTATAGATGGCTCTAGTTGTTAAAGGAAAAGTGAATATCAATGAGTTTATCGACCTGACAAAAA
TGGAGAAGATCTTACCGTCGATGTTTACCCCTGTAAAGAGTGTTATGTGTTCCAAAGTTGATAAAATAATGGTTCATGAG
AATGAGTCATTGTCAGGGGTGAACCTTCTTAAAGGAGTTAAGCTTATTGATAGTGGATACGTCTGTTTAGCCGGTTTGGT
CGTCACGGGCGAGTGGAACTTGCCTGACAATTGCAGAGGAGGTGTCAGCGTGTCTGGTGGACAAAAGGATGGAAAGAG
CCGACGAGGCCATTCTCGGATCTTACTACACAGCAGCTGCAAAGAAAAGATTTCAGTTCAAGGTCGTTCCCAATTATGCT
ATAACCACCCAGGACGCGATGAGAAACGTCTGGCAAGTTTTAGTTAATATTAGAAATGTGAAGATGTCAGCGGTTTCTG
TCCGCTTTCTCTGCAGTTTGTGTCGGTGTGTATTGTTTATAGAAATAATATAAAATTAGGTTTGAGAGAGAAGATTACAA
ACGTGAGAGACGGAGGGCCCATGGAACTTACAGAAGAAGTCGTTGATGAGTTCATGGAAGATGTCCCTATGTCGATCAGG
CTTGCAAAGTTTCGATCTCGAACCGGAAAAAAGAGTGATGTCCGCAAAGGGAAAAATAGTAGTAGTGATCGGTCAGTGCC
GAACAAGAACTATAGAAATGTTAAGGATTTTGGAGGAATGAGTTTTAAAAAGAATAATTTAATCGATGATGATTCGGAGG
CTACTGTCGCCGAATCGGATTCGTTTTAAATAGATCTTACAGTATCACTACTCCATCTCAGTTCGTGTTCTTGTCAttaa
ttaaaatgcagctgaggaacccagaactacatctgggctgcgcgcttgcgcttcgcttcctggccctcgtttcctgggac
atccctggggctagagcactggacaatggattggcaaggacgcctaccatgggctggctgcactgggagcgcttcatgtg
caaccttgactgccaggaagagccagattcctgcatcagtgagaagcttcatggagatggcagagctcatggtctcag
aaggctggaaggatgcaggttatgagtacctctgcattgatgactgttggatggctccccaaagagattcagaaggcaga
cttcaggcagacctcagcgctttcctcatgggattcgccagctagctaattatgttcacagcaaaggactgaagctagg
gatttatgcagatgttggaaataaaacctgcgcaggcttccctgggagtttggatactacgacattgatgccagacct
ttgctgactggggagtagatctgctaaaatttgatggttgttactgtgacagtttggaaaatttggcagatggttataag
cacatgtccttggccctgaataggactggcagaagcattgtgtactcctgtgagtggcctctttatatgtggcccttttca
aaagcccaattatacagaaatccgacagtactgcaatcactggcgaaattttgctgacattgatgattcctggaaaagta
taaagagtatcttggactggacatcttttaaccaggagagaattgttgatgttgctggaccaggggttggaatgaccca
gatatgttagtgattggcaactttggcctcagctggaatcagcaagtaactcagatggccctctgggctatcatggctgc
tcctttattcatgtctaatgacctccgacacatcagccctcaagccaaagctctccttcaggataaggacgtaattgcca
tcaatcaggacccctgggcaagcaagggtacagcttagacagggagacaactttgaagtgtgggaacgacctctctca
ggcttagcctgggctgtagctatgataaaccggcaggagattggtggacctcgctcttataccatcgcagttgcttccct
gggtaaaggagtggcctgtaatcctgcctgcttcatcacacagctcctccctgtgaaaaggaagctagggttctatgaat
ggacttcaaggttaagaagtcacataaatcccacaggcactgttttgcttcagctatctgaaaaggacgaattatgacct
aggGGGTAGTCAAGATGCATAATAAATAACGGATTGTGTCCGTAATCACACGTGGTGCGTACGATAACGCATAGTGTTTT
TCCCTCCACTTAAATCGAAGGGTTGTGTCTTGCATCGCGCGGGTCAAATGTATATGGTTCATATACATCCGCAGGCACGT
AATAAAGCGAGGGGTTCGGGTCGAGGTCGGCTGTGAAACTCGAAAAGGTTCCGGAAAACAAAAAAGAGAGTGGTAGGTAA
TAGTGTTAATAATAAGAAAATAAATAATAGTGGTAAGAAAGGTTTGAAAGTTGAGGAAATTGAGGATAATGTAAGTGATG
ACGAGTCTATCGCGTCATCGAGTACGTTTTAATCAATATGCCTTATACAATCAACTCTCCGAGCCAATTTGTTTACTTAA
GTTCCGCTTATGCAGATCCTGCTGCAGCTGATCAATCTGTGTACAAATGCATTGGGTAACCAGTTTCAAACGCAACAAGCT
AGGACAACAGTCCAACAGCAATTTGCGGATGCCTGGAAACCTGTGCCTAGTATGACAGTGAGATTTCCTGCATCGGATTT
CTATGTGTATAGATATAATTCGACGCTTGATCCGTTGATCACGGCGTTATTAAATAGCTTCGATACTAGAAATAGAATAA
TAGAGGTTGATAATCAACCCGCACCGAATACTACTGAAATCGTTAACGCGACTCAGAGGGTAGACGATGCGACTGTAGCT
ATAAGGGCTTCAATCAATAATTTGGCTAATGAACtGGTTCGTGGAACTGGCaTGTTCAATCAAGCAAGCTTTGAGACTGC
TAGTGGACTTGTCTGGACCACAACTCCGGCTACTTAGctattgttgtgagatttcctaaaataaagtcactgaagactta
aaattcagggtggctgataccaaaatcagcagtggttgttcgtccacttaaatataacgattgtcatatctggatccaac
agttaaaccatgtgatggtgtatactgtggtatggcgtaaaacaacggaaaagtcgctgaagacttaaaattcagggtgg
ctgataccaaaatcagcagtggttgttcgtccacttaaaaataacgattgtcatatctggatccaacagttaaaccatgt
gatggtgtatactgtggtatggcgtaaaacaacggagaggttcgaatcctcccctaaccgcgggtagcggccca
```

TRANSGENIC VECTOR FOR rGCB EXPRESSION

US 6,846,968 B1

PRODUCTION OF LYSOSOMAL ENZYMES IN PLANTS BY TRANSIENT EXPRESSION

PRIORITY DATA

The present application is a continuation-in-part of application Ser. No. 09/316,572, filed May 21, 1999, now abandoned, which is a continuation of application Ser. No. 08/324,003, filed Oct. 14, 1994, now U.S. Pat. No. 5,977,438, which is a continuation-in-part of application Ser. No. 08/176,414, filed on Dec. 29, 1993, now U.S. Pat. No. 5,811,653, which is a continuation-in-part of application Ser. No. 07/997,733, filed Dec. 30, 1992, now abandoned. Application Ser. No. 08/324,003, filed Oct. 14, 1994, now U.S. Pat. No. 5,977,438 is also a continuation-in-part of application Ser. No. 08/184,237, filed Jan. 19, 1994, now U.S. Pat. No. 5,589,367, which is a continuation-in-part of application Ser. No. 07/923,692, filed Jul. 31, 1992, now U.S. Pat. No. 5,316,931, which is a continuation-in-part of applications Ser. No. 07/600,244, filed Oct. 22, 1990, now abandoned, Ser. No. 07/641,617, filed Jan. 16, 1991, now abandoned, application Ser. No. 07/737,899, filed Jul. 26, 1991, now abandoned, and application Ser. No. 07/739,143, filed Aug. 1, 1991, now abandoned. Application Ser. No. 07/600,244 is a continuation of application Ser. No. 07/310,881, filed Feb. 17, 1989, now abandoned, which is a continuation-in-part of applications Ser. No. 07/160,766 and Ser. No. 07/160,771, both filed on Feb. 26, 1988 and now abandoned. Application Ser. No. 07/641,617 is a continuation of application Ser. No. 07/347,637, filed May 5, 1989, now abandoned. Application Ser. No. 07/737,899 is a continuation of application Ser. No. 07/363,138, filed Jun. 8, 1989, now abandoned, which is a continuation-in-part of application Ser. No. 07/219,279, filed Jul. 15, 1988, now abandoned. Application Ser. No. 07/739,143 is a continuation-in-part of applications Ser. No. 07/600,244, filed Oct. 22, 1990, now abandoned, Ser. No. 07/641,617, filed Jan. 16, 1991, now abandoned, and Ser. No. 07/737,899, filed Jul. 26, 1991, now abandoned. All of the above referenced priority applications are incorporated herein by reference in their entirety.

Parts of this work were supported under National Institute of Diabetes and Digestive and Kidney Diseases Grant No. 1 R43 DK48528-01

FIELD OF THE INVENTION

This invention is in the field of therapeutic peptides. Specifically this invention relates to the production of pharmaceutical peptides and proteins encoded on a recombinant plant virus or and produced by an infected plant or produced by a recombinant plant. The present invention relates especially to the production of human and animal lysosomal enzymes in plants comprising expressing the genetic coding sequence of a human or animal lysosomal enzyme in a plant expression system. The plant expression system provides for post-translational modification and processing to produce recombinant protein having enzymatic activity. The invention is demonstrated herein by working examples in which transgenic or transfected tobacco plants produce a modified human α galactosidase and a glucocerebrosidase, both of which are enzymatically active. The recombinant lysosomal enzymes produced in accordance with the invention may be used for a variety of purposes including but not limited to enzyme replacement therapy for the therapeutic treatment of lysosomal storage diseases, research for development of new approaches to medical treatment of lysosomal storage diseases, and industrial processes involving enzymatic substrate hydrolysis.

BACKGROUND OF THE INVENTION

Lysosomes, which are present in all animal cells, are acidic cytoplasmic organelles that contain an assortment of hydrolytic enzymes. These enzymes function in the degradation of internalized and endogenous macromolecular substrates. When there is a lysosomal enzyme deficiency, the deficient enzyme's undegraded substrates gradually accumulate within the lysosomes causing a progressive increase in the size and number of these organelles within the cell. This accumulation within the cell eventually leads to malfunction of the organ and to the gross pathology of a lysosomal storage disease, with the particular disease depending on the particular enzyme deficiency. More than thirty distinct, inherited lysosomal storage diseases have been characterized in humans.

Enzyme Replacement Therapy

One proven treatment for lysosomal storage diseases is enzyme replacement therapy in which an active form of the enzyme is administered directly to the patient. However, abundant, inexpensive and safe supplies of therapeutic lysosomal enzymes are not commercially available for the treatment of any of the lysosomal storage diseases. There is a large number of metabolic storage disorders known to affect man. As a group, these diseases are the most prevalent genetic abnormalities of humans, yet individually they are quite rare. One of the three major classes of these conditions, comprising the majority of patients, is the sphingolipidoses in which excessive quantities of undegraded fatty components of cell membranes accumulate because of inherited deficiencies of specific catabolic enzymes. Principal disorders in this category are Gaucher disease, Niemann-Pick disease, Fabry disease, and Tay-Sachs disease. All of these disorders are caused by harmful mutations in the genes that code for specific housekeeping enzymes within lysosomes. Thus, to be effective, enzyme replacement therapy requires that the requisite exogenous enzyme be taken up by the cells in which the materials are catabolized and that they be incorporated into lysosomes within these cells. Fabry disease is an ideal candidate for enzyme replacement therapy because the disease does not involve the central nervous system. The therapeutic enzyme does not need to be delivered across the blood-brain barrier (1, 2).

The effectiveness of enzyme replacement therapy has been dramatically documented in the treatment of patients with Gaucher disease. This condition is the most frequent of all metabolic storage disorders. It is estimated that there are 15,000 patients with this condition in the United States and about 80,000 worldwide. Soon after the enzymatic defect in Gaucher disease was established, consideration was given to the possibility of treating patients with purified α-glucocerebrosidase (3). Dr. Brady elected to use human placental tissue as the source of enzyme in order to minimize sensitizing patients to the exogenous protein. Initial studies with small amounts of glucocerebrosidase injected intravenously into patients with Gaucher disease revealed that the exogenous enzyme reduced the quantity of accumulated glucocerebroside in the liver and in the blood (4). A large-scale enzyme purification procedure was developed in order to obtain sufficient quantities for clinical efficacy trials (5). It was then learned that modifications of the terminal sugars on oligosaccharide chains of the enzyme were necessary in order to target intravenously administered enzyme to macrophages where most of the glucocerebroside is stored. Targeting to macrophages was accomplished by sequential enzymatic removal of monosaccharide residues from glucocerebrosidase resulting in mannose-terminal glucocerebrosidase (6). Administration of this glycoform of glucocerebrosidase to patients has brought about immense improvement in their condition (7–10). The modified enzyme (alglucerase) is now produced commercially by Genzyme Corporation in Cambridge, Mass., under the trade name Ceredase™. The beneficial effects of this treatment have been universally confirmed (11–13). Production of recombinant glucocerebrosidase (imiglucerase) is underway in Chinese hamster ovary (CHO) cells, and the product (Cerezyme™) is as effective as placental glucocerebrosidase (14). The experience with Gaucher treatment validates enzyme replacement therapy with a product that requires post-translational modifications.

Fabry disease is caused by deficiencies in the catalytic activity of the lysosomal enzyme α galactosidase A (Gal-A). Human Gal-A is a glycoprotein homodimer with a molecular weight of approximately 101 kDa containing 5–15% Asn-linked carbohydrate. The enzyme contains approximately equal portions of high mannose and complex type glycans. Upon isoelectric focusing, many forms of the enzyme are observed due to differences in sialylation depending on the source of the protein (tissue or plasma forms). The disease is inherited as an X-linked recessive trait. A number of specific mutations in the gene have been characterized, including partial rearrangements, splice-junction defects and point mutations. Most of these mutations are private and therefore, the gene appears to be highly mutable relative to genes encoding other housekeeping enzymes. Defects result in the accumulation of glycosphingolipid substrates, globotriaosylceramide and related glycolipids with terminal α-galactosidic linkages. Uncatabolized substrate accumulates in the plasma, vascular endothelium and various organs leading to an early demise from vascular disease of the heart, brain, and kidney, particularly in the classically affected hemizygous males. In addition to systemic disease, affected individuals often suffer from peripheral neuropathies and have characteristic angiokeratoma of the skin. Heterozygous female carriers may have a more attenuated range of disease phenotypes (1,2).

Exploratory trials of enzyme replacement therapy for Fabry disease have demonstrated the biochemical effectiveness of this approach (15–18). Repeated injections of purified splenic and plasma Gal-A reduced the level of plasma substrate and may have mobilized stored tissue substrate into circulation. No immunological complications were apparent in repeated infusions of enzyme into hemizygous males. Further investigations have not been attempted because of the great difficulty in obtaining sufficient quantities of enzyme for a meaningful replacement trial. The availability of large quantities of enzyme would enable optimization of glycoforms for therapeutic efficacy by improving cell targeting and prolonging the half-life in circulation and target organs.

Galactosidase

In the early 1970's, several investigators demonstrated the existence of two .α.-Galactosidase isozymes designated A and B, which hydrolyzed the α.-galactosidic linkages in 4-MU-and/or .rho.-NP-α-D-galactopyranosides (62, 63, 64, 65, 66, 67, 68, 69). In tissues, about 80%–90% of total α-Galactosidase (.α.-Gal) activity was due to a thermolabile, myoinositol-inhibitable α-Gal A isozyme, while a relatively thermostable, .α.-Gal B, accounted for the remainder. The two "isozymes" were separable by electrophoresis, isoelectric focusing, and ion exchange chromatography. After neuraminidase treatment, the electrophoretic migrations and pI value of α-Gal A and B were similar (70), initially suggesting that the two enzymes were the differentially glycosylated products of the same gene. The finding that the purified glycoprotein enzymes had similar physical properties including subunit molecular weight (.about.46 kDa), homodimeric structures, and amino acid compositions also indicated their structural relatedness (70. 71. 72. 73. 74. 75. 76. 77). However, the subsequent demonstration that polyclonal antibodies against .α.-Gal A or B did not cross-react with the other enzyme (78, 79) that only .α.-Gal A activity was deficient in hemizygotes with Fabry disease (80, 81, 82, 83, 84, 85, 86) and that the genes for .α.-Gal A and B mapped to different chromosomes (Desnick, et al., 1989, in The Metabolic Basis of Inherited Disease, Scriver, C. R., Beaudet, A. L. Sly, W. S. and Valle, D., eds, pp. 1751–1796, McGraw Hill, N.Y.; deGroot, et al., 1978, Hum. Genet. 44:305–312), clearly demonstrated that these enzymes were genetically distinct.

α-Gal A and Fabry Disease

In Fabry disease, a lysosomal storage disease resulting from the deficient activity of .α.-Gal A, identification of the enzymatic defect in 1967 (Brady, et al., 1967, N. Eng. J. Med. 276:1163) led to the first in vitro (Dawson, et al., 1973, Pediat. Res. 7: 694–690m) and in vivo (Mapes, et al., 1970, Science 169:987) therapeutic trials of .α.-Gal A replacement in 1969 and 1970, respectively. These and subsequent trials (Mapes, et al., 1970, Science 169:987; Desnick, et al., 1979, Proc. Natl. Acad. Sci. USA 76: 5326; and, Brady, et al., 1973, N. Engl. J. Med. 289: 9) demonstrated the biochemical effectiveness of direct enzyme replacement for this disease. Repeated injections of purified splenic and plasma .α.-Gal A (100,000 U/injection) were administered to affected hemizygotes over a four month period (Desnick, et al., 1979, Proc. Natl. Acad. Sci. USA 76:5326). The results of these studies demonstrated that (a) the plasma clearance of the splenic form was 7 times faster than that of the plasma form (10 min vs 70 min); (b) compared to the splenic form of the enzyme, the plasma form effected a 25-fold greater depletion of plasma substrate over a markedly longer period (48 hours vs 1 hour); (c) there was no evidence of an immunologic response to six doses of either form, administered intravenously over a four month period to two affected hemizygotes; and (d) suggestive evidence was obtained indicating that stored tissue substrate was mobilized into the circulation following depletion by the plasma form, but not by the splenic form of the enzyme. Thus, the administered enzyme not only depleted the substrate from the circulation (a major site of accumulation), but also possibly mobilized the previously stored substrate from other depots into the circulation for subsequent clearance. These studies indicated the potential for eliminating, or significantly reducing, the pathological glycolipid storage by repeated enzyme replacement. However, the biochemical and clinical effectiveness of enzyme replacement in Fabry disease has not been commercially available due to the lack of sufficient human enzyme for adequate doses and longterm evaluation.

The α-Gal A Enzyme

The .α.-Gal A human enzyme has a molecular weight of approximately 101,000 Da. On SDS gel electrophoresis it migrates as a single band of approximately 49,000 Da indicating the enzyme is a homodimer (Bishop & Desnick, 1981, J. Biol. Chem. 256: 1307). α-Gal A is synthesized as a 50,500 Da precursor containing phosphorylated endoglycosidase H sensitive oligosaccharides. This precursor is processed to a mature form of about 46,000 Da within 3–7 days after its synthesis. The intermediates of this processing have not been defined (Lemansky, et al., 1987, J. Biol. Chem. 262:2062). As with many lysosomal enzymes, .α.-Gal A is targeted to the lysosome via the mannose-6-phosphate receptor. This is evidenced by the high secretion rate of this enzyme in mucolipidosis II cells and in fibroblasts treated with NH.sub.4 Cl.

The enzyme has been shown to contain 5–15% Asn linked carbohydrate (Ledonne, et al., 1983, Arch. Biochem. Biophys. 224:186). The tissue form of this enzyme was shown to have .about.52% high mannose and 48% complex type oligosaccharides. The high mannose type coeluted, on Biogel chromatography, with Man.sub.8–9 GlcNAc while the complex type oligosaccharides were of two categories containing 14 and 19–39 glucose units. Upon isoelectric focusing many forms of this enzyme are observed depending on the sources of the purified enzyme (tissue vs plasma form). However, upon treatment with neuraminidase, a single band is observed (pI-5.1) indicating that this heterogeneity is due to different degrees of sialylation (Bishop & Desnick, 1981, J. Biol. Chem. 256:1307). Initial efforts to express the full-length cDNA encoding .α.-Gal A involved using various prokaryotic expression vectors (Hantzopoulos and Calhoun, 1987, Gene 57:159; Ioannou, 1990, Ph.D. Thesis, City University of New York). Although microbial expression was achieved, as evidenced by enzyme assays of intact E. coli cells and growth on melibiose as the carbon source, the human protein was expressed at low levels and could not be purified from the bacteria. These results indicate that the recombinant enzyme was unstable due to the lack of normal glycosylation and/or the presence of endogenous cytoplasmic or periplasmic proteases.

Gaucher Disease and Treatment

Gaucher disease is the most common lysosomal storage disease in humans, with the highest frequency encountered in the Ashkenazi Jewish population. About 5,000 to 10,000 people in the United States are afflicted with this disease (Grabowski, 1993, Adv. Hum. Genet. 21:377–441). Gaucher disease results from a deficiency in glucocerebrosidase (hGCB); glucosylceramidase; acid β-glucosidase; EC 3.2.1.45). This deficiency leads to an accumulation of the enzyme's substrate, glucocerebroside, in reticuloendothelial cells of the bone marrow, spleen and liver, resulting in significant skeletal complications such as bone marrow expansion and bone deterioration, and also hypersplenism, hepatomegaly, thrombocytopenia, anemia and lung complications (Grabowski, 1993, supra; Lee, 1982, Prog. Clin. Biol. Res. 95:177–217; Brady et al., 1965, Biochem. Biophys. Res. Comm. 18:221–225). hGCB replacement therapy has revolutionized the medical care and management of Gaucher disease, leading to significant improvement in the quality of life of many Gaucher patients (Pastores et al., 1993, Blood 82:408–416; Fallet et al., 1992, Pediatr. Res. 31:496–502). Studies have shown that regular, intravenous administration of specifically modified hGCB (Ceredase.TM., Genzymne Corp.) can result in dramatic improvements and even reversals in the hepatic, splenic and hematologic manifestations of the disease (Pastores et al., 1993, supra; Fallet: et al., 1992, supra; Figueroa et al., 1992, N. Eng. J. Med 327:1632–1636; Barton et al., 1991, N. Eng. J. Med. 324:1464–1470; Beutler et al., 1.991, Blood 78:1183–1189). Improvements in associated skeletal and lung complications are possible, but require larger doses of enzyme over longer periods of time.

Despite the benefits of hGCB replacement therapy, the source and high cost of the enzyme seriously restricts its availability. Until recently, the only commercial source of purified hGCB has been from pooled human placentae, where ten to twenty kilograms (kg) of placentae yield only 1 milligram (mg) of enzyme. From five hundred to two thousand kilograms of placenta (equivalent to 2,000–8,000 placentae) are required to treat each patient every two weeks. Current costs for hGCB replacement therapy range from $55 to $220/kg patient body weight every two weeks, or from $70,000 to $300,000/year for a 50 kg patient. Since the need for therapy essentially lasts for the duration of a patient's life, costs for the enzyme alone may exceed $15,000,000 during 30 to 70 years of therapy.

A second major problem associated with treating Gaucher patients with glucocerebrosidase isolated from human tissue (and perhaps even from other animal tissues) is the risk of exposing patients to infectious agents which may be present in the pooled placentae, e.g., human immuno-deficiency virus (HIV), hepatitis viruses, and others.

Accordingly, a new source of hGCB is needed to effectively reduce the cost of treatment and to eliminate the risk of exposing Gaucher patients to infectious agents.

Hurler Syndrome and Treatment

Hurler syndrome is the most common of the group of human lysosomal storage disorders known as the mucopolysaccharidosis (MPS) involving an inability to degrade dermatan sulfate and heparan sulfate. Hurler patients are deficient in the lysosomal enzyme, α-L-iduronidase (IDUA), and the resulting accumulation of glucosaminoglycans in the lysosomes of affected cells leads to a variety of clinical manifestations (Neufeld & Ash well, 1980, The Biochemistry of Glycoproteins and Proteoglycans, ed. W. J. Lennarz, Plenum Press, N.Y.; pp. 241–266) including developmental delay, enlargement of the liver and spleen, skeletal abnormalities, mental retardation, coarsened facial features, corneal clouding, and respiratory and cardiovascular involvement. Hurler/Scheie syndrome (MPS I H/S) and Scheie syndrome (MPS IS) represent less severe forms of the disorder but also involve deficiencies in IDUA. Molecular studies on the genes and cDNAs of MPS I patients has led to an emerging understanding of genotype and clinical phenotype (Scott et al., 1990, Am. J. Hum. Genet. 47:802–807). In addition, both a canine and feline form of MPS I have been characterized (Haskins et al., 1979, Pediat. Res. 13:1294–1297; Haskins and Kakkis, 1995, Am. J. Hum. Genet. 57:A39 Abstr. 194; Shull et al., 1994, Proc. Natl. Acad. Sci. USA, 91:12937–12941) providing an effective in vivo model for testing therapeutic approaches.

The efficacy of enzyme replacement in the canine model of Hurler syndrome using human IDUA generated in CHO cells was recently reported (Kakkis et al., 1995, Am. J. Hum. Genet. 57:A39 (Abstr.); Shull et al., 1994, supra). Weekly doses of approximately 1 mg administered over a period of 3 months resulted in normal levels of the enzyme in liver and spleen, lower but significant levels in kidney and Lungs and very low levels in brain, heart, cartilage and cornea (Shull et al., 1994, supra. Tissue examinations showed normalization of lysosomal storage in the liver, spleen and kidney, but no improvement in heart, brain and corneal tissues. One dog was maintained on treatment for 13 months and was clearly more active with improvement in skeletal deformities, joint stiffness, corneal clouding and weight gain (Kakkis et al., 1995, supra. A single higher-dose experiment was quite promising and showed detectable IDUA activity in the brain and cartilage in addition to tissues which previously showed activity at the lower does. Additional higher-dose experiments and trials involving longer administration are currently limited by availability of recombinant enzyme. These experiments underscore the-potential of replacement therapy for Hurler patients and the severe constraints on both canine and human trials due to limitations in recombinant enzyme production using current technologies.

Lysosomal Enzymes: Biosynthesis and Targeting

Lysosomal enzymes are synthesized on membrane-bound polysomes in the rough endoplasmic reticulum. Each protein is synthesized as a larger precursor containing a hydrophobic amino terminal signal peptide. This peptide interacts with a signal recognition particle, an 11S ribonucleoprotein, and thereby initiates the vectoral transport of the nascent protein across the endoplasmic reticulum membrane into the lumen (Erickson, et al., 1981, J. Biol. Chem. 256:11224; Erickson, et al., 1983, Biochem. Biophys. Res. Commun. 115:275; Rosenfeld, et al., 1982, J. Cell Biol. 93:135). Lysosomal enzymes are cotranslationally glycosylated by the en bloc transfer of a large preformed oligosaccharide, glucose-3, mannose-9, N-acetylglucosamine-2, from a lipid-linked intermediate to the Asn residue of a consensus sequence Asn-X-Ser/Thr in the nascent polypeptide (Kornfeld, R. & Komfeld, S., 1985, Annu. Rev. Biochem. 54:631). In the endoplasmic reticulum, the signal peptide is cleaved, and the processing of the Asn-linked oligosaccharide begins by the excision of three glucose residues and one mannose from the oligosaccharide chain.

The proteins move via vesicular transport, to the Golgi stack where they undergo a variety of posttranslational modifications, and are sorted for proper targeting to specific destinations: lysosomes, secretion, plasma membrane. During movement through the Golgi, the oligosaccharide chain on secretory and membrane glycoproteins is processed to the sialic acid-containing complex-type. While some of the oligosaccharide chains on lysosomal enzymes undergo similar processing, most undergo a different series of modifications. The most important modification is the acquisition of phosphomannosyl residues which serve as an essential component in the process of targeting these enzymes to the lysosome (Kaplan, et al., 1977, Proc. Natl. Acad. Sci. USA 74:2026). This recognition marker is generated by the sequential action of two Golgi enzymes. First, N-acetylglucosaminyl-phosphotransferace transfers N-acetylglucosamine-1-phosphate from the nucleotide sugar uridine diphosphate-N-acetylglucosamine to selected mannose residues on lysosomal enzymes to give rise to a phosphodiester intermediate (Reitmran & Kornfeld, 1981, J. Biol. Chem. 256:4275; Waheed, et al., 1982, J. Biol. Chem. 257:12322). Then, N-acetylglucosamine-1-phosphodiester . α.-N-acetylglucosaminiidase removes N-acetylglucosamine residue to expose the recognition signal, mannose-6-phosphate (Varki & Komfeld, 1981, J. Biol. Chem. 256: 9937; Waheed, et al., 1981, J. Biol. Chem. 256:5717).

Following the generation of the phosphomannosyl residues, the lysosomal enzymes bind to mannose-6-phosphate (M-6-P) receptors in the Golgi. In this way the lysosomal enzymes remain intracellular and segregate from the proteins which are destined for secretion. The ligand-receptor complex then exits the Golgi via a coated vesicle and is delivered to a prelysosomal staging area where dissociation of the ligand occurs by acidification of the compartment (Gonzalez-Noriega, et al., 1980, J. Cell Biol. 85: 839). The receptor recycles back to the Golgi while the lysosomal enzymes are packaged into vesicles to form primary lysosomes. Approximately, 5–20% of the lysosomal enzymes do not traffic to the lysosomes and are secreted presumably, by default. A portion of these secreted enzymes may be recaptured by the M-6-P receptor found on the cell surface and be internalized and delivered to the lysosomes (Willingham, et al., 1981, Proc. Natl. Acad. Sci. USA 78:6967).

Two mannose-6-phosphate receptors have been identified. A 215 kDa glycoprotein has been purified from a variety of tissues (Sahagian, et al., 1981, Proc. Natl. Acad. Sci. USA, 78:4289; Steiner & Rome, 1982, Arch. Biochem. Biophys. 214:681). The binding of this receptor is divalent cation independent. A second M-6-P receptor also has been isolated which differs from the 215 kDa receptor in that it has a requirement for divalent cations. Therefore, this receptor is called the cation-dependent (M-6-P.sup.CD) while the 215 kDa one is called cation-independent (M-6-P.sup.CI). The M-6-P.sup.CD receptor appears to be an oligomer with three subunits with a subunit molecular weight of 46 kDa.

Biosynthesis of Lysosomal Enzymes.

Although many lysosomal enzymes are soluble and are transported to lysosomes by M-6-P receptors (MPR), integral membrane and membrane-associated proteins such as human glucocerebrosidase (hGCB) are targeted and transported to lysosomes independent of the M-6-P/MPR system (Komfeld & Mellman, 1989, Erickson et al., 1985). hGCB does not become soluble after translation, but instead becomes associated with the lysosomal membrane by means which have not been elucidated (von Figura & Hasilik, 1986, Annu. Rev. Biochem. 55:167–193; Komfeld and Mellman, 1989, Annu. Rev. Cell Biol. 5:483–525). hGCB is synthesized as a single polypeptide (58 kDa) with a signal sequence (2 kDa) at the amino terminus. The signal sequence is co-translationally cleaved and the enzyme is glycosylated with a heterogeneous group of both complex and high-mannose oligosaccharides to form a precursor. The glycans are predominately involved in protein conformnation. The "high mannose" precursor, which has a molecular weight of 63 KDa, is post-translationally processed in the Golgi to a 66 KDa intermediate, which is then further modified in the lysosome to the mature enzyme having a molecular weight of 59 KDa (Jonsson et al., 1987, Eur. J. Biochem. 164:171; Erickson et al., 1985, J. Biol. Chem., 260:14319).

The mature hGCB polypeptide is composed of 497 amino acids and contains five N-glycosylation amino acid consensus sequences (Asn-X-Ser/Thr). Four of these sites are normally glycosylated. Glycosylation of the first site is essential for the production of active protein. Both high-mannose and complex oligosaccharide chains have been identified (Berg-Fussman et al., 1993, J. Biol. Chem. 268:14861–14866). hGCB from placenta contains 7% carbohydrate, 20% of which is of the high-mannose type (Grace & Grabowski, 1990, Biochem. Biophys. Res. Comm. 168:771–777). Treatment of placental hGCB with neuraminidase (yielding an asialo enzyme) results in increased clearance and uptake rates by rat liver cells with a concomitant increase in hepatic enzymatic activity (Furbish et al., 1981, Biochim. Biophys. Acta 673:425–434). This glycan-modified placental hGCB is currently used as a therapeutic agent in the treatment of Gaucher's disease. Biochemical and site-directed mutagenesis studies have provided an initial map of regions and residues important to folding, activator interaction, and active site location (Grace et al., 1994, J. Biol. Chem. 269:2283–2291).

The complete complementary DNA (cDNA) sequence for hGCB has been published (Tsuji et al., 1986, J. Biol. Chem. 261:50–53; Sorge et al., 1985, Proc. Natl. Acad. Sci. USA 82:7289–7293), and *E. coli* containing the hGCB cDNA sequence cloned from fibroblast cells, as described (Sorge et al., 1985, supra), is available from the American Type Culture Collection (ATCC) (Accession No. 65696).

Recombinant methodologies have the potential to provide a safer and less expensive source of lysosomal enzymes for replacement therapy. However, production of active enzymes, e.g., hGCB, in a heterologous system requires correct targeting to the ER, and appropriate N-linked glycosylation at levels or efficiencies that avoid ER-based degradation or aggregation. Since mature lysosomal enzymes must be glycosylated to be active, bacterial systems cannot be used. For example, hGCB expressed in *E. coli* is enzymatically inactive (Grace & Grabowski, 1990, supra).

Active monomers of hGCB have been purified from insect cells (Sf9 cells) and Chinese hamster ovary (CHO) cells infected or transfected, respectively, with hGCB cDNA (Grace & Grabowski, 1990, supra; Grabowski et al., 1989, Enzyme 41:131–142). A method for producing recombinant hGCB in CHO cell cultures and in insect cell cultures was recently disclosed in U.S. Pat. No. 5,236,838. Recombinant hGCB produced in these heterologous systems had an apparent molecular weight ranging from 64 to 73 kDa and contained from 5 to 15% carbohydrate (Grace & Grabowski, 1990, supra; Grace et al., 1990, J. Biol. Chem. 265:6827–6835). These recombinant hGCBs had kinetic properties identical to the natural enzyme isolated from human placentae, as based on analyses using a series of substrate and transition state analogues, negatively-charged lipid activators, protein activators (saposin C), and mechanism-based covalent inhibitors (Grace et al., 1994, supra; Berg-Fussman et al., 1993, supra; Grace et al., 1990, J. Biol. Chem. 265:6827–6835; Grabowski et al., 1989, supra) However, both insect cells and CHO cells retained most of the enzyme rather than secreting it into the medium, significantly increasing the difficulty and cost of harvesting the pure enzyme (Grabowski et al., 1989, supra). Accordingly, a recombinant system is needed that can produce human or animal lysosomal enzymes in an active form at lower cost, and that will be appropriately targeted for ease of recovery.

Enormous Costs of Pharmaceutical Enzyme Production

While the clinical treatment of Gaucher patients provides a dramatically successful example of an effective therapy, the expense underscores an equally inadequate production technology. For example, the present cost for the first year of treatment for a severely affected 70 kg patient with Gaucher disease can reach $382,000. If the patient's clinical parameters are not restored to normal in that time, treatment at this level of expense will be prolonged before dose reduction can be initiated. Even with dose reduction, it is likely that the maintenance cost for such an individual will be in the range of $135,000 per year (at $3.70/IU). Many patients are unable to pay this large cost, and health carriers are extremely reluctant to underwrite this treatment for the life of these patients. Cerezyme™ is as expensive as Ceredase™ and at this time is available only in limited quantities. The number of patients with Gaucher disease in the US currently receiving therapy is estimated to be only 10–15% of the total. According an article in Nature Medicine, since the introduction of this therapy six years ago the cost of treating Gaucher patients worldwide will soon approach one billion dollars (19). Although the total number of patients worldwide who would benefit from therapy is not known with any certainty, it is safe to assume that at least 80% of the world Gaucher population remain untreated. To quote from the NIH Technology Assessment Conference Summary Statement, Feb. 27-Mar. 1, 1995. "As a prototype for all rare diseases, the plight of patients with Gaucher disease raises difficult financial and ethical issues, which we as a society must address (20)." Fabry disease is estimated to occur at a frequency of 1 in 40,000. Over 400 hemizygous male patients have been clinically described. It is imperative that fundamentally new methods of enzyme production be developed to reduce these costs so that all who suffer from these rare disorders can be treated.

Mammalian Lysosomes Versus Plant Vacuoles

Because plants are eukaryotes, plant expression systems have advantages over prokaryotic expression systems, particularly with respect to correct processing of eukaryotic gene products. However, unlike animal cells, plant cells do not possess lysosomes. Although the plant vacuole appears functionally analogous to the lysosome, plants do not contain MPRs (Chrispeels, 1991, Ann. Rev. Pl. Phys. Pl. Mol. Biol. 42:21–53; Chrispeels and Tague, 1991, Intl. Rev. Cytol. 125:1–45), and the mechanisms of vacuolar targeting can differ significantly from those of lysosomal targeting. For example, the predominant mechanism of vacuolar targeting in plants does not appear to be glycan-dependent, but appears to be based instead on C- or N-terminal peptide sequences (Gomez & Chrispeels, 1993, Plant Cell 5:1113–1124; Chrispeels & Raikhal, 1992, Cell 68:613–618; Holwerda et al., 1992, Plant Cell 4:307–318; Neuhaus et al., 1991, Proc. Natl. Acad. Sci. USA 88:10362–10366; Chrispeels, 1991, supra; Chrispeels & Tague, 1991, supra; Holwerda et al., 1990, Plant Cell 2:1091–1106; Voelker et al., 1989, Plant Cell 1:95–104). As a result, plants have not been viewed as appropriate expression systems for lysosomal enzymes which must be appropriately processed to produce an active product.

An object of this invention is to provide the existing patient population with enough active enzyme to develop a lower cost treatment. The enzymatic, structural, and glycan compositional analyses show rGal to be active. There are recent advances in glycoprotein modification and drug delivery that allow, as examples, the chemical conjugation of peptides to carbohydrate, the covalent addition of polyethylene glycol to enzymes and the liposomal encapsulation of protein. Many additional new concepts can be tested to increase the half-life of enzymes in circulation and optimize cellular and subcellular targeting. Ideally, these modifications will require a facile and rapid genetic system to produce large quantities of highly pure enzyme and an effective animal disease model for drug development. Our lab-scale process appears highly scalable and is capable of producing grams of enzyme per month in existing indoor greenhouse growth areas.

Using a viral transfection system and transgenic plants, we have expressed enzymes in plants that have potential as therapeutic agents for humans with the metabolic storage disorders known as Fabry disease and Gaucher disease. High specific activity recombinant enzymes were secreted by tobacco leaf cells via a default pathway of protein sorting into the apoplastic compartment, a network of extracellular space, cell wall matrix materials and intercellular fluid (IF). We further developed a novel bioprocessing method to purify these enzymes from the IF fraction.

Another object of this invention is to provide an optimized preproenzyme amino acid (AA) sequence for secretion of highly active lysosomal enzymes. Another object of this invention is to provide an optimized purification of lysosomal enzymes from either the IF fraction or from whole plant homogenates. Another object of this invention is to provide a molecular characterization of the enzymes purified by this process, including determination of enzyme specific activity.

SUMMARY OF THE INVENTION

The present invention relates to the production of human or animal lysosomal enzymes in transformed or transfected plants, plant cells or plant tissues, and involves constructing and expressing recombinant expression constructs comprising lysosomal enzyme coding sequences in a plant expression system. The plant expression system provides appropriate co-translational and post-translational modifications of the nascent peptide required for processing, e.g., signal sequence cleavage, glycosylation, and sorting of the expression product so that an enzymatically active protein is produced. Using the methods described herein, recombinant lysosomal enzymes are produced in plant expression systems from which the recombinant lysosomal enzymes can be isolated and used for a variety of purposes. The present invention is exemplified by virally transfected and transgenic tobacco plants with lysosomal enzyme expression constructs. One construct comprises a nucleotide sequence encoding a modified human glucocerebrosidase (hGCB). Another construct comprises nucleotide sequence encoding a human α galactosidase (α gal or α gal A). Virally transfected and transgenic tobacco plants having the expression constructs produce lysosomal enzymes that are enzymatically active and have high specific activity.

The plant expression systems and the recombinant lysosomal enzymes produced therewith have a variety of uses, including but not limited to: (1) the production of enzymatically active lysosomal enzymes for the treatment of lysosomal storage diseases; (2) the production of altered or mutated proteins, enzymatically active or otherwise, to serve as precursors or substrates for further in vivo or in vitro processing to a specialized industrial form for research or therapeutic uses, such as to produce a more effective therapeutic enzyme; (3) the production of antibodies against lysosomal enzymes for medical diagnostic use; and (4) use in any commercial process that involves substrate hydrolysis.

BRIEF DESCRIPTION OF FIGURES

FIG. 5 shows carboxy terminal modifications to α galactosidase (SEQ ID NOs:3–12).

FIG. 12 shows TTODA (rGAL-12R) TMV RNA begins at base 1; 126/183 reading frame begins at 69,3417 is suppressible stop codon, and ends at 4919.30K ORF begins at 4903 and ends at 5709. Human α galactosidase A RNA begins at 5703, α amylase signal peptide is from 5762–5857; mature human α galactosidase A coding region is 5858–7036, ToMV virus coat protein and 3 UTR follows (SEQ ID NO: 13).

FIG. 13 shows SBS5-rGAL-12R TMV RNA begins at base 1; 126/183 reading frame begins at 69,3417 suppressible stop codon and ends at 4919.30K ORF begins at 4903 and ends at 5709. Human α galactosidase A RNA begins at 5703, complete (signal peptide and mature protein coding region) human α galactosidase A gene 5766–7037, TMV U5 virus coat protein and 3 UTR follows (SEQ ID NO:14).

DETAILED DESCRIPTION OF THE INVENTION

Figure 2:
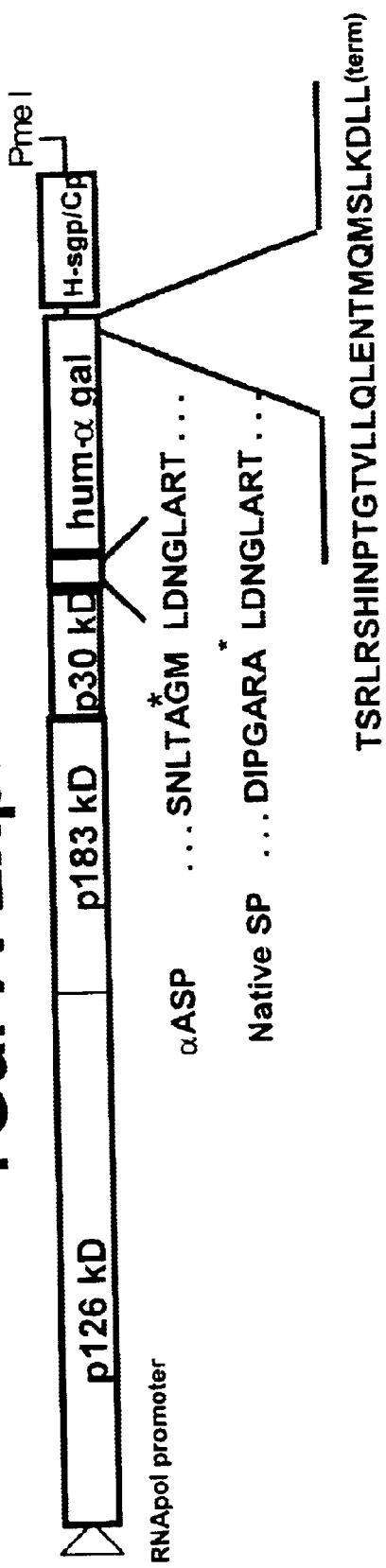
FIG. 2 shows a Tobamovirus expression vector containing the human α galactosidase gene or a variant of the gene (includes SEQ ID NOs: 1–3).

Gal-A is one of many proteins that require glycan site occupancy at N-linked sites to achieve proper folding and stability. The ability to successfully target the enzyme in Fabry patients is also likely to be glycosylation-dependent. This requirement presently limits the expression possibilities to eukaryotic cell types. Recombinant proteins synthesized in baculovirus and yeast expression systems are often hyperglycosylated and highly heterogeneous complicating the preparation of therapeutically effective glycoforms from these sources. The rGal-A synthesized in plants is a relatively homogeneous glycoform as analyzed by its SDS-PAGE electrophoretic mobility and comigrates with rGal-A produced purified from placenta (FIG. 2). The expression results (yield and purity) we have already presented are unprecedented in any eukaryote system for a glycosylated enzyme and are not likely to be achieved in the foreseeable future with transgenic plants or animals. "Crude" rGal-A from the leaf IF has a specific activity of over 1,000,000 U/mg of protein, whereas CHO, COS-1 and insect cell extracts and supernatants are maximally only 10–20,000 U/mg; (36,41,42).

Protein pharmaceuticals may vary over five orders of magnitude in unit value and be required in kg/year quantities. The example of Gaucher disease emphasizes the need progress in production phase research. Many additional heritable metabolic disorders, particularly those caused by dysfunctional lysosomal enzymes, might be treated by supplementation with exogenously produced enzymes. Enzyme replacement using macrophage-targeted human glucocerebrosidase has been shown to be extraordinarily beneficial for Gaucher patients. However, the cost of this treatment is very great. If the significant advances in clinical research are to be applied on a practical scale, new production technologies will be required to deliver bioproducts such as these to those in need at an affordable cost (43). No savings in Gaucher treatment costs were realized upon introduction of the recombinant CHO-cell product Cerezyme™ to replace the placental-derived Ceredase™. A significant reduction in cost requires fundamental changes in both the source of enzyme and process of purification.

While the existing treatment for Gaucher disease is safe and effective, there are potential contaminants derived from the source material that may pose serious risks. For the existing pharmaceutical products, these risks primarily include possibilities of contamination with human pathogenic viruses or peptides with potent hormonal activities such as human chorionic gonadotropin (44). These potential contaminants are not present in plant source material.

The main goal in selecting plants for expression of this protein is the potential for a radical reduction in costs. For the RNA-viral mediated synthesis of rGal-A and rGCB in plants, this is very likely to be achieved through the synergistic combination of three factors:

Complex crude extracts from various eukaryote cell production systems may be replaced with a plant leaf homogenate or IF fractions highly enriched in recombinant product.

Large-scale, sterile, cell fermentation systems and associated media, capitalization, and waste costs may be replaced with plant biomass. Production is then inexpensively scaled to the quantities desired.

The labor and time required to generate transgenic higher plants or animals may be replaced with a very rapid and simple plant transformation or plant viral transfection system.

Modern agriculture can supply a new generation of medicinal plants as a source of pharmaceuticals—a source that should be as inexpensive and readily available as our food, fiber, flavors and chemical feedstocks.

Experimental Design and Methods

Post-Translational Processing and Secretion. Protein secretion to the plant apoplast is through a default pathway. In our experience, addition of the rice α-amylase signal peptide (α-ASP) sequence at the N-terminus of several recombinant proteins is sufficient to direct the protein to the lumen of the ER in tobacco leaves. However, this is not likely to be a rate limiting step in protein accumulation and many native signal peptides may function equally well in plants. It would be most desirable to include few if any additional AA residues at the N terminus after processing. For this reason, we compared expression from the native signal peptide encoded in human Gal-A cDNA to that from the foreign α-ASP sequence.

Mutations in the carboxy-terminal domain of the Gal-A homodimer have profound effects on enzymatic activity. Several mutations occurring in individuals affected with Fabry disease map to this region. Some of these mutations have a dominant negative phenotype. When a peptide map was published on Gal-A purified from human lung, the authors noted the absence of the most carboxy-terminal predicted fragment and hypothesized the proteolytic removal of 26 or 28 AA from this region (39,40). Very recently Miyamura et al. published a study of the effects of carboxy-terminal truncations on enzymatic activity in transfected COS-1 cells (42). Between 2 and 17 AA residues were removed by introducing stop codons into a series of cDNA constructs. Relative enzyme activity, measured using 4-MUG as a substrate, first increased and then decreased as AA were removed. 12 and 17 AA constructs had no activity, while 11 was the same as wild type. A 4 AA construct yielded the highest activity at approximately 6.2× the full-length sequence. Because the precise AA sequence of the carboxy-terminus of the native human enzyme was never determined, there is insufficient information to interpret these results. The carboxy-terminal domain may affect the conformation of the active site either directly or indirectly through a proteolytic maturation step and/or assembly and subcellular localization of the active form. Furthermore, it is important to stress that it is the enzyme activity on galactose-terminal glycosphingolipids that is relevant to development of a therapeutic enzyme.

Plant proteins do not require N-linked oligosaccharides for correct sorting into vacuoles (35,37,38). Some vacuolar proteins (osmotin, thaumatin, chitinase-I, glucanase-I and a barley lectin), contain sorting information in a CTPP of 7 to 22 AA in length. For several of these proteins secreted isoforms are synthesized without a CTPP domain. In other cases, experimental deletion of the CTPP results in secretion of the recombinant protein to the IF (45–48). Sorting of Gal-A to the lysosome is likely to occur by the well-characterized mannose-6-phosphate receptor pathway in mammalian cells. We hypothesize that a redundant sorting signal may exist in this carboxy-domain that also serves to reduce enzymatic activity in the ER lumen, golgi and terns-golgi network. This signal appears to function in plant cells, presumably for vacuolar localization.

Scale-up Purification and Analysis. In order to evaluate the performance of larger scale process equipment, we designed and had built a custom basket centrifuge fixture for a laboratory low-speed centrifuge that has a capacity of approximately 1 kilogram leaf material. The sensitivity of the fluorescent 4-MUG enzyme assay allowed us to begin to evaluate enzyme purification from the leaf IF fraction using the construct rGal-A-SEKDEL. (This vector only yields approximately 1/50th the activity of rGal-A12-SEKDEL). Leaf tissue was transfected, harvested and infiltrated as described in Section B4 (Experimental Results). Galactosidase activity was stable in crude IF extracts and was bound to the hydrophobic interaction resin octyl sepharose, and eluted in a descending ammonium sulfate gradient. The lectin resin concanavalin-A sepharose was also effective, indicating the presence of at least one high mannose chain. The enzyme did not bind to a commercially available melibiose column (Sigma).

We have measured the enrichment provided by the affinity resin α-galactosylamine Sepharose with a C12 arm (49). Some or all of the three effective chromatography steps were combined as necessary with a size exclusion fractionation to yield highly purified enzyme(s). Because our current source of enzyme is so enriched (FIG. 2), and several of the published purification steps we have shown to be compatible with the plant IF extracts, we anticipate no problems in enzyme purification. Pure enzyme preparations were shipped to the laboratory of Drs. Roscoe Brady and Gary Murray for evaluation of enzyme activity with $^{14}C$-galactose-labeled ceramide trihexoside. These colleagues were responsible for the development of the therapeutically effective glycoform of glucocerebrosidase used to treat Gaucher disease. For this purpose, Biosource has a five year Cooperative Research and Development Agreement with the National Institute of Neurological Disorders and Stroke, NIH, entitled "Human Metabolic Enzymes Produced in Plants," signed Mar. 15, 1994.

We scaled up the purification of up to four candidate therapeutic enzymes as necessary in our indoor greenhouses. In our initial experiment (Table 1), 38 and 48 percent of the total rGal-A activity was recovered upon the first infiltration and centrifugation treatment (Construct rGal-A12-SEKDEL) for a yield of >50 mg of enzyme per kilogram of leaf material. Experience with the extraction of glucocerebrosidase from the IF indicates that additional enzyme is recovered in a second treatment. In these experiments one leaf was collected for each sample from each of two plants. There was considerable plant to plant variation in the level of enzyme activity (Table 1). We analyzed more carefully the accumulation of enzyme activity over time post-inoculation to optimize yields. Our facilities are more than sufficient to provide the 1 kilogram quantities of biomass necessary to purify nanomoles of enzyme for the following sequence and structural work. Sequence analysis and MALDI-TOF molecular weight determination was performed as a commercial service by Commonwealth Biotechnotogies, Inc. N-terminal sequence is by the automated Edman degradation. C-terminal sequence is by carboxypeptidase digestion followed with amino acid analysis.

Full-Scale Bioprocess Pilot Plant

Macroextraction. Large-scale maceration of tissue was accomplished by a 65 hp Rietz disintegrator mill. The macerated tissue was then separated into a "green juice" fraction and a fiber fraction in a Rietz screw press. The fiber fraction was dried in a Cardwell drier. The "green juice" was then pH adjusted and heated in a dual plate-and-frame heat exchanger system with adjustable holding tube. The process of pH adjustment and heating causes the precipitation of the F1 protein complex. The protein was then clarified in a 40 hp. Westphalia SA-40 disk stack centrifuge capable of clarification of "green juice" at greater than 20 gallons per minute (GPM).

Downstream Processing. The concentrate was then pumped to Clean Room 1 that houses the primary ultrafiltration (UF) equipment. This equipment was fitted with over 1000 sq. ft. of spiral wound membranes. Typically, the UF was equipped with 100,000 kDa cut-off membranes. Virus particles are recovered in the retentate. Lower molecular weight proteins are recovered in the permeate. The permeate was fractionated by a second UF system fitted with appropriate molecular weight cut-off membranes. The retentate was processed in Clean Room 2. Virus was recovered by polyethylene glycol (PEG) precipitation and centrifugation in two Sharples vertical bowl centrifuges. Final purification of soluble proteins and peptides was accomplished on a series of chromatography systems.

Additional Facilities. The facility has other major unit processes available for the recovery and purification of plant fractions. There are two Alar diatomaceous earth, rotary vacuum filters. One of the filters was in an explosion proof area of the pilot plant that can be used for solvent extraction. The solvent extraction facility also has a biphasic solvent extractor and high efficiency distillation column. Extensive tankage was available both indoors and outdoors. Pumps, filters and other process equipment are available at the facility, allowing a large margin of flexibility while developing new processes.

Full-Scale Pilot Plant Implementation. The Bioprocess Facility has excellent supporting infrastructure. The 900 square foot laboratory was equipped with all the basic tools for biochemical and protein analyses including: electrophoresis, gel filtration, HPLC, spectrophotometry, basic chromatography, chemical-analysis, and sample preparation and preservation. The full scale pilot plant has approximately 15,000 square feet of additional floor space for expansion including a high bay tower. External solvent tanks are placed in diked enclosures. Two rapid recovery, high pressure (up to 600 psi) steam generators and a large twin screw, oilless compressor are on site. A complete shop and maintenance facility was present along with walk-in cold room and walk-in freezer. Additional equipment includes a ceramic micro filtration system, a spray dryer and an array of tanks, pumps, filters, heat exchangers, and agitators.

Process equipment was fabricated and modified by a group of skilled vendors and craftsmen capable of fabricating specialized equipment designed by the company, and has excellent field experience working in large scale operations. The proposed infiltration, centrifugation, vacuum filtration and downstream processes described below are diagrammed in a simplified single-line form in FIG. 5. This diagram was derived from the existing configuration of the plant (Appendix 2).

Infiltration System. Vacuum infiltration can be accomplished in the field or at the processing facility. Development experiments determine the necessity to infiltrate the material in the field. A vacuum tank was used as the receiver for the plant tissue after harvest by the tobacco cutter. The tissue was conveyed into a trailer-mounted tank capable of full vacuum and slurried into an infiltration buffer. The Owensboro facility has a trailer capable of carrying approximately 18,000 lb. This will translated into approximately 1,000 gallons per trip to the field. The trailer was fitted with a 2,000 gallon tank capable of full volume and evacuated by a gasoline driven vacuum pump. In harvests from 1991–1994, it was the goal of the team to have harvested biomass at the processing facility in less than 1 hour after cutting. If the tissue can be held for approximately one hour without significant loss of enzyme activity, the biomass can be brought from the field in the conventional wagon and infiltrated at the processing facility. Several large, full vacuum tanks can be employed at the facility to increase the total throughput of the plant. Two large-scale vacuum pump systems in the plant that are currently associated with the Alar rotary vacuum filters can be used for the vacuum infiltration process step.

Basket Centrifugation. The full-scale basket-type centrifuge was a discontinuous batch-type system. Leaf tissue can be slurried in, dewatered as a batch, then a scraper system discharges the solids to a bottom dump. Large leaves and pieces of tissue can be handled in this manner. The potential of placing a vacuum system on the discharge side of the centrifuge was also be investigated. The centrifuge was a hydraulically driven conventional basket centrifuge with a bottom discharge and bowl dimension of 48 inches in diameter and a depth of 30 inches. Optimum loadings of the centrifuge in fill-scale was determined the throughput and cycle times of this process step.

Vacuum Extraction. Vacuum extraction can be accomplished in large-scale by a web or belt-type vacuum filter system common in the food ingredient business. The "in-plant" vacuum systems could also be adapted to operate this type of filter. The plant tissue can be placed on this type of filter before or after the centrifugation step. Some damage of the biomass was anticipated during the scraper mediated discharge of the basket centrifuge. The discharged material was analyzed for the presence of intracellular components and their effect on enzyme activity, recovery and separation. These data determined the position of the vacuum filtration step in the process flow.

Downstream Processing. The initial UF separation was accomplished by an Alfa-Laval custom UF system consisting of six modular housings each containing either three 12 inch spiral wound membranes (Amicon type). or one standard 38 inch module. This yields a UF system with between 740 and 1140 square feet of membrane area of typical spiral wound configuration. The ability to interchange housings and replace housings by spool pieces gives the system great flexibility in large-scale process development. This system was housed in Clean Room # 1. This room is 14×18 ft, and is under positive pressure, HEPA-filtered air. A second UF system was available in Clean Room #1. This smaller system, built by Separations Equipment Technology (SETEC), has the capacity for 320 square feet of spiral wound membrane. This system was employed for the second separation and diafiltration. It was designed for automatic diafiltration. Clean Room # 2 is equipped with a Pharmacia Streamline fluid bed gel filtration system equipped with UV and refractive index monitoring equipment. This unit was available for chromatography steps.

Figure 11:
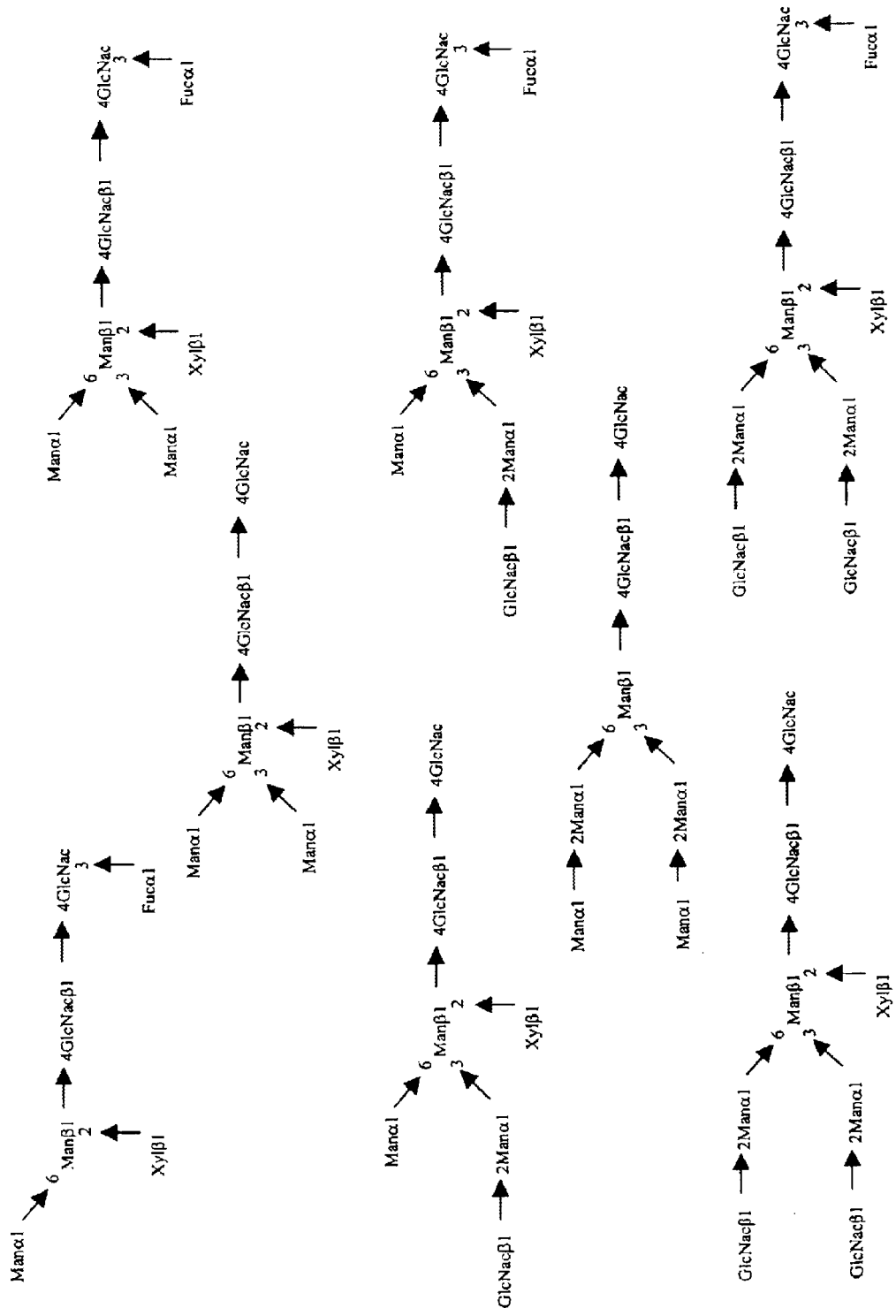
FIG. 11 shows different glycosylation structures of α galactosidase.

An antiserum specific for these xylose- and fucose-containing complex glycans was especially useful in developing an ELISA assay to follow enzymatic deglycosylation. Large quantities of purified enzyme facilitate definitive determination of glycosylation structure and if necessary provide adequate rGal-A to use as substrate for enzymatic deglycosylation reactions. Using Gal-A knockout mice in the laboratory of Dr. Brady at NIH was an important genetic tool in developing a therapeutically effective glycoform. We use our transfected plants as a convenient source of recombinant enzyme for glycan analysis. Glycoforms are shown in FIG. 11.

Plants as a Source of Recombinant Pharmaceutical Proteins. A number of genetic tools have been developed during the last decade for the expression of foreign genes in plants. In addition to various antibody molecules (21–23), the accumulation of serum proteins (24) and candidate vaccine products (25–28) has been described in the leaves and other tissues of whole plants. We increased the attainable expression levels through the use of chimeric RNA viruses. For production of specific proteins, transient expression of foreign genes in plants using virus-based vectors has several advantages. These chimeric viruses move quickly from an initial infection site and deliver the recombinant gene to essentially all somatic cells of the plant. The gene vectors are premier analytical tools because they allow both high level expression and brief cycles of protein modification and testing. A permissive host provides high levels of expression and may be used for rapid, large-scale recombinant protein production in whole plants.

We validated the performance of plant-based expression systems for the production of recombinant proteins and peptides of pharmaceutical significance. In two weeks post-inoculation, the ribosome inactivating enzyme α-trichosanthin was over-produced in plants to 2% of the total soluble protein and had the same specific activity as the enzyme from the native source (29). Because these products can be obtained from a non-sterile, low input, renewable and easily scalable source, the costs of synthesis in plants are negligible. We confirmed the performance and containment of the vectors in four field trials (1991, 1994, 1995, 1996).

The vectors of the invention are based on chimeras between the 6.4 kb single-stranded RNA genome of tobacco mosaic virus (TMV) and other members of the tobamovirus group. Most of the TMV genome encodes overlapping reading frames required for replication and transcription (FIG. 1A). These are located at the 5' end of the virus and translated from genomic RNA yielding proteins of 126 and 183 kDa. Expression of the internal genes was controlled by different promoters on the minus-sense RNA that direct synthesis of 3'-coterminal subgenomic mnRNAs produced during replication. The 30 kDa protein, which was required for the virus to move from cell to cell, was produced early and in relatively low amounts, whereas the 17.5 kDa coat protein was produced late and usually as the most abundant protein in infected cells. Largely because of the strength of the coat protein subgenomic promoter, during peak protein synthesis the coat protein can be produced at up to 70% of the total rate of cellular protein synthesis without appreciably reducing host protein synthesis (30).

The entire cDNA of the TMV genome was cloned behind a bacterial phage promoter in an $E.$ $coli$ plasmid. Precise replicas of the virion RNA can be produced in vitro with RNA polymerase and dinucleotide cap, $m^7GpppG$. This not only allows manipulation of the viral genome for reverse genetics, but it also allows manipulation of the virus into a gene transfer vector. Subgenomic promoters from divergent viral strains can be added to the genome to direct the expression of foreign genes. Enormous quantities of MRNA are synthesized and delivered directly from the cytoplasm to the ribosome. TMV-based transient vectors offer significant advantages over integration of genes into plant chromosomes. By altering the molecular exclusion limits of the cellular junctions between adjacent plant cells, the vector invades virtually every cell of the plant during a period of 2 weeks post-inoculation. For many gene products, the recombinant protein accumulates to several percent of the total protein during this brief period of time. In contrast, it was very time consuming and labor intensive to generate, select, and breed transgenic plants for recombinant protein production. Many of these selections were culled because of poor expression due to position effects or gene silencing phenomena. In many more lines, the levels of product accumulation was too low for development of a viable commercial process.

EXAMPLE 1

We have established that a recombinant human lysosomal enzyme (rGCB) synthesized in transgenic tobacco has comparable activity to the same enzyme isolated from other native and recombinant sources. We also investigated the feasibility and economic advantages of purifying large quantities of active rGCB from plants. We designed and fabricated laboratory equipment that enabled us to optimize the key initial steps of a purification process in the laboratory using kilogram quantities of biomass from our greenhouses. We standardized a series of assays for secretory and intracellular marker enzymes in addition to rGCB assays that allowed us to monitor both lab and field expression as well as the purification process. Leaf tissue was infiltrated with a suitable extraction buffer while submerged in a large vacuum chamber, allowing the solution to reach the leaf intercellular fluid containing rGCB. The IF fraction was recovered by centrifugation in a custom collection chamber and "basket" centrifuge rotor compatible with a conventional Beckman J2-21 spindle. rGCB was trapped from the dilute IF solution by expanded bed adsorption chromatography using a hydrophobic resin and eluted with polyethylene glycol. A second ion exchange chromatography step was implemented for an overall yield of 1.7 mg/kg at 41% purity to this stage. These procedures were then scaled-up to 100 kg during several pilot-process experiments in a field trial using analogous industrial bioprocess equipment. These results are summarized in the table below. Three lots of rGCB were further purified by RP-HPLC and used for carbohydrate profiling and composition analysis. In NMR experiments we-confirmed that the GCB from the plant IF contains an N-linked glycan previously reported to occur in glycoproteins isolated from plant seeds and tissue cultures. This type of chain contains the plant-specific carbohydrate linkages of α 1–2 xylose and β 1–3 fucose on the trimannosyl core.

Making Transgenic Tobacco Plants to Produce Glucocerebrosidase

Several founder plant lines for genetically stable expression of rGCB were generated and characterized. Under greenhouse conditions individual plants accumulate rGCB to at least 1.3% of the total protein in the leaf intercellular fluid as estimated from enzymatic assays. This represents a 50-fold enrichment relative to the crude lysosomal fraction of placental extracts used as the starting material for the product Ceredase™.

Figure 14:
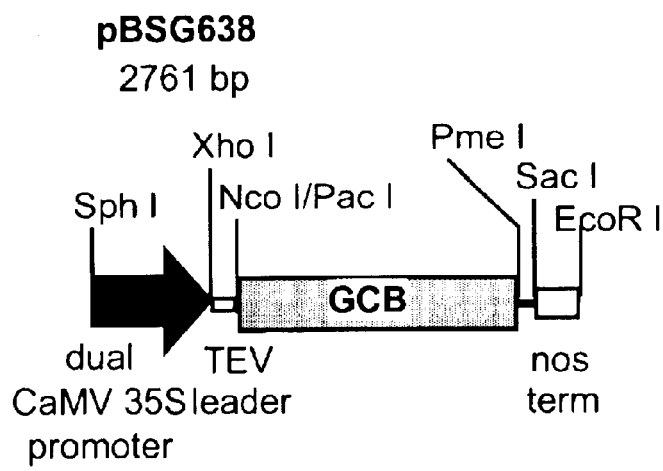
FIG. 14 shows transgenic vector pBSG638 for rGCB expression.
Figure 15:
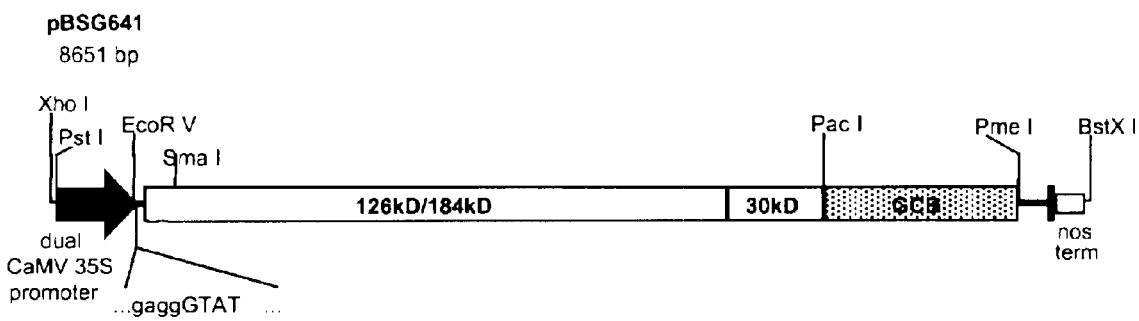
FIG. 15 shows viral vector pBSG641 for rGCB expression.

Transgenic Tobacco Leaves Express Moderate Levels of rGCB. We combined a dual promoter from Cauliflower Mosaic Virus (35S), a translational enhancer from Tobacco Etch Virus and a polyadenylation region from the nopaline synthetase gene of Agrobacterium tumefaciens with the native human GCB cDNA to create plasmid pBSG638 (33; FIG. 14). These expression elements are widely used to provide the highest possible constitutive expression of nuclear encoded genes. Depending on the nature of individual proteins, these vectors can be used to accumulate moderate levels of recombinant proteins in most tissues of many plant species.

Using a standard Agrobacterium-mediated transformation method, we regenerated 93 independent kanamycin-resistant transformants from leaf discs of four different tobacco cultivars (the T0 generation). In Western blots of total protein extracts, cross-reacting antigen was detected in 46 of these T0 individuals with antibody raised against human glucocerebrosidase. Specificity of the plant-expressed recombinant enzyme was confirmed by hydrolysis of $^{14}$C-radiolabeled glucosylceramide.

Leaf Disc Transformation with Agrobacterium Tumefaciens (59, 60, 61)

Method:
1) Transform the T-DNA plasmid into A.t. LBA4404 selecting for the bacterial Ab$^R$ gene (generally Km at 100 ug/ml).
2) Pick a single colony into YEB medium plus antibiotic and grow at 28° C. overnight (to saturation; often takes a little longer than overnight).
3) Take aseptic or surface-sterilized Nicotiana tabacum (MD609, Xanthi, SR1, Samsun) leaves, remove midrib and cut into leaf "chunks" ~1 cm$^2$.
4) With sterile forceps, dip (submerge) the leaf disc into the Agrobacterium suspension.
→ Placing the bacterial culture into a small petri dish is convenient.
5) Remove the leaf disc from the Agrobacterium and place the disc on regeneration medium. Place the discs so that the underside of the leaf is up. (They seem to do better this way, perhaps because of better gas transfer.)
→ I use needle-nose forceps to handle the discs, thus introducing small puncture wounds into which Agrobacterium can infect; small wounds are good, major damage (e.g., crushing) to the disc is bad.
6) Seal plate containing discs with Parafilm® and incubate at 25–28° C., preferably in light with a yellow filter to inhibit UV degradation of the medium.
7) After 2 days co-incubation, transfer the leaf discs to selective plates (regeneration medium plus 500 ug/ml Cefotaxime).
8) After 2 more days, transfer discs to regeneration medium plus 500 ug/ml cefotaxime and 100 ug/ml kanamycin
9) When normal-looking shoots appear, excise them, taking care not to excise any callus, and place in rooting medium.
→ Callus on the end of the stem generally prevents rooting, and could lead to a chimeric set of shoots.
→ The lower % agar makes it easier to wash the agar off the roots when transferring to soil.
→ If there is time, it is a good practice (when the plants are rooted and growing) to cut the shoots off and re-root them. Escapes will generally not root on Km medium.
10) When roots first appear, remove plantlets, wash agar from the roots and plant in soil medium in small pots. Cover pots with a plastic bag for the first 5 days or so to retain humidity and reduce transplantation shock.

1 Liter of Regeneration Medium contains:
MS Salts
30 g sucrose
1 ml of 0.5 mg/ml nicotinic acid
1 ml of 0.5 mg/ml pyridoxine HCl
2 ml of 0.5 mg/ml thiamine HCl
2 ml of 50 mg/ml inositol
1.5 ml of 0.1 mg/ml IAA
5.0 ml of 1.0 mg/ml 2-IP-2-iminopurine
8 g of agar, pH 6.0

1 Liter of Rooting Medium contains:
½×MS Salts
10 g sucrose
2 ml of 0.1 mg/ml IAA
8 g agar, pH 5.7

A deposit at ATCC under the Budapest treaty was made on Jul. 25, 2000 of seed from Nicotiana benthamiana MD609, Accession No. PTA-2258.

According to these expression results the rGCB positive transformants were ranked into moderate (A), low (B) and negligible (C) activity groups (Table 2).

TABLE 2

EXPRESSION OF rGCB IN THE T0 GENERATION.

| Group | Number of Individuals | Specific Activity Units/mg |
|---|---|---|
| A | 13 | 130–390 |
| B | 20 | 70–130 |
| C | 13 | 24–68 |
| Controls | 8 | 0–10 |

Specific Activity is based on hydrolysis of [14C]-glucosylceramide (Units=nmol/hr).

Plant rGCB is Similar to Macrophage-Targeted Glucocerebrosidase. We found reaction conditions to preferentially inhibit rGCB enzyme activity in the presence of plant glucosidases using the suicide substrate conduritol B-epoxide (CBE). Total glucosidase activity, and rGCB activity were measured by hydrolysis of the fluorescent substrate 4-methylumbelliferylglucopyranoside (4-MUG) with and without CBE. Total protein was determined by the method of Bradford. Detergents are necessary to solubilize and stabilize activity of this membrane-associated enzyme. Using a small scale (~100 mg fresh weight) extraction procedure, several detergents were compared for yield of enzyme activity and purity (including; IGEPAL CA-630, Tween-20, Tween-80, Triton X-100, Triton X-114, CHAPS, taurocholic acid, cholic acid, deoxycholate and taurodeoxycholate). Buffer without detergent, deoxycholate, taurocholate and cholate below their critical micelle concentrations (CMC) (0.1%) yielded low units of rGCB. All of the other detergents gave comparable specific activity and yields of total activity with Tween-80 yielding slightly higher activity. The dialyzable bile salt, sodium taurocholate and the lower CMC detergent Tween-80 were compared at a range of concentrations (0.1–1% and 0.001–1%, respectively). Tween-80 at 0.15% and taurocholate at 0.5% gave the best yield and purity.

A number of chromatography steps were evaluated for purification of rGCB from total homogenates (Table 1). As is the case for the native placental enzyme, hydrophobic resins provide the most significant purification gains. Gel filtration, Con A Sepharose and affinity chromatography also worked very well, but some of these approaches may be impractical on a large scale. Both anion and cation chromatography may prove useful, but the ideal buffer conditions for stabilization of enzyme activity remain to be determined.

TABLE 1

SUMMARY OF CHROMATOGRAPHY RESULTS

| Column Matrix | Type | Results |
|---|---|---|
| Octyl Sepharose 4 FF | Hydrophobic | + |
| Phenyl Sepharose HP | Hydrophobic | + |
| Phenyl Sepharose 6 FF | Hydrophobic | + |
| Butyl Sepharose 4 FF | Hydrophobic | – |
| Alkyl Superose | Hydrophobic | – |
| SP Sepharose FF | Strong Cation | +/-- |
| Q Sepharose FF | Strong Anion | +/-- |
| Con A Sepharose | Lectin Affinity | +/– |
| NHS-Activated Sepharose HP | Antibody Affinity | + |
| Sephacryl S-100 HR | Gel Filtration | + |

(+) Effective increase in Specific Activity; (+/–) Needs enzyme activity stabilized; (+/–) Variable results; (–) Poor binding.

The post-translational processing of native glucocerebrosidase (GCR) in human cells is complex. Two primary translation products are derived from two in-phase start codons. These precursors, a 2:1 mixture of 60 kDa and 57 kDa proteins, are proteolytically processed to 55 kDa as they pass into the lumen of the ER. High mannose and complex glycans are subsequently added in the ER and Golgi compartments to yield 62 and 66 kDa glycoforms. Finally, exoglycosidases generate a mature 59 kDa lysosomal enzyme. Recall that glycosylation is required for both enzymatic activity and lysosomal targeting of transfused enzyme. Sialic acid, galactose, and N-acetylglucosamine residues are enzymatically removed in vitro by the sequential action of glycosidases to prepare glucocerebrosidase for therapy. The core pathway for biosynthesis and processing of N-linked complex glycans in plants appears identical to that found in animals. There are three known differences which occur later in the pathway. Sialic acid is not reported in complex glycans from plants, and the α1–3 fucose and β1–2 xylose linkages are unique (34). As. analyzed by SDS/PAGE, rGCB has an apparent molecular weight of 59 kDa, and comigrates with the mannose-terminal therapeutic glycoform. We have not yet detected a significant shift in mobility upon treatment with glycosidases (PNGase F, Endo H, α1–3 fucosidase) in our preliminary glycosylation analysis (FIG. 2). However, the enzyme has an apparent molecular weight increase of 4 kDa over the proteolytically processed and unglycosylated form (55 kDa) and must be glycosylated for activity. Additional digestions are in progress with a more extensive set of endo- and exoglycosidases and known plant glycoprotein controls. N-Glycosidase A is reported to hydrolyze all types of N-glycan chains from glycopeptides and glycoproteins.

Figure 3:
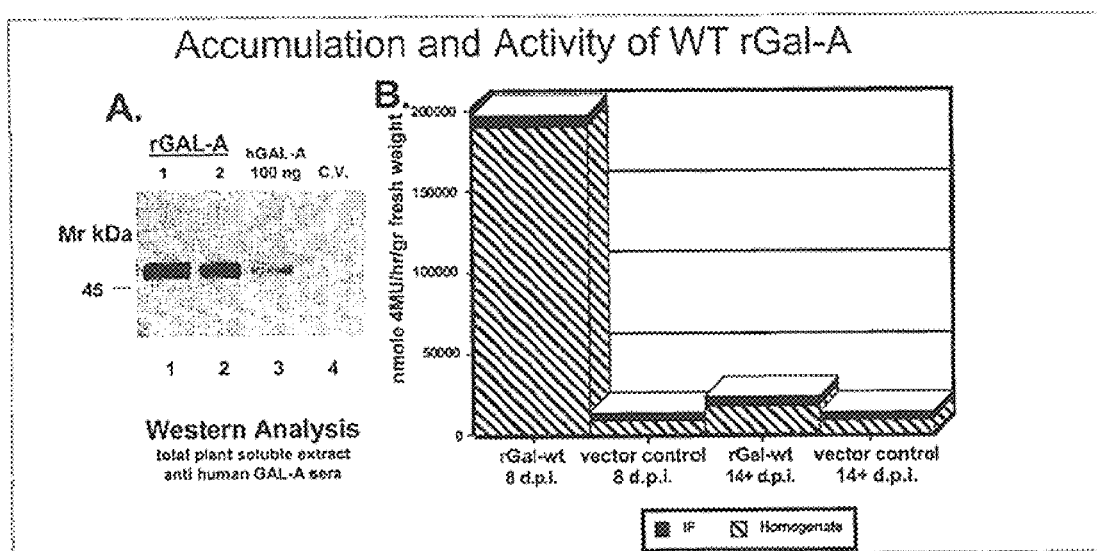
FIG. 3A shows accumulation by Western Analysis of total plant soluble extract anti human GAL-A sera.
FIG. 3B shows activity of WT rGAL-A at 8 and 14+ days post inoculation of the plant host with a viral vector.
Figure 4:
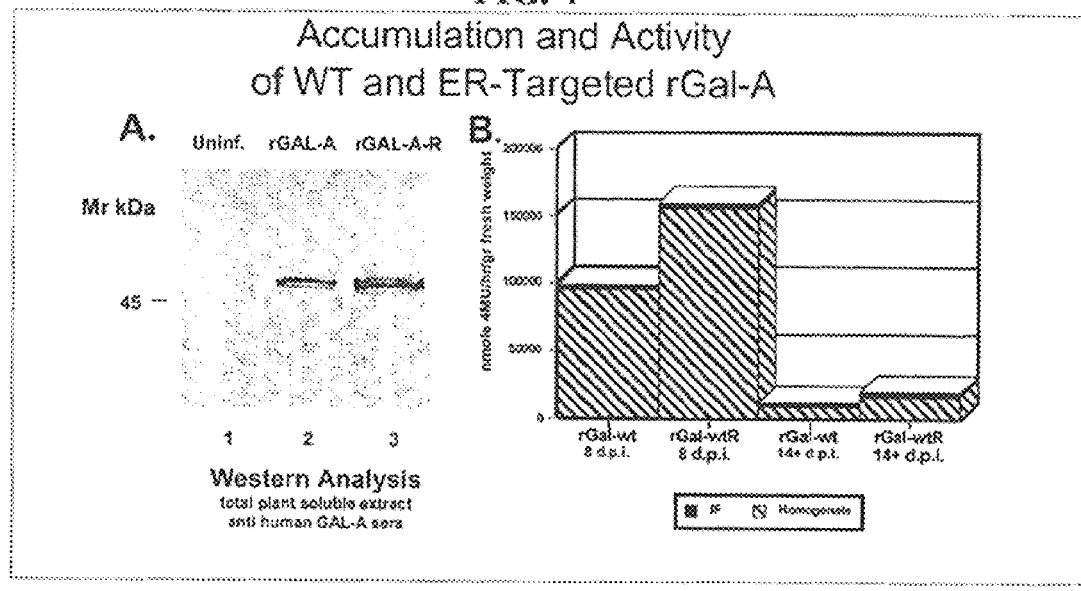
FIG. 4A shows Western blot analysis of total plant soluble extract anti human GAL-A sera
FIG. 4B shows activity of WT rGAL-wt and rGAL-wtR at 8 and 14+ days post inoculation of the plant host with a viral vector.
Figure 6:
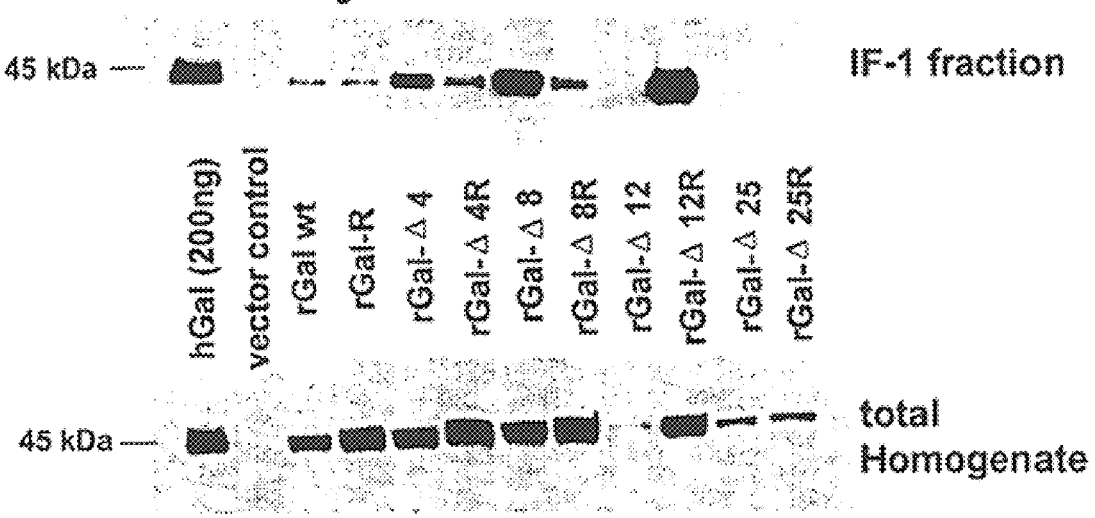
FIG. 6 shows western blot analysis of the accumulation of 10. carboxy-modified rGAL-A variants from interstitial fluid and from total plant homogenate.
Figure 7:
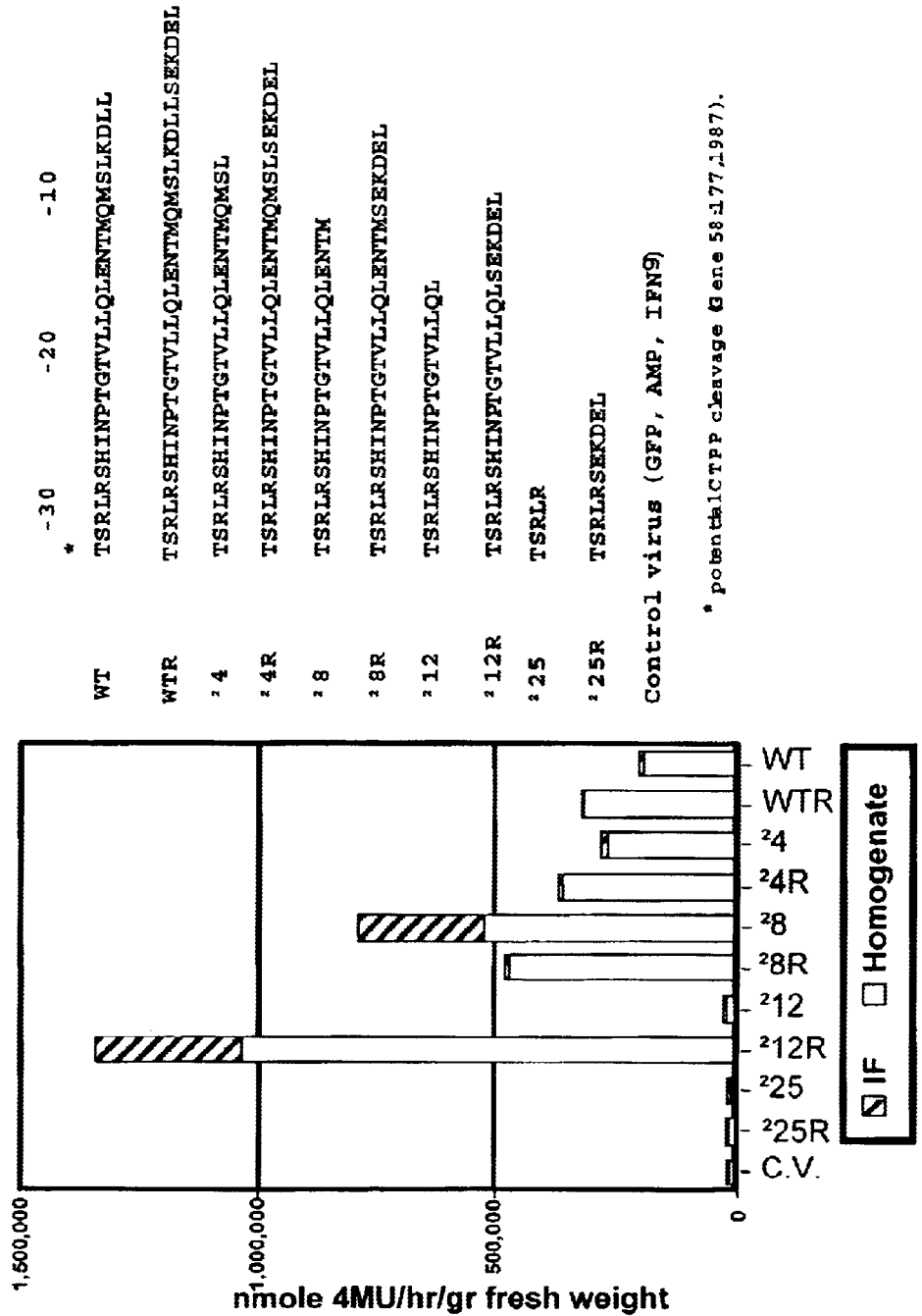
FIG. 7 shows a comparison of enzymatic activity of the 10 carboxy-modified rGAL-A variants.
Figure 8:
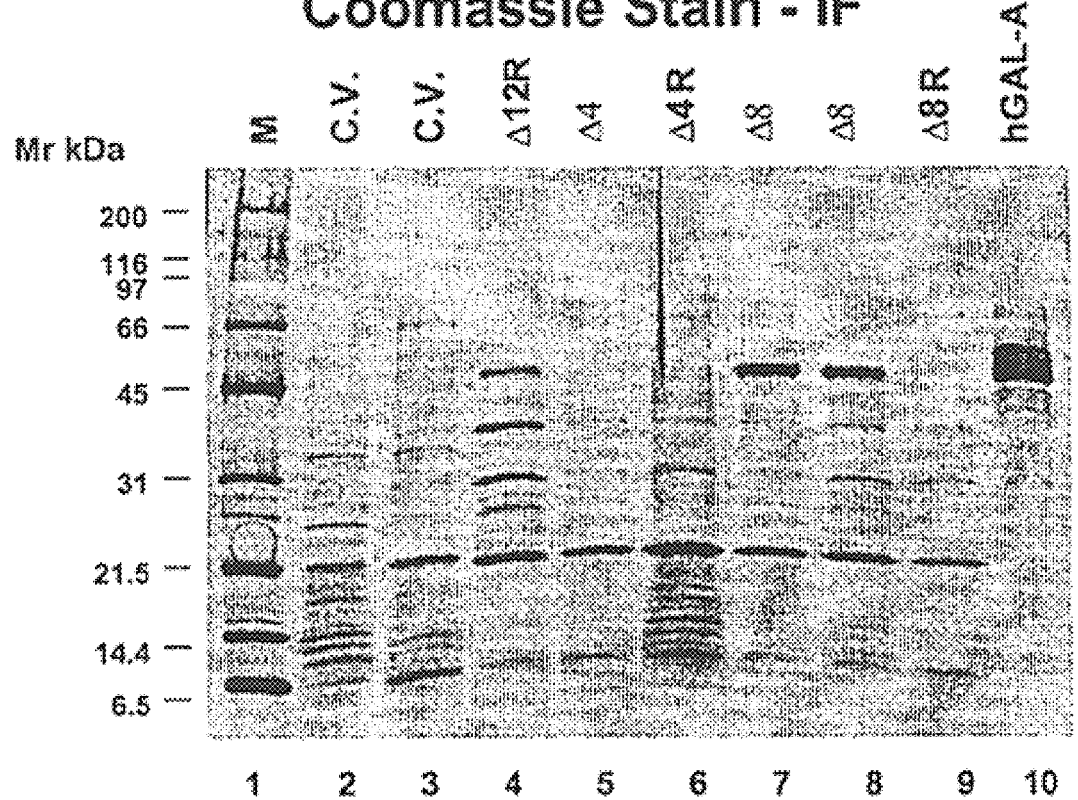
FIG. 8 shows a Coomassie blue stained electrophoresis gel separation of carboxy-modified rGAL-A variants and controls.
Figure 9:
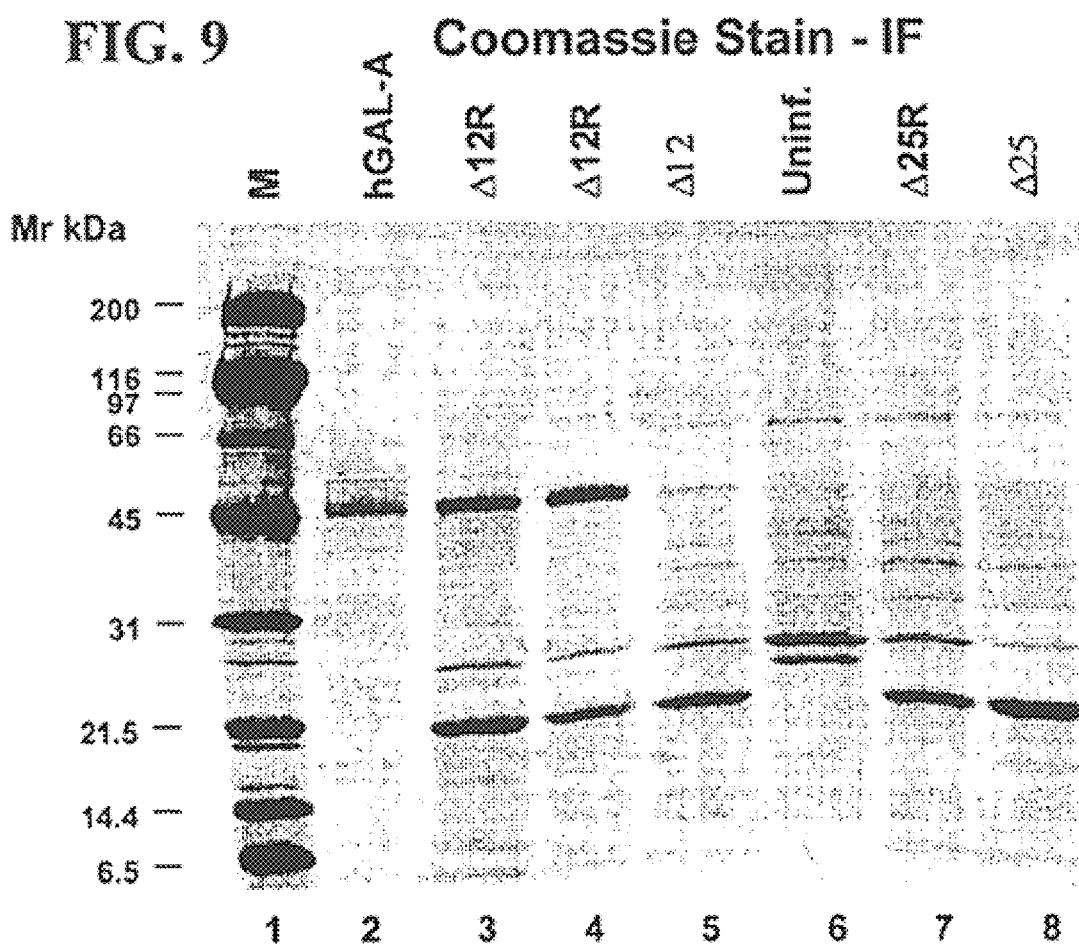
FIG. 9 shows a Coomassie blue stained electrophoresis gel separation of carboxy-modified rGAL-A variants and controls.
Figure 10:
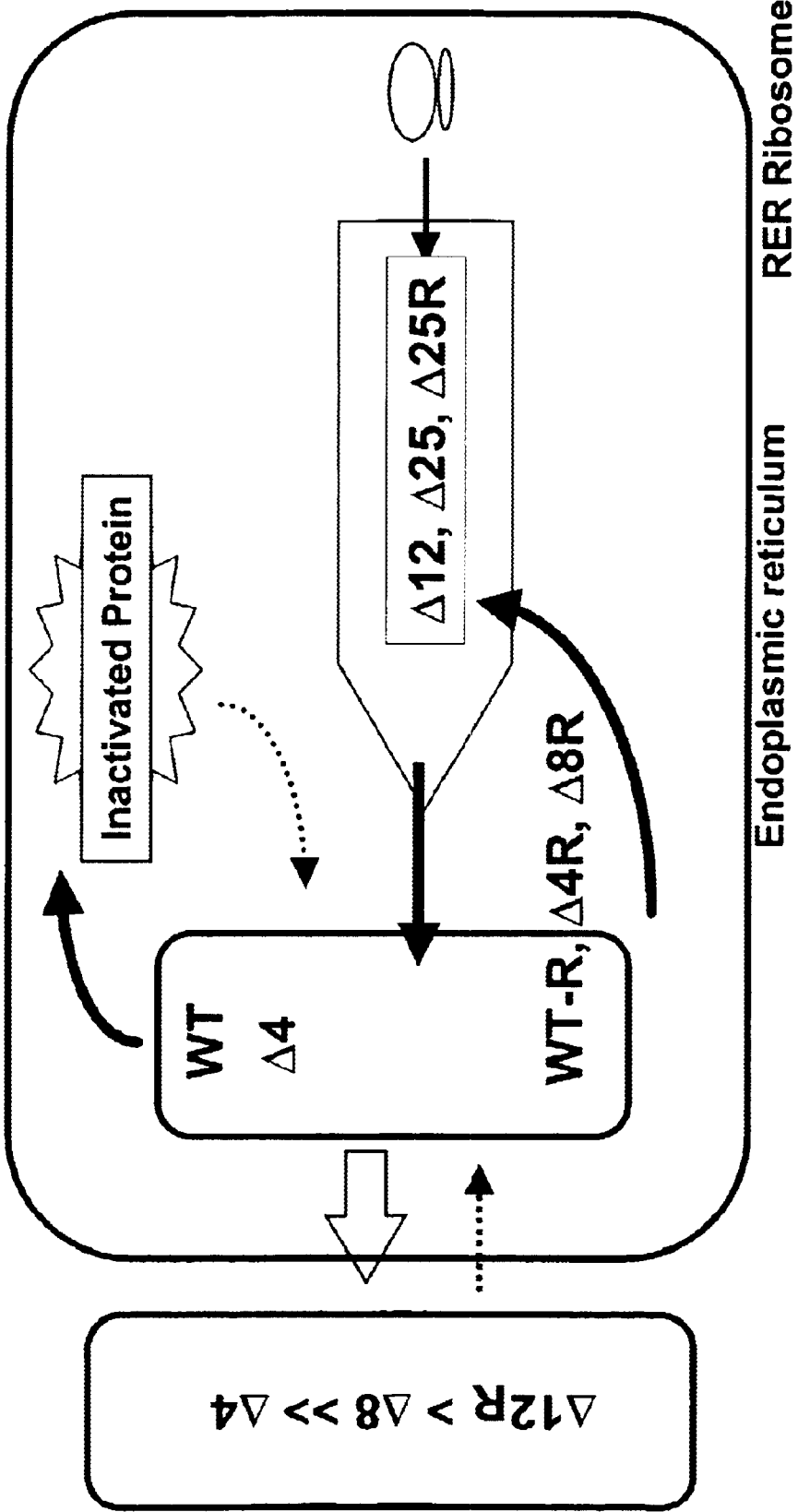
FIG. 10 shows a schematic representation of rGAL-A secretion from the endoplasmic reticulum to the apoplast.

The signal peptide of rGCB is processed at the correct site. A very small quantity of protein was prepared for sequence analysis by purification through Phenyl-Sepharose, ConA-Sepharose and RP-HPLC to produce a single band on SDS-PAGE comigrating with authentic glucocerebrosidase. The sequence obtained was consistent with the known sequence of processed GCR (FIG. 3). In this particular analysis, the first two positions were not resolved because some degradation occurred during sample preparation. Correct proteolytic cleavage of a signal peptide is also confirmed for a mouse antibody light chain molecule expressed in tobacco leaves (35).

STRUCTURE OF THE N-TERMINUS OF rGCB

N-terminal Amino Acid Sequence

| | |
|---|---|
| X X P X I P K S F G Y | rGCB from tobacco (SEQ ID NO:15) |
| A R P C I P K S F G Y | GCR human (SEQ ID NO:16) |

Plant rGCB Accumulates in the Leaf Intercellular Fluid. We localized rGCB to the intercellular fluid of the leaf using the following simple experimental design. Leaves were removed from the plant at the petiole and slit down the midrib into two equal halves. To obtain a total cellular homogenate, one group of half-leaves was ground in the presence of 4 volumes of detergent extraction buffer (100 mM potassium phosphate pH 6, 5 mM EDTA, 10 mM β-mercaptoethanol and 0.5% w/v sodium taurocholate) with a mortar and pestle. To recover the IF, the same enzyme extraction buffer was infiltrated into the opposing group of half-leaves by submerging the tissue and applying moderate vacuum pressure. After draining off excess buffer, the undisrupted half-leaves were rolled gently in Parafilm, placed in disposable tubes and the IF collected by low-speed centrifugation. The IF fraction is quite clear and non pigmented and can be applied directly to Phenyl Sepharose hydrophobic resin.

The results of a typical experiment are shown in Table 2. The increase in specific activity corresponds to a similar increase in the amount of cross-reacting material observed in a Western blot and is therefore not an artifact of the enzyme assay in the different fractions. Furthermore, rGCB activity was very stable in crude extracts using this particular detergent buffer. The increase in specific activity can therefore be attributed to an enrichment of rGCB in the IF relative to the whole cell homogenate. The actual concentration of rGCB in the IF is likely to be much higher, because PAGE analysis of the IF fraction shows some contamination with known cytoplasmic markers. The highest specific activity we have measured in an IF sample is 20,000 U/mg. If we assume rGCB has the same specific activity as the human enzyme ($1.5 \times 10^6$ U/mg), this corresponds to 1.3% of the IF protein obtained by this method.

TABLE 2

LOCALIZATION OF rGCB TO THE INTERCELLULAR FLUID

| Sample | Fresh Weight (gr) | Total Volume (ml) | Protein Conc. (mg/ml) | Total Protein (mg) | Protein Yield (mg/gr) | rGCB Conc. (U/ml) | Total rGCB (U) | rGCB Yield (U/gr) | Specific Activity (U/mg) | % Recovery rGCB in IF | X-Fold Purification |
|---|---|---|---|---|---|---|---|---|---|---|---|
| Intercellular Fluid | 2.48 | 1.9 | 0.24 | 0.45 | 0.18 | 720 | 1368 | 552 | 3007 | 22 | 18 |
| Homogenate | 2.08 | 8.1 | 3.89 | 31.48 | 15.13 | 653 | 5289 | 2543 | 168 | | |

Specific activity is based on the hydrolysis of 4-MUG inhibited by 0.5 mM CBE. Units (U)=nmol/hr. Because the amount (in nanograms) of cross reacting material observed in a quantitative Western blot corresponds within experimental error to the amount (in nanograms) of enzyme calculated on the basis of activity, we believe the plant rGCB was synthesized with high specific activity. This was a very important and favorable indirect estimate of specific activity. The enzyme was purified to homogeneity to measure more precisely the actual specific activity.

High Levels of rGCB Expression in Leaf Tissue Induce Gene Silencing. The T0 individuals described in Table 2 are by definition hemizygous. They contain various loci generated from independent insertion events, having no corresponding insert on the homologous chromosome. The thirteen T0 individuals from Group A were self-pollinated and assayed for levels of enzyme expression in the T1 generation in order to analyze the effects of gene dosage (homozygotes versus hemizygotes) and to identify candidate T1 families for future seed increase. Kanamycin-resistant transgenic plants were randomly selected from segregating families and analyzed for rGCB expression. The number of probable loci was estimated by chi-square analysis of the linked kanamycin-resistant phenotype at>95% confidence level. There are several T1 families with a heritable mean rGCB activity in the range of 200–300 U/mg (nmol 4-MUG hydrolyzed per hour) in the total homogenates that we have selected for further production of the enzyme (Table 3).

TABLE 3

EXPRESSION OF rGCB IN THE T1 GENERATION

| Tobacco Cultivar | T1 Family | Number of Loci | Mean Specific Activity Units/mg | Standard Error | Number of Individuals |
|---|---|---|---|---|---|
| Samsun | 963 | 2 | 294 | 25 | 23 |
| Samsun | 881 | 1 | 242 | 22 | 16 |
| MD609 | 920 | 1 | 205 | 15 | 38 |
| Xanthi | 902 | 1 | 202 | 17 | 5 |
| Samsun | 883 | 1 | 201 | 18 | 13 |
| Xanthi | 832 | 1 | 195 | 18 | 9 |
| SR1 | 826 | 1 | 184 | 16 | 40 |
| SR1 | 834 | 1 | 145 | 9 | 32 |
| Xanthi | 851 | 1 | 140 | 15 | 5 |
| Samsun | 837 | 1 | 129 | 16 | 8 |
| Xanthi | 831 | 1 | 114 | 21 | 10 |
| Xanthi | 833 | 1 | 107 | 12 | 5 |
| Xanthi | 807 | 1 to 2 | 87 | 12 | 9 |
| Controls | | | 40 | 8 | 20 |

However, of 235 T1 plants analyzed, the single individual having the highest activity and the single observation of completely null expression were siblings of the T1 family 826. Moreover, extracts from 826 were also quantitatively the second highest sample of the original 46 analyzed for enzyme activity in the T0 generation. By Western blot, we analyzed protein extracts from several T1 siblings of this family, including the highest (612 U/mg) and the lowest (0 U/mg) and found a clear linear correlation between the amount of cross-reacting protein at 59 kDa and the activity loaded in each lane. In addition to the 59 kDa band, there were also variable amounts of cross-reacting protein at 52 kDa. In the null individual there was only the 52 kDa protein. We never observed this molecular weight species in the T0 extracts or in any other T1 family. There was no evidence of proteolytic activity in this sample as judged by mixing the null sample with high activity extracts and analyzing by enzyme assays and Western blots after incubation at 37° C. If the apparently truncated rGCB was derived from proteolytic cleavage, the protease activity must be both physiologically induced and inactive under these isolation conditions. When the null individual was self-pollinated and the T2 generation analyzed, enzyme expression reappeared as in the T1 and T0. Our working hypothesis was that the tobacco plant is able to limit the expression of the foreign enzyme as constitutively expressed from this cDNA construct, and that the threshold for the stochastic induction of this response during development occurs at an expression level corresponding to approximately 600 U/mg specific activity in the crude homogenate. Of the lines we created, 826 were able to produce enough mRNA to exceed this threshold in the homozygous state.

The silencing of genes in plants is a recently described phenomenon. Work has been done detailing a cellular surveillance mechanism that has apparently evolved to specifically degrade excess RNA (36). In one case, specific RNA cleavages near the 3'-end of the transcript initiate the removal of the transcript. Our description of the silencing of rGCB above 600 U/mg is the first association of silencing with a truncated protein, and may well be caused by a specific MRNA (and not protein) cleavage event. Gene silencing may determine an upper limit of expression attainable using constitutive transgene expression.

We subcloned the cDNA for glucocerebrosidase into a TMV-transient vector and cDNA combinations. Transcripts were synthesized in vitro and inoculated directly onto lower leaves of whole plants. In each case, there was an additional lag time of about 2 weeks post-inoculation before appearance of virus in the upper leaves of the plant and in each case the viral population no longer carried a significant portion of the gene. We detected no significant enzyme activity in either inoculated or systemically infected leaves. Very recently, we detected the gene in root tissue and in transfected protoplasts. There appears to be an incompatibility with leaf expression under conditions of viral amplification of the rGCB rMRNA. This incompatibility selects for loss of the sequence from the viral population.

To further investigate the nature of the leaf incompatibility with rGCB expression, we built the construct pBSG641. This plasmid contains the rGCB gene substituted into the coat protein region. The remaining portion of the entire genome was then placed under control of the 35S promoter. The promoter was designed to initiate RNA synthesis such that the correct 5'-end of TMV would be synthesized. A custom-designed, self-cleaving ribozyme sequence positioned at the end of the genome yields a native 3'-end upon cleavage. The vector was designed for synthesis of infectious transcripts in vivo from a chromosomally integrated locus and production of rGCB through viral amplification of subgenomic mRNA in the cytoplasm. The vector alone without the gene for rGCB produces a systemic but capsid-free, "naked-RNA" infection (38). This RNA co-suppression is the subject of issued U.S. Pat. No. 5,922,602 issued Jul. 13, 1999, the disclosure of which is incorporated herein by reference.

We introduced this construct (FIG. 15) into Agrobacterium and transformed tobacco plants as described above. In this case many of the plant leaves displayed necrotic lesions as transfection events randomly occurred during growth and development and expansion of leaves. These lesions never formed on control transformed plant lines containing vector only sequences capable of replication. These lesions were identical in appearance to the types of lesions induced by plant pathogens during a type of disease resistance reaction, termed the hypersensitive response (HR). Therefore, under conditions where we expect to accumulate large quantities of active enzyme, an HR is signaled by some component of the vector infection specific to rGCB. There are very few of these so-called HR "clicitors" characterized in the literature. Possibly rGCB enzyme itself, or a secondary metabolite resulting from enzymatic activity, or even rGCB RNA, may induce the HR. In any case, we hypothesize that the HR selects for loss of the gene from the viral RNA population. It is important to remember that this is not a simple genetic instability phenomenon. Under conditions where an HR is not induced, we have synthesized many proteins using TMV-based RNA viral vectors to levels of several percent of the total soluble cell protein without loss of the inserted gene even after virion passage.

Expression of rGCB in Transgenic Tobacco is Robust. In several experiments, we inoculated wild type TMV onto rGCB containing transgenic tobacco and found a ~1.5–2 fold increase in the specific activity of total homogenates. It appears that the viral-infection causes an increase in promoter activity, and/or the secretion and accumulation of active enzyme. This was an important result, because it demonstrates that the expression was compatible with a TMV infection, a physiologically severe stress condition. Furthermore, in separate work, we have used chimeric TMV particles as recombinant carriers for the production of small peptides (31).

Conclusions.

We used a wide range of gene expression tools to investigate the accumulation of rGCB in mature tobacco plants. Our results suggest attractive yield, quality and cost objectives can be met with further development. We observed two independent phenomena currently limiting the accumulation of enzyme activity in whole plants; gene silencing in one transgenic line, and a plant leaf hypersensitive response to transient vector mediated synthesis.

These current limitations in gene expression only serve to underscore the advantages and utility of agriculture for recombinant protein production. We have generated several transgenic tobacco lines as a reliable source of biomass for the production of high specific activity enzyme. Because the biomass is accumulated under no sterile growth conditions and production is inexpensively scaled to the quantities desired, it becomes feasible to exploit a dilute but enriched source such as the intercellular fluid fraction for industrial process development. This contrast is most clearly summarized in Table 4.

The placental homogenate procedure is adapted from Furbish et al., (10) starting with a 14,000×g sedimented material. In a typical preparation 15–30 kg of fresh placentas were processed. The tobacco homogenate is based on the average of 2 typical 1 kg extractions of the leaf biomass. The IF data is from an average of 5 small scale extraction experiments (2–200 grams fresh weight), and a single chromatography run of an IF concentrate. For comparative purposes all yields are normalized to 1 kg.

TABLE 4

INITIAL STEPS IN THE PURIFICATION OF GLUCOCEREBROSIDASE

| | PLACENTA HOMOGENAT | | | TOBACCO HOMOGENAT | | | TOBACCO LEAF IF | | |
|---|---|---|---|---|---|---|---|---|---|
| Purification Procedure | Activity Units/kg | Specific Activity Units/mg | Recovery % | Activity Units/kg | Specific Activity Units/mg | Recovery % | Activity Units/kg | Specific Activity Units/mg | Recovery % |
| Detergent Extraction | 1,510,000 | 375 | 100 | 1,870,000 | 230 | 100 | 877,000 | 9,967 | 100 |
| Concentration/ Delipidation | 707,000 | 9,330 | 47 | 1,540,000 | 14,400 | 82 | ⇓ | ⇓ | ⇓ |
| Hydrophobic Chromatography | 554,000 | 147,000 | 36 | 1,242,000 | 82,000 | 74 | 535,000 | 34,547 | 61 |

TABLE 5

GCB IF PILOT PROCESS

| | Greenhouse Scale (1 kg) | | | | Field Scale (100 kg) | | | |
|---|---|---|---|---|---|---|---|---|
| Purification Step | Specific Activity Units/kg | Total Activity Units/mg | Recovery % | Purification Fold | Specific Activity Units/kg | Total Activity Units/mg | Recovery % | Purification Fold |
| IF | 4,153,533 | 20,388 | 100 | 1.0 | 434,927 | 2,745 | 100 | 1.0 |
| Phenyl SL | 3,738,180 | 147,813 | 91.4 | 7.25 | 194,722 | 12,960 | 44.4 | 5.0 |
| SP Big Beads | 2,740,086 | 650,377 | 67.0 | 31.9 | 145,060 | 99,220 | 33.1 | 38.2 |

For comparative purposes all yields are normalized to 1 kg.

The greenhouse/laboratory scale process is based on an average of 2 infiltration/chromatography-runs starting with 1 kilogram of fresh weight leaf tissue.

The GenBank accession No. for glucocerebrosidase is M11080. The field scale process is an average of 7 large scale infiltrations consisting of 100 kilograms of fresh weight tissue. Enzyme activity is based on the cleavage of 4-methylumbelliferylglucoside (1 Unit=1 nmol/hr). One factor contributing to a lower apparent yield in the field on a fresh weight basis is that rGCB is concentrated in the leaf lamina and in the lab scale procedure the midrib was removed.

Biosource Technologies Standard Operating Procedure (No. GCB35)

Preparation of Solutions for GCB Assay with 4-Methyl umbelliferyl β-D-glucopyranoside 1. GCB Assay Buffer
   0.1 M Potassium Phosphate, 0.15% Triton X-100, 0.125% sodium taurocholate (Sigma T-4009), 0.1% bovine serum albumin, 0.02% sodium azide, pH 5.9
   Dissolve 13.6 grams of potassium phosphate monobasic ($KH_2PO_4$) in 950 ml of distilled water. Add 1.25 g of sodium taurocholate and 1.5 g of Triton X-100. Triton X-100 is a very viscous liquid and should be weighed rather than pipetted in order to achieve a reproducible buffer. Add 2 ml of 10% sodium azide and 1 gram of bovine serum albumin (BSA). Stir until all material has dissolved. Adjust the pH to 5.9 by the addition of a small amount of 1 N NaOH, then bring up to 1000 ml with water.
   Filter sterilize and store at 4° C. This buffer is stable for many months.
2. Stopping Buffer
   0.1 M Glycine in 0.1 M NaOH
   Dissolve 4 grams of NaOH and 7.51 grams of glycine in 1 liter of distilled water. Filter sterilize and store at 4° C. (Stable for years at 4° C.).
3. Substrate (Sigma M-3633) FW 338.3
   15 mM 4-methylumbelliferyl β-D-glucopyranoside (4-MUG) in assay buffer
   Weigh out 1 gram of 4-MUG into a 500 ml Erlenmeyer flask. Add exactly 197 ml of Assay Buffer (Substrate dilution Buffer) and heat in a hot water bath to dissolve. Caution: Heating too aggressively results in unacceptably high background fluorescence.
   After cooling, dispense into 5–7 ml aliquots in 15 ml polypropylene tubes, let tubes cool to room temperature and freeze at −20° C. for later use.
4. 125 mM Conduritol β-epoxide (CBE) (Toronto Research C-66600)
   MW=162.18
   Dissolve 100 mg of CBE in 4.92 ml of 0.1 M $KPO_4$ Buffer, pH 6.0. Dispense into 200–500 μl aliquots and store at −20° C.
5. 0.1 M $KPO_4$ Buffer, pH 6.0
   1.75 ml of 0.5 M $KH_2PO_4$ (Solution A) 87.5 mM
   0.246 ml of 0.5 M $K_2HPO_4$ (Solution B) 12.3 mM
   Add distilled water to 10 ml.

Reagents:
   Potassium Phosphate Monobasic ($KH_2PO4$) Fisher Scientific P285
   Potassium Phosphate Dibasic ($K2HPO_4$) Fisher Scientific P288
   Triton X-100 Sigma X-100
   Sodium Taurocholic Acid Sigma T-4009
   Bovine Serum Albumin, Fraction V Sigma A-2153
   Sodium Azide Sigma S-2002
   Glycine Sigma G-4392
   Sodium Hydroxide Pellets Fisher Scientific S318
   Conduritol β-epoxide (CBE) Toronto Research C-66600 MW =162.18
   4-Methylumbelliferyl β-D-glucopyranoside (β-D-glucoside) Sigma M-3633

Biosource Technologies Standard Operating Procedure (No. GCB36)

GCB Assay with 4-Methylumbelliferyl β-D-glucopyranoside (MUG)

1.0 Purpose
   To measure the amount of glucocerebrosidase activity from transgenic tobacco plants following infiltration and/or homogenization of the tissue. Measurement of fluorometric activity requires an accurate determination and relationship between fluorescence of the released methylumbelliferone and its concentration under the assay conditions.

Scope
   This is an inhibition assay. CBE inhibits human GCB. The fluorescent value used to calculate activity is based on the difference in values with and without inhibitor present. The fluorescent value with CBE (plant glucosidase) is subtracted from the fluorescent value without inhibitor which is both plant and human GCB activity. The difference being the value for human GCB expressed in the transgenic plants. The assay is carried out using 5 μl of sample with 45 μl assay buffer+/− CBE at 37° C. This means that 2 tubes are needed per sample. This procedure is applicable to the Glucocerebrosidase assay procedure requiring a methylumbelliferone standard curve.

Equipment
Fluorometer (St. John Associates Fluoro-Tec 2001A with KV-418 filter and 365 nm interference filter)
10×75 mm cuvettes (St. John Associates)

Water Bath
Test Tubes 13×100 mm glass (VWA or equivalent)
4-Methylumbelliferone (Sigma M-c381)
Pipettes and pipette tips, 5 μl–1 ml (Rainin or equivalent)
1.5 ml microfuge tubes Precautions The fluorometer should be warmed up for at least 20 minutes prior to reading samples. The power switch should be left on at all times. If the power switch was turned off it may take longer (up to 1 hour) for the instrument to stabilize.

Be certain to put away all reagents under proper storage conditions after reading assays. Any left over fluorescent substrates and CBE stock should be returned to –20° C. The fluorescent substrate and CBE stock can be frozen and thawed numerous times without any breakdown of the reagents. Do not save any substrate or assay buffer to which you added CBE. These should be discarded. You should only make up enough reagent with the inhibitor (CBE) that you currently need.

Procedure

1. Turn on the water bath and check to be certain the temperature is set to 37° C.
2. Turn on fluorometer to warm up by flipping up the PMT switch. It should be turned on at least 15–20 minutes before taking readings. If the power switch was turned off it may take longer (up to 1 hour) for the instrument to stabilize.
3. Remove assay buffer from refrigerator and CBE (conduritol D epoxide) from –20° C. freezer. Thaw CBE on ice.
4. Defrost the appropriate amount of methylumbelliferyl β-D-glucopyranoside (MUG) substrate. You need 400 μl of MUG for each sample (+/–CBE). Place tubes in 37° C. $H_2O$ bath for approximately 10 minutes to get MUG into solution. Note: There may be a small amount of insoluble material (MUG) in each tube even after the 10 minutes at 37° C. Vortex before use. Keep at room temperature until ready to use.
5. Remove enough GCB Assay Buffer from the stock bottle that will be needed for your samples and transfer to a 15 ml tube. Add appropriate amount of 125 mM stock 0.55 mM CBE. CBE stock is β stored at –20° C. Thaw some CBE on ice now if you have not already done so. The assay buffer+CBE may be kept at room temperature if assays will be completed within 1 hour otherwise store solutions with CBE on ice.

Note: you want the final conc. of CBE in the assay to be 0.5 mM, you are adding 45 μl of buffer to 5 μl of sample so the starting conc. of CBE should be 0.55 mM.

Example: Add 8.8 μl of 125 mM CBE stock solution to 1.991 ml of assay buffer to equal 0.55 mM CBE in assay buffer. This is enough buffer to carry out at least 40 assays.

6. Label two 13×100 mM glass tubes for each sample to be assayed with a number and the same number and a "+" sign. (1, 1+, 2, 2+, etc). Tubes with "+" contain CBE, tubes with just a number will not have CBE added to the assay buffer or MUG.

Carry out the following steps on ice.

7. Place numbered tubes in white racks and place in Styrofoam ice chest filled with enough ice and $H_2O$ (Ice Bath) to cover the volume of fluid in these tubes.
8. Add 45 μl assay buffer to all the tubes with numbers only. Add 45 μl of assay buffer+CBE to all the "+" tubes. Place pipette tip in bottom of tube to deliver assay buffer to bottom of tube.
9. Remove metal tip ejector from P-10 pipetman (so pipetman will reach bottom of tube) and pipette 5 μl of sample into each set of appropriate tubes of assay buffer (one "+" and one tube with a number only (–CBE) for each sample or twice this number if done in duplicate). Place pipette tip in bottom of tube to deliver-sample directly into assay buffer. This is very important since you will be pipetting small volumes into these tubes. Be sure to include a Buffer sample to blank the fluorometer. This will contain 5 μl of the same buffer that the samples are in.

Note: See Dilution of Enzymes if your sample is too concentrated to read in the fluorometer. Basically, dilute your sample 1:5, 1:10, etc. in assay buffer, mix well, pulse in microfuge and add 5 μl of diluted sample to assay buffer above. You should only need 5—10 μl of your sample for the dilutions.

10. Incubate tubes at –37° C. for 10 minutes then place tubes immediately on ice.
11. Aliquot the volume of MUG needed for "+" tube assays (200 μl per assay+CBE) into a 15 ml polypropylene tube and add CBE stock to a final concentration of 0.5 mM.

4 μl of 125 mM CBE per 1 ml MUG in assay buffer=0.5 mM CBE

12. Add MUG +/– CBE to appropriate tubes. Add 200 μl of MUG without CBE to all the tubes with a number only (–CBE). Add 200 μl of MUG+CBE to all the "+" tubes. Place a plastic cap over each tube. Vortex sample and place back on ice.
13. Transfer all tubes to 37° C. $H_2O$ bath. Incubate at 37° C. for 15 minutes with shaking. Set the shaker between the # 4–6 settings.
14. Transfer tubes to ice bath. Quickly add 1 ml of stopping solution to each sample. Remove rack of samples from ice.
15. You are now ready to read samples in fluorometer. Refer to SOP GCB37 for Fluorometer Instructions.
16. Be certain to put away all reagents under proper storage conditions after reading assays. Any left over fluorescent substrates should be returned to –20° C. The fluorescent substrate and CBE stock can be frozen and thawed numerous times without any breakdown of the reagents. Do not save any substrate or assay buffer to which you added CBE. These should be discarded. You should only make up enough reagent with the inhibitor (CBE) that you currently need.

Dilution of Samples for Assays

Routine dilutions of samples should be carried out on ice using the GCB Assay Buffer described above to maintain enzyme activity. Generally a 1:5 or 1:10 dilution of the sample is sufficient. Dilutions should be carried out in a microfuge tube. (Example: 1:10 dilution: 5 μl of sample in 45 μl of assay buffer, mix well and pulse sample in microfuge to bring all of the sample to the bottom of the tube). You should only need 5–10 μl of your sample for the dilutions.

EXAMPLE 2

Extraction of Glucocerebrosidase Protein

Glucocerebrosidase (GCB), either derived from human placental tissue or a recombinant form from Chinese hamster ovary cells (CHO), is presently used in an effective but costly treatment of the heritable metabolic storage disorder known as Gaucher disease. We combined a dual promoter from Cauliflower Mosaic Virus (35S), a translational enhancer from Tobacco Etch Virus and a polyadenylation region from the nopaline synthetase gene of Agrobacterium tumefaciens with the native human GCB cDNA to create plasmid pBSG638. These expression elements are widely used to provide the highest possible constitutive expression of nuclear encoded genes in plants. The CaMV promoter is further inducible by stress or wound treatment.

Using a standard Agrobacterium-mediated transformation method, we regenerated 93 independent kanamycin-resistant transformants from leaf discs of four different tobacco cultivars (the TO generation). In Western blots of total protein extracts, cross-reacting antigen was detected in 46 of these TO individuals with antibody raised against human glucocerebrosidase. Specificity of the plant-expressed recombinant enzyme was confirmed by hydrolysis of 14C-radiolabeled glucosylceramide. According to these expression results the rGCB positive transformants were ranked into moderate (A), low (B) and negligible (C) activity groups.

We also found reaction conditions to preferentially inhibit rGCB enzyme activity in the presence of plant glucosidases using the suicide substrate conduritol B-epoxide (CBE). Total glucosidase activity, and rGCB activity were measured by hydrolysis of the fluorescent substrate 4-methylumbelliferylglucopyranoside (4-MUG) with and without CBE. Leaves from plants transfected with the vector TT10A 103L were removed at the petiole and slit down the midrib into two equal halves. To obtain a total cellular homogenate, one group of half-leaves was ground in the presence of 4 volumes of detergent extraction buffer (100 mM potassium phosphate p(I 6, 5 mM EDTA, 10 mM, B-mercaptoethanol and 0.5% w/v sodium taurocholate) with a mortar and pestle after freezing the tissue in liquid nitrogen. To recover the intercellular fluid (IF), the same enzyme extraction buffer was infiltrated into the opposing group of half-leaves by submerging the tissue and applying moderate vacuum pressure (500 mm Hg). After draining off excess buffer, the undisrupted half-leaves were rolled gently in Parafilm, placed in disposable tubes and the intercellular fluid (IF) was collected by low-speed centrifugation (1,000 g). The weight of buffer recovered from the infiltrated leaf tissue is recorded and varies from approximately one-half to equal the original weight of the leaf. GCB expression in IF extracts was quantified using a commercially available enzyme assay reagents and protocol. Total protein was determined by the method described by Bradford Bradford, M. Anal. Biochem 72:248 1976.

We have demonstrated that active recombinant GCB may be successfully extracted from the intercellular fluid of plant leaves using the present method. The GCB assay is based on MUG hydrolysis in the presence of CBE. The IF method results in a recovery of 22% of the total GCB activity of the leaf at a 18-fold enrichment relative to an extract obtained by homogenization (H). The GCB production results may be improved by optimizing the time post-inoculation with the viral vector and minimizing the contaminating viral coat protein from the intercellular fraction.

EXAMPLE 3

Laboratory Pilot Scale Purification of Glucocerebrosidase from the Intercellular Fluid of Tobacco MD609 leaf tissue (1–2 kilograms) of transgenic tobacco expressing the lysosomal enzyme glucocerebrosidase was harvested, the mid vein removed and the tissue weighed. Tissue was submerged with 2–4 volumes of buffer (0.1 M $KPO_4$ buffer, pH 6.0, 5 mM EDTA, 0.5% taurocholic acid, 10 mM β-mercaptoethanol) in an infiltration vessel that accommodates several kilograms of leaf tissue at one time. A perforated metal plate was placed on top of tissue to weigh down the tissue. A vacuum of 25–27 in. Hg was applied for 1–2 minutes×3. The vacuum was released between subsequent applications. Tissue was rotated and the vacuum reapplied to achieve complete infiltration. Multiple applications of the vacuum without isolating the intercellular fluid constitutes a single infiltration procedure. An indication of complete infiltration is a distinct darkening in color of the underside of the leaf tissue. Excess buffer on the tissue was drained. The intercellular fluid was released from the tissue by centrifuging the tissue in a basket rotor at 4200 RPM (2500×g) for 10 minutes. The intercellular fluid was collected using an aspirator hooked up to a vacuum pump (IF-1). Alternatively, the leaf tissue can be re-infiltrated by placing the leaves back in the infiltration vessel in the same buffer used above and the process repeated (IF-2). The second infiltration does not require as many applications of the vacuum. Additionally, the buffer may be drained from the infiltration vessel (spent buffer) and pooled with the 1st and 2nd IF fractions. Collectively, IF-1, IF-2 and Spent Buffer constitutes the IF pool. The volume of intercellular fluid collected from the infiltrated leaf tissue was between 50–100% of the leaf tissue by weight depending on the number of infiltrations carried out.

Recombinant GCB was purified by loading the dilute intercellular (feed stream) directly on a Pharmacia Streamline 25 column containing Phenyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM citrate, 20% ethylene glycol, pH 5.0 and then eluted with 25 mM citrate, 70% ethylene glycol. The eluted material was further purified on a cation exchange resin, SP Big Beads (Pharmacia), equilibrated in 25 mM citrate, 75 mM NaCl, pH 5.0. GCB was eluted with either a step gradient of 25 mM citrate, 0.5 M NaCl, 10% ethylene glycol, pH 5.0 or a linear gradient of 75 mM–0,4 M NaCl in 25 mM citrate, pH 5.0. All chromatography steps were carried out at room temperature.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. One unit of activity is defined as the amount of enzyme required to catalyze the hydrolysis of 1 nmol of substrate per hour. Total protein was determined using the Bio-Rad Protein Assay based on the method of Bradford (Bradford, M. Anal. Biochem. 72:248; 1976).

Typically from 1 kilogram of leaves where IF-1 alone was collected we obtained 4 million units of GCB at a specific activity of 20,000. The Units/kg increased to 6 million with a lower specific activity of 10,000 when IF Pool was collected (IF-1, IF-2 and spent buffer). For more information on these experiments, see U.S. Ser. Nos. 09/132,989 and 09/500,554. The disclosures of which are incorporated herein by reference.

EXAMPLE 4

Ultrafiltration/Concentration of Intercellular Fluid from Tobacco Expressing Glucocerebrosidase 2.3 kilograms of MD609 leaf tissue from transgenic tobacco expressing the lysosomal enzyme glucocerebrosidase was harvested, the mid vein removed and the tissue weighed. Tissue was submerged with 24 volumes of buffer (0.1 M $KPO_4$ buffer, pH 6.0, 5 mM EDTA, 0.5% taurocholic acid, 10 mM β-mercaptoethanol) in an infiltration vessel that accommodates several kilograms of leaf tissue at one time. A perforated metal plate was placed on top of tissue to weigh down the tissue. A vacuum of 25–27 in. Hg was applied for 1–2 minutes×3. The vacuum was released between subsequent applications. Tissue was rotated and the vacuum reapplied to achieve complete infiltration. Excess buffer on the tissue was drained. The intercellular fluid was released from the tissue by centrifuging the tissue in a basket rotor at 4200 RPM (2500×g) for 10 minutes. The intercellular fluid was collected using an aspirator hooked up to a vacuum pump (IF-1). The leaf tissue was re-infiltrated by placing the leaves back in the infiltration vessel in the same buffer used above and the process repeated (IF-2). The buffer was drained from the infiltration vessel (spent buffer) and pooled with the 1 st and 2nd IF fractions. Collectively, IF-1, IF-2 and Spent Buffer constitutes the IF pool. The IF pool was filtered through Miracloth and then concentrated 6 fold by passing the IF pool through a 1 sq. ft. spiral membrane (30K molecular weight cutoff) using an Amicon RA 2000 concentrator equipped with an LP-1 pump.

Using the suicide substrate, conduritol B-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. One unit of activity is defined as the amount of enzyme required to catalyze the hydrolysis of 1 nmol of substrate per hour. Total protein was determined using the Bio-Rad Protein Assay based on the method of Bradford (Bradford, M. Anal. Biochem. 72:248; 1976).

EXAMPLE 5

Pilot Scale Purification of Glucocerebrosidase from the Intercellular Fluid of Field Grown Tobacco 100 kilograms of MD609 leaf tissue from transgenic tobacco expressing the lysosomal enzyme glucocerebrosidase was harvested from the field each day for a period of two weeks. The tissue was stripped off the stalks by hand and weighed. Five kilograms of leaves were placed into polyester bags (Filtra-Spec, 12-2-1053) and four×5 kg bags of leaves were placed into a metal basket. The metal basket containing the leaf material was placed in a 200 L Mueller vacuum tank containing ~100 liters of buffered solution (0.1 $KPO_4$ buffer, pH 6.0, 5 mM EDTA, 0.5% taurocholic acid, 10 mM β-mercaptoethanol). A 70 lb. stainless steel plate was placed over the leaves/bags to assure complete immersion. A vacuum was pulled 27 in. Hg, held for 1 minute and then rapidly released. This vacuum infiltration was repeated for a total of two cycles. Multiple applications of the vacuum without isolating the intercellular fluid constitutes a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue. Alternatively, the leaf tissue can be re-infiltrated by placing the leaves back in the infiltration vessel in the same buffer used above and the process repeated (IF-2). Additionally, the buffer-may be drained from the infiltration vessel (spent buffer) and may be pooled with the 1st and 2nd IF fractions. Collectively, IF-1, IF-2 and Spent Buffer constitutes the IF pool. The volume of intercellular fluid collected from the infiltrated leaf tissue was between 42–170% of the leaf tissue by weight depending on the number of infiltrations carried out.

Recombinant GCB was purified by loading the dilute intercellular (feed stream) directly on a Pharmacia Streamline 200 column containing Phenyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM citrate, 20% ethylene glycol, pH 5.0 and then eluted with 25 mM citrate, 70% ethylene glycol. The eluted material was sterile filtered by passing the eluted material through a 1 sq. ft. 0.8 um Sartoclean GF capsule followed by a 1 sq. ft. 0.2 um Sartobran P sterile filter (Sartorius, Corp.) and stored at 4° C. until the next chromatography step. The eluted material from 4–5 days of Phenyl Streamline chromatography runs was pooled together and further purified on a cation exchange resin, SP Big Beads (Pharmacia), equilibrated in 25 mM citrate, 75 mM NaCl, pH 5.0. GCB was eluted with a step gradient of 25 mM citrate, 0.4 M NaCl, 10% ethylene glycol, pH 5.0. All chromatography steps were carried out at room temperature. The eluted material was sterile filtered by passing the eluted material through a 1 sq. ft. 0.8 urn Sartoclean GF capsule followed by a 1 sq. ft. 0.2 um Sartobran P sterile filter (Sartorius, Corp.) and stored at 4° C.

Using the suicide substrate, conduritol β-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. Total protein was determined using the Bio-Rad Protein Assay based on the method of Bradford (Bradford, M. Anal. Biochem. 72:248; 1976).

Typically from 1 kilogram of field grown tobacco, expressing GCB, where IF-1 alone was collected we obtained 435,000 units of GCB at a specific activity of 2,745. The Units/kg increased to 755,000 with a specific activity of 3,400 when IF Pool was collected (IF-1, IF-2 and spent buffer).

EXAMPLE 6

Total GCB (IF vs. Homogenate) in "GCB Field Test Virus"

100 kilograms of MD609 leaf tissue from transgenic tobacco expressing the lysosomal enzyme glucocerebrosidase was harvested from the field each day for a period of two weeks. The tissue was stripped off the stalks by hand and weighed. Five kilograms of leaves were placed into polyester bags (Filtra-Spec, 12–2–1053) and four×5 kg bags of leaves were placed into a metal basket. The metal basket containing the leaf material was placed in a 200 L Mueller vacuum tank containing ~100 liters of buffered solution (0.1 $KPO_4$ buffer, pH 6.0, 5 mM EDTA, 0.5% taurocholic acid, 10 mM β-mercaptoethanol). A 70 lb. stainless steel plate was placed over the leaves/bags to assure complete immersion. A vacuum was pulled 27 in. Hg, held for 1 minute and then rapidly released. This vacuum infiltration was repeated for a total of two cycles. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue. In order to evaluate how much enzyme was recovered in the intercellular fluid, the tissue from which the intercellular fluid was isolated was then homogenized in a Waring blender with 4 volumes of the same infiltration buffer as above, centrifuged and the supernatant assayed for enzyme activity.

EXAMPLE 7

Chops Experiment

An experiment was carried out where 100 kilograms of MD609 leaf tissue of transgenic tobacco expressing the lysosomal enzyme glucocerebrosidase was harvested off the stalks by hand, weighed and chopped into small pieces to increase the surface area for buffer infiltration. Five kilograms of leaves were placed into polyester bags (Filtra-Spec, 12-2-1053) and four×5 kg bags of leaves were placed into a metal basket. The metal basket containing the leaf material was placed in a 200 L Mueller vacuum tank containing ~100 liters of buffered solution (0.1 $KPO_4$ buffer, pH 6.0, 5 mM EDTA, 0.5% taurocholic acid, 10 mM β-mercaptoethanol). A 70 lb. stainless steel plate was placed-over the leaves/bags to assure complete immersion. A vacuum was pulled 27 in. Hg, held for 1 minute and then rapidly released. This vacuum infiltration was repeated for a total of two cycles. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue. In order to evaluate how much enzyme was recovered in the intercellular fluid, the tissue from which the intercellular fluid was isolated was then homogenized in a Waring blender with 4 volumes of the same infiltration buffer as above, centrifuged and the supernatant assayed for enzyme activity.

Recombinant GCB was purified by loading the dilute intercellular (feed stream) directly on a Pharmacia Streamline 200 column containing Phenyl Streamline resin. The column was equilibrated and washed until UV-signal on recorder returned to baseline with 25 mM citrate, 20% ethylene glycol, pH 5.0 and then eluted with 25 mM citrate, 70% ethylene glycol. All chromatography steps were carried out at room temperature Table 10 below contains data from the chops experiment.

EXAMPLE 8

Pilot Scale of Purification of Alpha Galactosidase from the Intercellular Fluid of Nicotiana Benthamiana Young actively growing Nicotiana benthamiana plants were inoculated with infectious transcripts of a recombinant plant viral construct containing the lysosomal enzyme α galactosidase gene. Systemically infected leaf tissue (1–2 kilograms) was harvested from Nicotiana benthamiana expressing α galactosidase 14 days post inoculation. The tissue was weighed and submerged with 2–4 volumes of buffer (25 mM Bis Tris Propane Buffer, pH 6.0, 5 mM EDTA, 0.1 M NaCl, 10 mM β-mercaptoethanol) in an infiltration vessel that can accommodate several kilograms of leaf tissue at one time. A perforated metal plate was placed on top of tissue to weigh down the tissue. A vacuum of 25–27 in. Hg was applied for 30 seconds and then quickly released. The tissue was rotated and the vacuum reapplied to achieve complete infiltration which was confirmed by a distinct darkening in color of the underside of the leaf tissue. Excess buffer on the tissue was drained. The intercellular fluid was released from the tissue by centrifuging the tissue in a basket rotor at 3800 RPM (2100×g) for 10–15 minutes. The intercellular fluid was collected using an aspirator hooked up to a vacuum pump. In some instances only infected leaf tissue was harvested. Alternatively, petioles and stems have been harvested along with the leaf tissue for infiltration. The mid vein was not removed from the tissue prior to infiltration.

Alpha galactosidase was purified by loading the dilute intercellular (feed stream) directly onto a Pharmacia Streamline 25 column containing Butyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM Bis Tris Propane, pH 6.0 20% $(NH_4)_2SO4$ and then eluted with 25 mM Bis Tris Propane, pH 6.0. The eluted material was further purified on Hydroxyapatite equilibrated with 1 mM $NaPO_4$ Buffer, 5% glycerol, pH 6.0 and eluted with either a 1–250 mM $NaPO_4$ buffer, 5% glycerol, pH 6.0 linear gradient or a step gradient. All chromatography steps were carried out at room temperature.

Alpha galactosidase activity was measured by hydrolysis of the fluorescent substrate 4-methylumbelliferyl a-D galactopyranoside. Enzyme activity was measured at 37° C. in a reaction mixture containing 5 mM methylumbelliferyl a-D galactopyranoside, 0.1 M Potassium Phosphate, 0.15% Triton-X100, 0.125% sodium taurocholate, 0.1% bovine serum albumin, pH 5.9. Total protein was determined using the Bio-Rad Protein Assay based on the method of Bradford (Bradford, M. Anal. Biochem. 72: 248; 1976).

From 1 kilogram of leaves, we typically obtain between 140–160 million units of α galactosidase at a specific activity of 800,000 following a single infiltration procedure (IF-1). Table 11 below contains data that is representative of several experiments.

EXAMPLE 9

Pilot Scale Purification of Glucocerebrosidase from the Intercellular Fluid of Field Grown Tobacco Transgenic tobacco (MD609) expressing the lysosomal enzyme glucocerebrosidase was mechanically inoculated with a tobacco mosaic virus derivative containing a coat protein loop fusion, TMV291, (Turpen, et. al., 1995, Bio/Technology 13: 23–57). A total of 100 Kg of transgenic, transfected leaf tissue was harvested from the field, five weeks post inoculation. The tissue was stripped off the stalks by hand and weighed. Five kilograms of leaves were placed into polyester bags (Filtra-Spec, 12-2-1053) and four×5 kg bags of leaves were placed into a metal basket. The metal basket containing the leaf material was placed in a 200 L Mueller vacuum tank containing ~100 liters of buffered solution (0.1 $KPO_4$ buffer, pH 6.0, 5 mM EDTA, 0.5% taurocholic acid, 10 mM β-mercaptoethanol). A 70 lb. stainless steel plate was placed over the leaves/bags to assure complete immersion. A vacuum was pulled 27 in. Hg, held for 1 minute and then rapidly released. This vacuum infiltration was repeated for a total of two cycles. Multiple applications of the vacuum without isolating the intercellular fluid constitutes a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The intercellular fluid (IF) was recovered from the vacuum infiltrated leaves by centrifugation (1,800×g, 30 minutes) using a Heine basket centrifuge (bowl dimensions, 28.0 inches diameter×16.5 inches). Collected IF was filtered through a 50 uM cartridge filter and then stored at 4° C., until the entire 100 kilograms of tissue was infiltrated. This process was repeated with the next set of four 5 kg bags (5×20 Kg cycles total) until all the tissue was infiltrated. Additional buffer was added during each infiltration cycle to completely immerse the tissue.

Recombinant GCB was purified by loading the dilute intercellular (feed stream) directly on a Pharmacia Streamline 200 column containing Phenyl Streamline resin. Expanded bed chromatography enabled us to capture, clarify and concentrate our protein in one step without the need for centrifugation and/or microfiltration steps. The column was equilibrated and washed until UV-signal on recorder returned to baseline with 25 mM citrate, 20% ethylene glycol, pH 5.0 and then eluted with 25 mM citrate, 70% ethylene glycol. The eluted material was sterile filtered by passing the eluted material through a 1 sq. fl. 0.8 um Sartoclean GF capsule followed by a 1 sq. ft. 0.2 um Sartobran P sterile filter (Sartorius, Corp.) and stored at 4° C. until the next chromatography step. The eluted material from 4–5 days of Phenyl Streamline chromatography runs was pooled together and further purified on a cation exchange resin, SP Big Beads (Pharmacia), equilibrated in 25 mM citrate, 75 mM NaCl, pH 5.0. GCB was eluted with a step gradient of 25 mM citrate, 0.4 M NaCl, 10% ethylene glycol, pH 5.0. All chromatography steps were carried out at room temperature. The eluted material was sterile filtered by passing the eluted material through a 1 sq. ft. 0.8 um Sartoclean GF capsule followed by a 1 sq. ft. 0.2 um Sartobran P sterile filter (Sartorius, Corp.) and stored at 4° C.

Using the suicide substrate, conduritol B-epoxide (CBE), inhibition of recombinant glucocerebrosidase (rGCB) activity in the presence of plant glucosidases was achieved. Enzyme activity was measured at 37° C. in a reaction mixture containing 5 mM methylumbelliferyl β-D glucoside, 0.1 M Potassium Phosphate, 0.15% Triton-X100, 0.125% sodium taurocholate, 0.1% bovine serum albumin, pH 5.9 with and without CBE. Total glucosidase activity and rGCB activity were measured by hydrolysis of the fluorescent substrate 4-methylumbelliferyl glucopyranoside. Total protein was determined using the Bio-Rad Protein Assay based on the method of Bradford (Bradford, M. Anal. Biochem. 72:248; 1976). Table 12 contains the GCB recovery data from TMV transfected plant tissue.

The quantity of virus present in IF extracted leaf tissue was determined using homogenization and polyethylene glycol precipitation methods. In addition, the amount of virus present in the pooled, intercellular fluid was determined by direct polyethylene glycol precipitation. Final virus yields from precipitated samples was determined spectrophotometrically by absorbance at 260 nm.

TABLE 6

| Sample | Virus Titer |
|---|---|
| IF extracted leaf tissue | 0.206 mg virus/g fresh weight |
| Pooled IF | 0.004 mg virus/g fresh weight, 0.010 mg virus/ml IF |

EXAMPLE 10

Making rGAL-A Enzyme

Experimental Results. Achieving high steady-state MRNA levels is a prerequisite for vector development. However, there are many complex biochemical and host compatibility interactions that ultimately determine the overall performance of a heterologous expression system for a given protein. For this reason, we initiated some preliminary experiments to test the potential for RNA-viral mediated synthesis of active rGal-A in whole plants.

Figure 1:
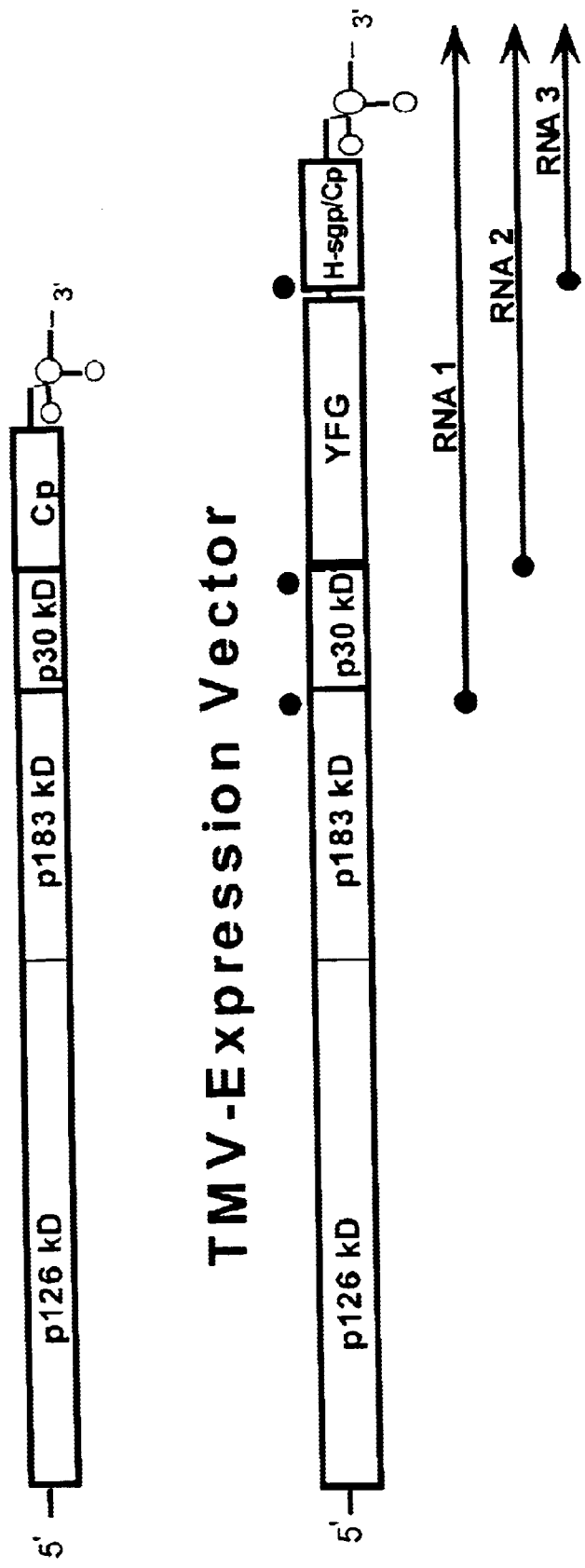
FIG. 1 shows a Tobamovirus expression vectors. YFG refers to any foreign gene.

In order to ensure efficient delivery of rGal-A into the lumen of the plant endoplasimic reticulum we fused the Gal-A cDNk (31) to a plant signal peptide sequence derived from rice α-amylase gene (32,33). We also hypothesized that addition of an ER-retention signal (SEKDEL) (SEQ ID: NO. 18) might prolong the resident time of the recombinant protein in the ER to increase the fraction of correctly assembled and catalytically active enzyme under extreme conditions of protein synthesis. These constructs were subcloned into the viral vector TTODA, a chimera between tobacco and tomato mosaic viruses (FIG. 1). Transcripts were prepared in vitro and inoculated onto the lower leaves of whole plants (Nicotiana benthamiana). 1–3 weeks after inoculation, leaves were weighed, rolled in a strip of Parafilm and placed in a disposable chromatography column and submerged in enzyme extraction buffer (0.1 M K/P04. 0.1 M NaCl. 5 mM EDTA. 10 mM β-ME and 0.5% sodium taurocholate. pH 6.0). In order to infiltrate the buffer into the tissue, a vacuum of 730–750 mmHg was twice applied. After draining the excess buffer, the intercelluar fluid fraction was recovered by low-speed centrifugation (~1.500×g. 15 min). To measure enzyme remaining in the tissue after this treatment, the leaf was unrolled after centrifugation and two discs removed with a #14 cork borer. This tissue sample was transferred to an eppendorf tube, frozen in liquid nitrogen and ground in four volumes of enzyme extraction buffer. In rGal-A enzyme assays, we measured cleavage of the fluorogenic substrate 4-methyl umbeliferyl α-D-galactopyranoside (4-MUG) against known standards using established protocols (34). Units are nmoles of 4-MUG hydrolyzed per hour at 37° C.

In several initial experiments, plant leaves transfected with all constructs accumulated 1–2% of the total soluble plant protein as cross reacting immunologic material (CRIM) using antisera specific for Gal-A in quantitative Western analyses (data not shown). However, enzyme activity was much lower than expected for this amount of CRIM and furthermore was only 2–4 fold higher than activity due to endogenous plant α-galactosidase isozymes (See Table 1: Experiment Oct. 19, 1996). It also appeared that addition of the ER retention signal allowed highest accumulation of steady state activity and that the IF contained little if any additional activity or CRIM. There are three cellular fates for any glycoprotein synthesized in a plant leaf: secretion to the IF, retention in the ER or sorting to the vacuole (35). We reasoned that because the ER retention signal slightly increased expression, the majority of the enzyme was inactivated later in the secretory pathway. This could most likely occur by aggregation in the trans-golgi network as is reported during over-production of this enzyme in CHO-cells (36), and/or in the plant leaf vacuole. The IF fraction is quite clear and non-pigmented and is suitable for direct chromatography. Using the initial construct (rGal-SEKDEL) we partially purified small amounts of rGal-A from the IF on hydrophobic, lectin and size exclusion resins.

For several plant proteins vacuolar sorting information is located in a carboxy-terminal propeptide (CTPP; 37,38). During the original cloning and characterization of human Gal-A, Quinn et al., postulated a cathepsin-like potential CTPP cleavage for this enzyme at or near two arginine residues, 26 and 28 AA from the termination codon (39,40). The precise AA sequence at the carboxy terminus has, to our knowledge, never been reported. Because secretion in the plant leaf is through a default pathway we reasoned that deletion of specific sorting information from a postulated CTPP might yield more active enzyme in the IF. Analysis of a second set of constructs containing either 12 or 25 AA truncations, with and without the ER retention signal provided dramatic evidence for the significance of this region (See Table 13). In one construct, rGal 12-SEKDEL, virtually all of the CRIM is now assembled and stored as fully active enzyme and is secreted to the IF in significant quantities. As demonstrated in FIG. 3, rGal-A (~52 kDa) is now the most abundant plant protein in a crude leaf IF sample. The other predominant band at 17.5 kDa is the viral structural protein which likely contaminates this fraction from broken trichomes of the leaf surface.

TABLE 13 rGal-A Expression (U/Gram Leaf Tissue)

| Contract/Sample | Intercellular Fluid | Residual Homogenate | Total |
|---|---|---|---|
| Experiment | | | |
| Uninfected Plant | 2,800 | 7,500 | 10,300 |
| rGal-A | 5,100 | 10,900 | 25,000 |
| rGal-A | 5,400 | 15,000 | 20,400 |
| rGal-A-SEKDEL | 6,800 | 30,300 | 37,100 |
| rGal-A-SEKDEL | 5,200 | 34,500 | 39,700 |
| Experiment | | | |
| Uninfected Plant | 2,300 | 4,800 | 7,100 |
| rGal-A 25 | 4,000 | 8,900 | 12,900 |
| rGal-A 25 | 2,300 | 9,000 | 11,300 |
| rGal-A 25-SEKDEL | 3,200 | 10,000 | 13,200 |
| rGal-A 25-SEKDEL | 2,800 | 8,600 | 11,400 |
| rGal-A 12 | 5,500 | 11,700 | 17,200 |
| rGal-A 12-SEKDEL | 109,800 | 117,700 | 227,500 |
| rGal-A 12-SEKDEL | 199,000 | 329,500 | 528,500 |

EXAMPLE 11

α-Galactosidase Expression Vector Development, Construction and Testing

The following example describes the series of α-galactosidase vectors that were constructed and tested for enzyme production. Initially, the human α-galactosidase A cDNA (Sugimoto, Y., Aksentijevich, I., Murray, G. J., Brady, R. O., Pastan, I., and Gottesman, M. M. Retroviral coexpression of a multidrug resistance gene (MDRI) and human (α-galactosidase A for gene therapy of Fabry disease. Human Gene Therapy 6:905, 1995.) was fused to a plant signal peptide sequence derived from a rice (x-amylase gene (Kumagai, M. H., Shah, M., Terashima, M., Vrkljan, Z., Whitaker, J. R., and Rodriguez, R. L. Expression and secretion of rice α-amylase by Saccharomyces cerevisiae. Gene 94:209, 1990.). This chimeric gene was subcloned into the TMV based expression vector TTODA resulting in a construct designated rGAL-A , see Table 1. Vector rGAL-A was modified by the addition of the putative ER retention signal SEKDEL, resulting in the vector designated rGAL-AR, see Table 1.

A series-of C-terminal amino acid deletions were introduced into the α-galactosidase gene. Deletions of 4, 8, 12 or 25 codons from the C-terminus of rGAL-A were generated as well as the addition of the putative ER retention sequence (SEKDEL), see Table 1 and FIG. 1 (sequence of TTODA (rGAL-12R). The deletion vectors were designated as described in Table 8:

TABLE 8

| Vector Designation | Carboxy-Terminal Modifications (Amino Acid Sequence) |
|---|---|
| rGAL-A | TSRLRSHINPTGTVLLQLENTMQMSLKDLL (SEQ ID NO:3) |
| rGAL-AR | TSRLRSHINPTGTVLLQLENTMQMSLKDLLSEKDEL (SEQ ID NO:4) |
| rGAL-4 | TSRLRSHINPTGTVLLQLENTMQMSL (SEQ ID NO:5) |
| rGAL-4R | TSRLRSHINPTGTVLLQLENTMQMSLSEKDEL (SEQ ID NO:6) |
| rGAL-8 | TSRLRSHINPTGTVLLQLENTM (SEQ ID NO:7) |
| rGAL-8R | TSRLRSHINPTGTVLLQLENTMSEKDEL (SEQ ID NO:8) |
| rGAL-12 | TSRLRSHINPTGTVLLQL (SEQ ID NO.9) |
| rGAL-12R | TSRLRSHINPTGTVLLQLSEKDEL (SEQ ID NO:10) |
| rGAL-25 | TSRLR (SEQ ID NO:11) |
| rGAL-25R | TSRLRSEKDEL (SEQ ID NO:12) |

The α-galactosidase gene fragment present in vector rGAL-12R was placed into TMV vector SBS5. In addition, the rice α-amylase signal peptide present in rGAL-12R was replaced by the native human α-galactosidase signal peptide. The resultant vector designated SBS5-rGAL-12R, see FIG. 2., exhibited genetic stability upon serial passage on N. benthamiana plants.

α-galactosidase was extracted from inoculated plants using interstitial fluid and homogenization methods. Fluids were analyzed for α-galactosidase yield, enzyme activity and cellular partitioning and targeting, see Table 15. In all cases, infectious transcripts were prepared in vitro and inoculated onto the lower leaves of actively growing Nicotiana benthamiana plants. Characteristic viral symptoms, vein clearing and leaf curling, were noted ~6–8 dpi (days post inoculation). Tissue samples were obtained from infected plants 1–3 weeks after inoculation. Leaves were weighed, rolled in a strip of Parafilm and placed in a disposable chromatography column and submerged in extraction buffer (0.1 M KIP04, 0.1 M NaCl, 5 mM EDTA, 10 mM β-ME and 0.5% sodium taurocholate, pH 6.0). Extraction buffer was infiltrated into the tissue by pumping a vacuum of 730–750 mmHg. The vacuum was applied and released two times. After draining the excess buffer, the interstitial fluid (IF) fraction was recovered by low-speed centrifugation (~1,500×g, 15 min). To measure enzyme remaining in the tissue after this treatment, the leaf was unrolled after centrifugation and two discs (~1 mg each) removed with a #14 cork borer. This tissue sample was transferred to an Eppendorf tube, frozen in liquid nitrogen and ground in four volumes of extraction buffer. The total homogenate was then subjected to centrifugation at ~5,000×g and the supernatant fraction was saved for further analysis.

Extracts from IF and homogenates from post-IF leaf tissue were analyzed for enzymatic activity by the hydrolysis of the fluorescent substrate 4-methyl umbeliferyl α-D-galactopyranoside (4-MUG). Known standards and established protocols (Suzuki, K. Enzymatic diagnosis of sphingolipidoses. Meth. Enzy. 138:727, 1987.) were used to obtain the number of enzymatic units (nmoles of 4-MUG hydrolyzed per hour at 37° C.) per gram fresh weight of tissue harvested.

TABLE 9

| Vector Designation | Interstitial Fluid Units/gram leaf | Homogenate Units/gram leaf | Total Enzyme Activity Units/gram leaf | Ratio of Activity IF/Homogenate |
|---|---|---|---|---|
| Uninfected | 3,837 | 9,404 | 13,241 | 0.41 |
| rGAL-A | 6,833 | 189,971 | 196,804 | 0.04 |
| rGAL-AR | 6,829 | 312,068 | 318,897 | 0.02 |
| rGAL-4 | 16,088 | 262,806 | 278,894 | 0.06 |
| rGAL-4R | 8,245 | 357,414 | 365,659 | 0.02 |
| rGAL-8 | 261,814 | 524,857 | 789,671 | 0.50 |
| rGAL-8R | 10,628 | 469,956 | 480,584 | 0.02 |
| rGAL-12 | 2,564 | 8,743 | 11,307 | 0.29 |
| rGAL-12R | 305,803 | 1,033,921 | 1,339,724 | 0.30 |
| rGAL-25 | 1,265 | 6,629 | 7,894 | 0.19 |
| rGAL-25R | 2,489 | 6,394 | 8,883 | 0.39 |

Enzyme activity data from IF and homogenates derived from plants expressing α-galactosidase from the vectors in Table 2. indicate that carboxy-terminal deletions (4–12 codons) results in increased 0-galactosidase expression. Vector rGAL-12R expressed the highest level of total α-galactosidase and also secreted the highest quantity of active enzyme.

EXAMPLE 12

Pilot Scale Purification of α-Galactosidase

Actively growing Nicotiana benthamiana plants, propagated in an uncontrolled horticultural greenhouse, were inoculated with encapsidated transcripts derived from the expression vector, SBS5-rGAL-12R. Tissue was harvested 14–17 days post inoculation. Five kilograms of leaves were placed into polyester bags (Filtra-Spec®, 12-2-1053) and four×5 kg bags of leaves were placed into a metal basket. The metal basket containing the leaf material was placed in a 200 liter Mueller® vacuum tank containing ~100 liters of buffered solution (50 mM acetate, 5 mM EDTA, 10 mM 2-mercaptoethanol, pH5.0). A 70 lb. stainless steel plate was placed over the leaves/bags to assure complete immersion. A vacuum was pumped to 695 mm Hg, held for 1 minute and then rapidly released. This vacuum infiltration was repeated for a total of two cycles. Multiple applications of the vacuum without isolating the interstitial fluid constitutes a single infiltration procedure. An indication of complete infiltration is a distinct darkening in color of the underside of the leaf tissue. Following the vacuum infiltrations, the leaves and basket were removed from the vacuum tank. The bags containing the vacuum infiltrated leaves were allowed to gravity drain surface buffer for ~10 minutes, prior to centrifugation. The interstitial fluid (IF) was recovered from the vacuum infiltrated leaves by centrifugation (1,800×G, 30 minutes) using a Heine® basket centrifuge (bowl dimensions, 28.0 inches diameter×16.5 inches). The IF was filtered through a 50 μm cartridge filter to remove plant debris prior to purification.

Ammonium sulfate was added to the IF to 15% saturation, mixed for 10 minutes and loaded onto a Pharmacia Streamline 200 column containing 4 liters of Butyl Streamline resin equilibrated with 25 mM Imidizole, 15% $(NH_4)_2SO_4$, pH 6.0 at 1.2 L/min. The column was washed to UV baseline with 25 mM Imidizole, pH 6.0, 15% $(NH_4)_2SO_4$ and a Gal was eluted with a step gradient of 25 mM Imidizole, pH 6.0. The eluent was filtered through a Sartorius glass fiber –>0.8 um cartridge filter and loaded directly onto 3 liters of Blue Sepharose in a Pharmacia BPG 200 column equilibrated with 25 mM Imidizole, pH 6.0. The column was washed to UV baseline with 25 mM Imidizole, pH 6.0 and α gal was eluted with a step gradient of 25 mM Imidizole, 650 mM NaCl, pH 6.0. The eluent was concentrated using a 10 kD MWCO, cellulose acetate, 3 ft$^2$ spiral membrane in an Amicon CH-2 concentrator and then sterile filtered.

Further purification was carried out either on Octyl Sepharose FF or Hydroxyapatite. For Octyl Sepharose the column was equilibrated with 25 mM Imidizole, 25% ammonium sulfate, pH 6.0 and eluted using a linear gradient of 25–0% (NH$_4$)$_2$SO$_4$ in 25 mM Imidizole, pH 6.0. For Hydroxyapatite purification, the sample was dialyzed overnight against 10 mM KPO$_4$Buffer, pH 7.0 and then loaded on a column was equilibrated with 10 mM KPO$_4$Buffer, pH 7.0. The column was washed with equilibration buffer until the UV reached baseline, followed by a linear gradient of 10–200 mM KPO$_4$Buffer, pH 7.0. The ax gal flowed through the column free of the contaminating proteins.

Alpha gal activity was measured throughout the process with a fluorescent assay using the synthetic substrate, 4-methylumbelliferyl-α-D-galactopyranoside (MU-α gal). Enzyme activity was measured at 37° C. in a reaction mixture containing 5 mM methylumbelliferyl α-D-galactopyranoside, 0.1 M Potassium Phosphate, 0.15% Triton-X100, 0.125% sodium taurocholate, 0.1% bovine serum albumin, pH 5.9.). One unit of enzymatic activity hydrolyzes 1 nmol of MU-α-gal per hour at 37° C. Total protein was determined using the Bio-Rad Protein Assay based on the method of Bradford (Bradford, M. Anal. Biochem. 72: 248; 1976). Results of α-galactosidase activity (Total units and specific activity) from different enzyme production lots are shown in Table 10.

TABLE 10

| Lot Number | Kg Biomass Extracted | Total Units (IF) | Specific Activity Units/mg protein (Purified) |
|---|---|---|---|
| 981215 | 44.4 | 2.9 × 10$^9$ | 5.0 × 10$^6$ |
| 991115 | 100 | 5.5 × 10$^9$ | 3.6 × 10$^6$ |
| 991116 | 120 | 6.9 × 10$^9$ | 4.0 × 10$^6$ |
| 991117 | 120 | 5.9 × 10$^9$ | 3.5 × 10$^{6*}$ |
| 991118 | 95.6 | 7.0 × 10$^9$ | 3.5 × 10$^{6*}$ |

*Butyl eluents from lots 991117 and 991118 were pooled before final chromatography and purification. The data presented in Table 16. demonstrates the consistency of pilot-scale extraction with respect to secreted enzyme yield and specific activity.

EXAMPLE 13

Analysis of Purified α-Galactosidase

N-terminal Sequence Analysis

N-terminal sequence analysis of α-galactosidase, purified from plants inoculated with transcripts derived from the vector rGAL-12R, MLDNGLARTPT, had a 100% sequence homology to 11 amino acids of human placental α-galactosidase with the addition of an N-terminal methionine. In contrast, N-terminal sequence of α-galactosidase, purified from plants inoculated with transcripts derived from the vector SBS5-rGAL-12R, LDNGLARTPT, was as expected from native human enzyme. These data indicates the high degree of fidelity that post-translational modifications are carried out within plant leaf cells and that human signal peptides are processed with equal specificity in plants in the native mamnmalian source.

C-Terminal Sequence Analysis

C-Terminal sequence of the rGAL-12R and SBS5-rGAL-12R plant produced enzyme was obtained by Edman degradation using the commercial service of the Mayo Foundation. Three cycles were achieved before the signal was too low to read additional sequence. Expected. C-Terminus: LLQLSEKDEL Cycle Major Amino Acids 1st L, E 2nd D, V, A 3rd Q, G, T It is important to note that the C-terminal amino acid was found to be heterogeneous, either L or E. The presence of glutamic acid in the first cycle greatly reduced the signal because glutamic acid can form a cyclic structure during the activation step that disables cleavage from the chain and therefore blocks a portion of the sample to further sequencing. This reduced that ability of the software to interpret cycle 3 and beyond. However, the presence of L, E and D in the first two cycles and the absence of other amino acids present in the analysis in an order resembling the α-galactosidase sequence strongly suggests that a population of the enzyme terminates with a DEL sequence as expected from the sequence of the DNA clone.

Molecular Weight Determination

The apparent molecular weight of SBS5-rGAL-12R derived α-galactosidase (~50 kDa) was quite similar to human α-galactosidase A, purified from human placenta, as judged by both coomassie and silver stained SDS-PAGE. However, the protein purified from plant sources showed less molecular weight variation than the native human protein, indicating less heterogeneity in plant glycosylation or a higher purity plant enzyme preparation.

The molecular mass of several lots of plant derived α-galactosidase were determined by MALDI-TOF mass spectroscopy to be 48,963, 48,913, 49,100 daltons. These weights are consistent with the predicted mass of α-galactosidase, based upon amino acid sequence, allowing for broader peaks due to glycosylation. The calculated molecular weight of SBS5-rGAL-12R derived α-galactosidase is 44,619. The difference in predicted and observed mass would equate to approximately 10.0% carbohydrate.

Glycan Analysis

There are four potential N-glycosylation consensus sequences (N-X-T/S) reported for human a gal A (Matsuura, et. al. Glycobiology 8:329–339, 1998). We have identified four potential sites (108, 161, 184, 377) in our plant expressed α gal. One potential glycosylation site, in our α gal, is not glycosylated (377), as is the case for human α gal A expressed in CHO-cells.

Plants have both high mannose and complex glycans that differ from mammalian complex glycans by the presence of an α1,3 fucose on the proximal GlcNac and a β1,2 xylose on the β-linked mannose of the core. Four potential N-glycosylation sites have been identified for the plant derived α-galactosidase. The predicted amino acid sequence has four possible glycosylation sites (Asn-Xaa-Ser/Thr) at Asn residues (108, 161, 184, 377). The glycosylation site at amino acid 377 was not glycosylated, similar to CHO cell derived α-galactosidase glycosylation. The four possible N-glycosylation sites are all located in β turns within hydrophilic regions of the enzyme. It was estimated the mature human α-galactosidase consists of about 370 amino acids and approx. 15% carbohydrate (Calhoun et al. PNAS 82: 7364–7368, 1985). Matsuura et al (Glycobiology 8:329–339,1998) reports that in CHO-cell produced α gal there are four N-glycosylation sites (139, 193, 215, 407) and 3 of the 4 sites are occupied (407 is not glycosylated).

We have determined that our plant expressed protein is indeed glycosylated because the enzyme will bind to ConA which has a specificity for high mannose structures. Also, the plant derived enzyme was chemically deglycosylated with TFMS (trifluoromethanesulfonic acid). The α-galactosidase appeared to be cleaved as observed by a shift in molecular weight on both a silver stained gel and a Western blot with α gal antibody. Early attempts to cleave rGal-A with PNGaseF to release N-linked carbohydrate have been unsuccessful suggesting the presence of α1,3 fucose on the terminal GlcNac of the carbohydrate side chain. This was verified by glycan analysis work carried out by the Glycobiology Core Group at University of California San Diego Cancer Center. Carbohydrate profiling and compositional analysis was done. NMR experiments confirmed that rGal-A from the plant IF contains an N-linked glycan containing plant-specific carbohydrate linkages of a β1,2 xylose and α1,3 fucose on the trimannosyl core. This N-linked structure has been previously reported to occur in glycoproteins isolated from plant seeds and tissue cultures. Five (5) ug was hydrolyzed with 2M TFA for 4 hours and analyzed by HPAEC-PAD. The total amount of sugar and sugar content was 560 ug and 12%. NMR analysis of the major peak showed a trimannosyl-chitobiose core, with α1,3 linked fucose and a β1,2 linked xylose.

α-galactosidase glycan structures were determined by MALDI-TOF and/or MALDI-MS in collaboration with the Universitaet fuer Bodenkultur, see Table 11. For MALDI, 5 μg of plant derived α-galactosidase was digested with pepsin in a mass ratio of 1:40 in 5% formic acid. After evaporation the peptides were dissolved in ammonium acetate buffer, pH 5.0, boiled and subsequently digested with PNGase A overnight. Since the sample has a mass of 49.000 g/mol, there are 100 pmol of glycoprotein. After evaporation, the peptides were removed by cation exchange chromatography and the glycans are analyzed by MALDI (or pyridylaminated).

The molecular mass of the glycan was determined by MALDI-MS using a ThermoBio Analysis DYNAMO (linear MALDI-TOF MS with delayed extraction) instrument. A small portion of the sample was dried on the sample target and subsequently overlaid with "matrix" (gentisic acid). The samples contained complex type sugar chains with fucose, xylose and varying amounts of terminal GlcNAc. Small fractions were devoid of fucose and therefore amenable to hydrolysis by PNGase F.

TABLE 11

| Glycan Structure | Molecular Weight Daltons | Lot #980805 % Glycan Structure | Lot #981215 % Glycan Structure |
|---|---|---|---|
| MOXF | 1050.5 | 3 | — |
| MMX | 1066.5 | 2 | 2 |
| MMXF | 1212.7 | 22 | 8 |
| Man 5 | 1237.5 | — | 1.8 |
| GnMX/MGnX | 1269.8 | 6 | 0.5 |
| GnMXF/MGnXF | 1416.4 | 53 | 16 |
| GnGnX | 1473.3 | 5 | 7 |
| GnGnXF | 1619.9 | 9 | 55 |

TABLE 12

| Characteristic | Plant Derived | CHO Cell Secreted |
|---|---|---|
| Number of Core Structures | 8 | 23 |
| Sialic Acid | Absent | Present |
| Xylose | β(1,2) Linkage | Absent |

TABLE 12-continued

| Characteristic | Plant Derived | CHO Cell Secreted |
|---|---|---|
| Fucose | α(1,3) Linkage | α(1,6) Linkage |
| % Complex Structures | | |
| % Weight Glycosylated | 10–12% | 15% |
| Specific Activity | | |

TABLE 13

| α-Galactosidase Source | Specific Activity 4-MU Substrate | Reference |
|---|---|---|
| Nicotiana benthamiana Human, Recombinant | $5.0 \times 10^6$ | This Patent Application |
| Human Spleen | $1.88 \times 10^6$ | Bishop and Desnick, 1981, J. Biol. Chem. 256 (3): 1307–1316 |
| Human Placenta | $0.99 \times 10^6$ | Bishop and Desnick, 1981, J. Biol. Chem. 256 (3): 1307–1316 |
| Human Plasma | $7.4 \times 10^5$ | Bishop and Sweeley, 1978, Biochim. Bioph. Acta, 525:399–409 |

This example demonstrates the ability to extract two different products from the same leaf tissue based upon extraction procedures that specifically target products localized in the apoplast and cytosol.

Conclusions

The following includes a number of aspects of the invention:

The present invention provides for a method for producing a protein of choice comprising a lysosomal enzyme which is enzymatically active, comprising: recovering the lysosomal enzyme from (i) a transgenic plant cell or (ii) a cell, tissue or organ of a transgenic plant, which transgenic plant cell or plant is transformed or transfected with a recombinant expression construct comprising a nucleotide sequence encoding the lysosomal enzyme and a promoter that regulates expression of the nucleotide sequence so that the lysosomal enzyme is expressed by the transgenic plant cell or plant. The promoter can be an inducible promoter. The inducible promoter can be induced by mechanical gene activation. The method can be carried out with the transgenic plant and additionally comprises a step of inducing the inducible promoter before or after the transgenic plant is harvested, which inducing step is carried out before recovering the lysosomal enzyme from the cell, tissue or organ of the transgenic plant. The lysosomal enzyme can be a modified lysosomal enzyme which is enzymatically active and comprises: (a) an enzymatically-active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions. The modified lysosomal enzyme can comprise a signal peptide or detectable marker peptide at the amino or carboxyl terminal of the modified lysosomal enzyme. The modified lysosomal enzyme can be recovered from (i) the transgenic plant cell or (ii) the cell, tissue or organ-of the transgenic plant by reacting with an antibody that binds the detectable marker peptide. The antibody can be a monoclonal antibody. The modified lysosomal enzyme can comprise: (a) an enzymatically-active fragment of an α.-N-acetylgalactosaminidise, acid lipase, α-galactosidase, glucocerebrosidase, α.-L-iduronidase, iduronak sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, iduronate sulfatase, α-mannosidase, sialidasc or (a) having one or more naturally-occurring amino acid additions, deletions or substitutions. The modified lysosomal enzyme can comprise: (a) an enzymatically-active fragment of a human glucocerebrosidase or human α-L-iduronidase enzyme; (b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions. The modified lysosomal enzyme can be a fusion protein comprising: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I); and the method comprises: (a) recovering the fusion protein from the transgenic plant cell, or the cell, tissue or organ of the transgenic plant; (b) treating the fusion protein with a substance that cleaves the cleavable linker so that (I)is separated from the cleavable linker and any sequence attached thereto; and (c) recovering the separated (I). The transgenic plant can be a transgenic tobacco plant. The lysosomal enzyme can be a human or animal lysosomal enzyme. The lysosomal enzyme can be an α-N-acetylgalactosaminidase, acid lipase, α-galactosidase, glucocerebrosidase, α-L-iduronidase, iduronate sulfatase, α-mannosidase or sialidese. The lysosomal enzyme can be a human glucocerebrosidase or human α-L-iduronidase. The organ can be a leaf, stem, root, flower, fruit or seed.

The present invention provides for a recombinant expression construct comprising a nucleotide sequence encoding a protein of choice comprising a lysosomal enzyme and a promoter that regulates the expression of the nucleotide sequence in a plant cell. The promoter can be an inducible promoter. The inducible promoter can be induced by mechanical gene activation. The lysosomal enzyme can be a modified lysosomal enzyme which is enzymatically active and comprises: (a) an enzymatically-active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions. The modified lysosomal enzyme can comprise a signal peptide or detectable marker peptide at the amino or carboxyl terminal of the modified lysosomal enzyme. The detectable marker peptide 15 comprises SEQ ID NO: 10. The modified lysosomal enzyme can comprise (a) an enzymatically-active fragment of an α-N-acetylgalactosaminidase, acid lipase, α-galactosidase, glucocerebrosidase, α-L-iduronidase, iduronate sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, α-mannosidase, sialidase or (a); or (c) the α-N-acetylgalactosaminidase, acid lipase, α-galactosidase, glucocerebrosidase, α-L-iduronidase, iduronate sulfatase, α-mannosidase, sialidase or (a) having one or more naturally-occurring amino acid additions, deletions or substitutions. The modified lysosomal enzyme can comprise (a) an enzymatically-active fragment of a human glucocerebrosidase or human α-L-iduronidase enzyme; (b) the human glucocerebrosidase or human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions. The modified lysosomal enzyme can be a fusion protein comprising can comprise: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I). The lysosomal enzyme can be a human or animal lysosomal enzyme. The lysosomal enzyme can be an α-N-acetylgalactosaminirdase, acid lipase, α-galactosidase, glucocerebrosidase, α-L-iduronidase, iduronate sulfatase, α-mannosidase or sialidase. The lysosomal enzyme can be a human glucocerebrosidase or human α-L-iduronidase.

The present invention provides for a plant transformation vector comprising any of the recombinant expression construct recited above.

The present invention provides for a plant which is transformed or transfected with any of the recombinant expression construct recited above.

The present invention provides for a plant cell, tissue or organ which is transformed or transfected with any of the recombinant expression construct recited above.

The present invention provides for a plant transfection vector comprising any-of the recombinant expression construct recited above.

The present invention provides for a plasmid comprising any of the recombinant expression construct recited above.

The present invention provides for a transgenic plant or plant cell capable of producing a lysosomal enzyme which is enzymatically active, which transgenic plant or plant cell is transformed or transfected with a recombinant expression construct comprising a nucleotide sequence encoding a lysosomal enzyme and a promoter that regulates expression of the nucleotide sequence in the transgenic plant or plant cell. The promoter is an inducible promoter. The inducible promoter is induced by mechanical gene activation. The inducible promoter comprises SEQ ID NO: 5. The lysosomal enzyme which is a modified lysosomal enzyme which is enzymatically active and which comprises: (a) an enzymatically-active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid additions, deletions or substitutions. The modified lysosomal enzyme comprises a signal peptide or detectable marker peptide at the amino or carboxyl terminal of the modified lysosomal enzyme. The detectable marker peptide can comprise SEQ ID NO: 10. The modified lysosomal enzyme comprises: (a) an enzymatically-active fragment of an α-N-acetylgalactosaminidase, acid lipase, α-galactosidase, glucocerebrosidase, α-L-iduronidase, iduronate sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, amannosidase, sialidase or (a); or (c) the α-N-acetylgalactosarriinidase, acid lipase, α-galactosidase, glucocerebrosidase, α-L-iduronidase, iduronate sulfatase, α-mannosidase, sialidase or (a) having one or more naturally-occurring amino acid additions, deletions or substitutions. The modified lysosomal enzyme comprises: (a) an enzymatically-active fragment of a human glucocerebrosidase or human α-L-iduronidase enzyme; (b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions. The modified lysosomal enzyme is a fusion protein comprising: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (II) a cleavable linker fused to the amino or carboxyl terminus of (I). The transgenic plant or plant cell is a transgenic tobacco plant or tobacco cell. The lysosomal enzyme is a human or animal lysosomal enzyme. The lysosomal enzyme is an α-N-acetylgalactosaminidase, acid lipase, α-galactosidase, glucocerebrosidase, α-L-iduronidase, iduronate sulfatase, α-mannosidase or sialidase. The lysosomal enzyme is a human glucocerebrosidase or human α-L-iduronidase.

The present invention provides for a leaf, stem, root, flower or seed of any of the transgenic plant recited above.

The present invention provides for a seed of plant line Nicotiana sp., which seed has the ATCC Accession No. PTA-2258, deposited Jul. 25, 2000.

The present invention provides for a plant grown from the seed recited above.

The present invention provides for a lysosomal enzyme which is enzymatically active and is produced according to a process comprising: recovering the lysosomal enzyme from (i) a transgenic plant cell or (ii) a cell, tissue or organ of a transgenic plant which transgenic plant cell or plant is transformed or transfected with a recombinant expression construct comprising a nucleotide sequence encoding the lysosomal enzyme and a promoter that regulates expression of the nucleotide sequence so that the lysosomal enzyme is expressed by the transgenic plant cell or plant. The promoter can be an inducible promoter. The process is carried out with the transgenic plant and additionally can comprise a step of inducing the inducible promoter before or after the transgenic plant is harvested, which inducing step is carried out before recovering the lysosomal enzyme from the cell, tissue or organ of the transgenic plant. The modified lysosomal enzyme which can be enzymatically active and can comprise: (a) an enzymatically-active fragment of a human or animal lysosomal enzyme; (b) the human or animal lysosomal enzyme or (a) having one or more amino acid residues added to the amino or carboxyl terminus of the human or animal lysosomal enzyme or (a); or (c) the human or animal lysosomal enzyme or (a) having one or more naturally-occurring amino acid, additions, deletions or substitutions. The modified lysosomal enzyme can comprise a signal peptide or detectable marker peptide at the amino or carboxyl terminal of the modified lysosomal enzyme. The modified lysosomal enzyme can comprise: (a) an enzymatically-active fragment of an α-N-acetylgalactosaminidase, acid lipase, α-galactosidase, glucocerebrosidase, α-L-iduronidase, iduronate sulfatase, α-mannosidase or sialidase; (b) the α-N-acetylgalactosaminidase, acid lipase, α-galactosidase, glucocerebrosidase, α-L-iduronidase, iduronate sulfatase, α-mannosidase, sialidase or (a) having one or more amino acid residues added to the amino or carboxyl terminus of the α-N-acetylgalactosaminidase, acid lipase, α-galactosidase, glucocerebrosidase, α-L-iduronidase, iduronate sulfatase, amannosidase, sialidase or (a); or (c) the α-N-acetylgalactosaminidasd, acid lipase, α-galactosidase, glucocerebrosidase, α-L-iduronidase, iduronate sulfazase, α-mannosidase, sialidase or (a) having one or more naturally-occurring amino acid additions, deletions or substitutions. The modified lysosomal enzyme comprises: (a) an enzymatically-active fragment of a human glucocerebrosidase or human α-L-iduronidase enzyme; (b) the human glucocerebrosidase, human α-L-iduronidase or (a) having one or more amino acid residues added to the amino or carboxyl terminus of the human glucocerebrosidase, human α-L-iduronidase or (a); or (c) the human glucocerebrosidase, human α-L-iduronidase or (a) having one or more naturally-occurring amino acid additions, deletions or substitutions. The modified lysosomal enzyme can be a fusion protein comprising: (I) (a) the enzymatically-active fragment of the human or animal lysosomal enzyme, (b) the human or animal lysosomal enzyme, or (c) the human or animal lysosomal enzyme or (a) having one or more naturally-occurring amino acid additions, deletions or substitutions, and (H) a cleavable linker fused to the amino or carboxyl terminus of (I). The transgenic plant can be a transgenic tobacco plant. The lysosomal enzyme can be a human or animal lysosomal enzyme. The lysosomal enzyme can be an α-N-acetylgalactosaminidase, acid lipase, α-galactosidase, glucocerebrosidase, α-L-iduronidase, iduronate sulfatase, α-mannosidase or sialidase. The lysosomal enzyme can be a human glucocerebrosidase or human α-L-iduronidase. The organ can be a leaf, stem, root, flower, fruit or seed.

LITERATURE CITED

1. Brady, R. O. Fabry Disease, In: Peripheral Neropathym 3rd ed., J. W. Griffin, P. A. Low, and J. F. Poduslo (eds.) W. B. Saunders. pp. 1169, 1993.
2. Desnick, R. J., Ioannou, Y. A., and Eng, C. M. Alpha-Galactosidase A Deficiency: Fabry Disease, In: The Metabolic Bases of Inherited Diseases, C. R. Scriver, A. L. Beaudet, W. S. Sly, D. Valle (eds.) McGraw-Hill, pp. 2741, 1995.
3. Brady, R. O. Sphingolipidoses, a Medical Progress Report. N. Engl. J. Med. 275: 312, 1966.
4. Brady R. O., Pentchev P. G., Gal A. E., Hibbert S. R., and Dekaban A. S. Replacement therapy for inherited enzyme deficiency: Use of purified glucocerebrosidase in Gaucher's disease. N. Engl. J. Med. 291:989, 1974.
5. Furbish F. S., Blair H. E., Shiloach J., Pentchev P. G., and Brady R. O. Enzyme replacement therapy in Gaucher's disease: Large-scale purification of glucocerebrosidase suitable for human administration. Proc. Natl. Acad. Sci. USA 74: 560, 1977.
6. Furbish F. S., Steer C. J., Krett N. L., and Barranger, J. A. Uptake and distribution of placental glucocerebrosidase in rat hepatic cells and effects of sequential deglycosylation. Biochim. Biophys. Acta 673: 425, 1981.
7. Barton, N. W., Furbish, F. S., Murray, G. J., Garfield, M., and Brady, R. O. Therapeutic response to intravenous infusions of glucocerebrosidase in a patient with Gaucher disease. Proc. Natl. Acad. Sci. USA 87: 1913, 1990.
8. Barton, N. W, Brady, R. O., Dambrosia, J. M., DiBisceglie, A. M., Doppelt, S. H., Hill, S. C., Mankin, H. J., Murray, G. J., Parker, R. I., Argoff, C. E., Grewal, R. P., and Yu, K-T. Replacement therapy for inherited enzyme deficiency-nacrophage-targeted glucocerebrosidase for Gaucher's disease. N. Engl. J. Med. 324: 1464, 1991.
9. Parker, R. I., Barton, N. W., Read, E. J., and Brady, R. O. Hematologic improvement in a patient with Gaucher's disease on long-term replacement therapy: Evidence for decreased splenic sequestration and improved red blood cell survival. Am. J. Hematol. 38: 130, 1991.
10. Hill, S. C., Parker, C. C., Brady, R. O., and Barton, N. W. MRI of multiple platyspondyly in Gaucher disease: Response to enzyme replacement therapy. J. Comput. Assist. Tomog. 17: 806, 1993.
11. Beutler, E., Kay, A., Saven, A., Garver, P., Thurston, D., Dawson, A., and Rosenbloom, B. Enzyme replacement therapy for Gaucher disease. Blood 78:1183, 1991.
12. Fallet, S., Grace, M. E., Sibille, A., Mendelson, D. S., Shapiro, R. S., Hermann, G., and Grabowski, G. A. Enzyme augmentation in moderate to life-threatening Gaucher disease. Pediatr. Res. 31: 496, 1992.
13. Mistry, P. K., Davies, S., Corfield, A., Dixon, A. K., and Cox, T. M. Successful treatment of bone marrow failure in Gaucher's disease with low-dose modified glucocerebrosidase. Quart. J. Med. New Series 84: 541, 1992.
14. Grabowski, G. A., Barton, N. W., Pastores, G.,Dambrosia, J. M., Baneijee, T. K., McKee, M. A., Parker, C., Schiffinann, R., Hill, S. C., Brady, R. O. Enzyme therapy in Type I Gaucher disease: Comparative efficacy of mannose-terminated glucocerebrosidase from natural and recombinant sources. Ann. Inter. Med. 122:33, 1995.
15. Hasholt L., Sorensen, S. A. A microtechnique for quantitative mesurements of acid hydrolases in fibroblasts. Its application in diagnosis of Fabry disease and enzyme replacement studies. Clin. Chim. Acta 142:257, 1984.
16. Mapes, C. A., Anderson, R. L., Sweeley, C. C., Desnick, R. J., Krivit, W. Enzyme replacement in Fabry's disease, an inborn error of metabolism. Science 169:987, 1970.
17. Brady, R. O., Tallman, J. F., Johnson, W. G., Gal, A. E., Leahy, W. R., Quirk, J. M., Dekaban, A. S. Replacement therapy for inherited enzyme deficiency: Use of purified ceramidetrihexosidease in Fabry's disease. N. Eng. J. Med. 289:9, 1973.
18. Desnick, R. J., Dean, K. J., Grabowski, G. A., Bishop, D. F., Sweeley, C. C. Enzyme therapy XII: Enzyme therapy in Fabry's disease: Differential enzyme and substrate clearance kinetics of plasma and splenic Alpha-galactosidase isozymes. Proc. Natl. Acad. Sci USA 76:5326, 1979.

19. Beutler, E. The cost of treating Gaucher disease. Nature Medicine 2:523, 1996.
20. NIH Technology Assessment Panel on Gaucher Disease. Gaucher Disease: Current issues in diagnosis and treatment. JAMA 275:548, 1995.
21. Hiatt, A., Cafferkey, R., and Bowdish, K. Production of antibodies in transgenic plants. Nature 342:76, 1989.
22. Assembly of multimeric proteins in plant cells: Characteristics and uses of plant-derived antibodies, In: Transgenic Plants, Fundamentals and Applications, A. Hiatt, (ed.) Marcel Dekker, Inc. New York, N.Y. pp. 221, 1992.
23. Ma, J. K.-C., and Hein, M. B. Plant antibodies for immunotherapy. Plant Physiol. 109:341, 1995.
25 Sijmons, P. C., Dekker, B. M. M., Schrammeijer, B., Verwoerd, T. C., van den Elzen, P. J. M., and Hoekema, A. Production of correctly processed human serum albumin in transgenic plants. Bio/Technology 8:217, 1990.
26 Mason, H. S., Lam D. M.-K., and Arntzen, C. J. Expression of hepatitis B surface antigen in transgenic plants. Proc. Natl. Acad. Sci. USA 89:11745, 1992.
27 Haq, T. A., Mason, H. S., Clements, J. D., and Arntzen, C. J. Oral immunization with a recombinant bacterial antigen produced in transgenic plants. Science 268:714, 1995.
28 Turpen, T. H., Reint, S. J., Charoenvit, Y., Hoffman, S. L., Fallarme, V., and Grill, L. K. Malarial epitopes expressed on the surface of recombinant tobacco mosaic virus. Bio/Technology 13:53, 1995.
29 Kumagai, M. H., Turpen, T. H., Weinzettl, N., della-Cioppa, G., Turpen, A. M., Donson, J., Hilf, M. E., Grantham, G. L., Dawson, W. O., Chow, T. P., Piatak Jr., M., and Grill, L. K. Rapid, high level expression of biologically active α-trichosanthin in transfected plants by a novel RNA viral vector. Proc. Natl. Acad. Sci. USA 90:427, 1993.
30 Turpen, T. H., and Dawson, W. O Amplification, movement and expression of genes in plants by viral-based vectors, In: Transgenic Plants, Fundamentals and Applications, A. Hiatt, (ed.) Marcel Dekker, Inc. New York, N.Y. pp. 195, 1992.
31 Sugimoto, Y., Aksentijevich, I., Murray, G. J., Brady, R. O., Pastan, I., and Gottesman, M. M. Retroviral coexpression of a multidrug resistance gene (MDRI) and human Alpha-galactosidase A for gene therapy of Fabry disease. Human Gene Therapy 6:905, 1995.
32 O'Neill, S. D., Kumagai, M. H., Majumndar, A., Huang, N., Sutliff, T. D. and Rodriguez, R. L. The (α-amylase genes in Oryza sativa: Characterization of cDNA clones and mRNA expression during seed germination. Mol. Gen. Genet. 221:235, 1990.
33 Kumagai, M. H., Shah, M., Terashima, M., Vrkljan, Z., Whitaker, J. R., and Rodriguez, R. L. Expression and secretion of rice α-amylase by Saccharomyces cerevisiae. Gene 94:209, 1990.
34 Suzuki, K. Enzymatic diagnosis of sphingolipidoses. Meth. Enzy. 138:727, 1987.
35 Chrispeels, M. J. Sorting of proteins in the secretory system. Annu. Rev. Plant Physiol. Plant Mol. Biol. 42:21, 1991.
36 Ioannou, Y. A., Bishop, D. F., and Desnick, R. J. Overexpression of human Alpha-galactosidase A results in its intracellular aggregation, crystallization in lysosomes, and selective secretion. J. Cell Biol. 119:1137, 1992.
37 Dombrowski, J. E., and Raikhel, N. V. Protein targeting to the plant vacuole—a historical perspective. Brazilian Journal of Medical and Biological Research 29:413, 1996.

38 Kermode, A. R. Mechanisms of intracellular protein transport and targeting in plant cells. Crit. Rev. Plant Sci. 15:285, 1996.
39 Bishop, D. F., Calhoun, D. H., Bernstein, H. S., Hantzopoulos, P., Quinn, M., and Desnick, R. J. Human Alpha-galactosidase A: Nucleotide sequence of a cDNA clone encoding the mature enzyme. Proc. Natl. Acad. Sci. USA 83:4859, 1986.
40 Quinn, M., Hantzopoulos, P., Fidanza, V. and Calhoun, D. H. A genomic clone containing the promoter for the gene encoding the human lysosomal enzyme, Alpha-galactosidase A. Gene 58:177, 1987.
41 Coppola, G., Yan, Y., Hantzopoulos, P., Segura, E., Stroh, J. G., and Calhoun, D. H. Characterization of glycosylated and catalytically active recombinant human Alpha-galactosidase A using a baculovirus vector. Gene 144:197.
42 Miyamnura, N., Araki, E., Matsuda, K., Yoshimura, R., Furukawa, N., Tsuruzoe, K., Shirotani, T., Kishikawa, H., Yamaguchi, K., and Shichiri, M. A carboxy-terminal truncation of human Alpha-galactosidase A in a heterozygous female with Fabry disease and modification of the enzymatic activity by the carboxy-terminal domain. J. Clin. Invest. 18009, 1996.
43 National Research Council. Putting biotechnology to work. Bioprocess engineering. National Academy Press, Washington, D.C. 1992.
44 Prescribing Information, Ceredase™, (alglucerase injection). Genzyme Corporation, January 1995.
45 Wilkins, T., Bednarek, S. Y., Raikhel, N. V. Role of propetide glycan in post-translational processing and transport of barley lectin to vacuoles in transgenic tobacco. Plant Cell 2:301, 1990.
46 Melchers, L. S., Sela-Buurlage, M. B., Vloemans, S. A., Woloshuk, C. P., Van Roekel, J. S. C., Pen, J., Van den Elzen, P. J. M., Cornelissen, B. J. C. Extracellular targeting of the vacuolar tobacco proteins AP24, chitinase and β-1,3-glucanase in transgenic plants. Plant Mol. Biol. 21:583, 1993.
47 Sato, F., Koiwa, H., Sakai, Y., Kato, N., Yamada, Y. Synthesis and secretion of tobacco neutral PR-5 protein by transgenic tobacco and yeast. Biochem. Biophys. Res. Comm. 211:909,1995.
48 Maggio, A., D'Urzo, M. P., Abad, L. R., Takeda, S., Hasegawa, P. M., and Bressan, R. Large quantities of recombinant PR-5 proteins from the extracellular matrix of tobacco: Rapid production of microbial-recalcitrant proteins. Plant Mol. Biol. Rep. 14:249, 1996.
49 Calhoun, D. H., Bishop, D. F., Bernstein, H. S., Quinn, M., Hantzopoulos, P., Desnick, R. J. Fabry disease: Isolation of a cDNA clone encoding human Alpha-galactosidase A. Proc. Natl. Acad. Sci. USA 82:7364, 1985.
50 Jenkins, N., Parekh, R. B., James, D. C. Getting the glycosylation right: Implications for the biotechnology industry. Nature Biotech. 14:975, 1996.
51 Fitchette-Lainé, A-C., Gomord, V., Chekkafi, A., and Faye, L. Distribution of xylosylation and fucosylation in the plant Golgi apparatus. Plant J. 5:673, 1994.
52 Hein, M. B., Tang, Y., McLeod, D. A., Janda, K. D., Hiatt, A. C. Evaluation of immunoglobulins from plant cells. Biotechnol. Prog. 7:455, 1991.
53 Garcia-Casado, G. Sanchez-Monge, R., Chrispeels, M. J., Armentia, A., Salcedo, G., and Gomez, L. Role of complex asparagine-linked glycans in the allergenicity of plant glycoproteins. Glycobiol. 6:471, 1996.
54 Chrispeels, M. J., and Faye, L. The production of recombinant glycoproteins with defined non-immunogenic glycans, In: Transgenic Plants, A production system for industrial and pharmaceutical proteins. M. R. L. Owen and J. Pen, (eds.) John Wiley & Sons Ltd. pp. 99, 1996.
55 von Schaewen, A., Strum, A., O'Neill, J., Chrispeels, M. J. Isolation of a mutant Arabidopsis plant that lacks N-acetyl glucosaminyl transferase I and is unable to synthesize golgi-modified complex N-linked glycans. Plant Physiol. 102:1109, 1993.
56 Takasaki, S., Murray, G. J., Furbish, F. S., Brady, R. O., Bainanger, J. A., and Kobata, A. Structure of the N-asparagine-linked oligosaccharide units of human placental α-glucocerebrosidase. J. Biol. Chem. 259:10112, 1984.
57 Murray, G. J., Lectin-specific targeting of lysosomal enzymes to reticuloendothelial cells. Meth. Enzy. 149:25, 1987.
58 Ohshima, T., Murray, G. J., Nagle, J. W., Quirk, J. M., Kraus, M. H., Barton, N. W., Brady, R. O., and Kulkarni, A. B. Structural organization and expression of the mouse gene encoding Alpha-galactosidase A. Gene 166:277, 1995.
59 Horsch et al., Science 227 (1985) 1229–1231.
60 An, G., Watson, B D, Chiang, C C Plant Physiol 81 (1986) 301–305.
61 Gelvin, S B, Schilperoort, R A (eds.) Plant Molec Biol Manual (1988).
62 Kint, 1971, Arch. Int. Physiol. Biochem. 79:633–644.
63 Beutler & Kuhl, 1972, Amer. J. Hum. Genet. 24:237–249.
64 Romeo, et al., 1972, FEBS Lett. 27:161–166.
65 Wood & Nadler, 1972, Am. J. Hum. Genet. 24:250–255.
66 Ho, et al., 1972, Am. J. Hum. Genet. 24:256–266.
67 Desnick, et al., 1973, J. Lab. Clin. Med. 81:157–171.
68 Desnick, et al., 1989, in The Metabolic Basis of Inherited Disease, Scriver, C. R.,
69 Beaudet, A. L. Sly, W. S. and Valle, D., eds, pp. 1751–1796, McGraw Hill, N.Y.
70 Kint, 1971; Arch. Int. Physiol. Biochem. 79:633–644).
71 Beutler & Kuhl, 1972, J. Biol. Chem. 247: 7195–7200;
72. Callahan, et al., 1973, Biochem. Med. 7: 424431.
73. Dean, et al., 1977, Biochem. Biophys. Res. Comm. 77:1411–1417.
74. Schram, et al., 1977, Biochim. Biophys. Acta. 482:138–144.
75. Kusiak, et al., 1978, J. Biol. Chem. 253:184–190.
76. Dean, et al., 1979, J. Biol. Chem. 254:10001–10005.
77. Bishop, et al., 1980, in Enzyme Therapy in Genetic Disease:2, Desnick, R. J., ed., pp. 17–32, Alan R. Liss, Inc., New York.
78. Beutler & Kuhl, 1972, J. Biol. Chem. 247:7195–7200.
79. Schram, et al., 1977, Biochim. Biophys. Acta. 482:138–144).
80. Kint, 1971; Arch. Int. Physiol. Biochem. 79: 633–644.
81. Beutler & Kuhl, 1972, Amer. J. Hum. Genet. 24:237–249.
82. Romeo, et al., 1972, FEBS Lett. 27:161–166.
83. Wood & Nadler, 1972, Am. J. Hum. Genet. 24:250–255.
84. Ho, et al., 1972, Am. J. Hum. Genet. 24:256–266.
85. Desnick, et al., 1973, J. Lab. Clin. Med. 81:157–171.
86. Desnick, et al., 1989, in The Metabolic Basis of Inherited Disease, Scriver, C. R.,
87. Beaudet, A. L. Sly, W. S. and Valle, D., eds, pp. 1751–1796, McGraw Hill, N.Y.
88. Beutler & Kuhl, 1972, J. Biol. Chem. 247:7195–7200.

The present invention is not to be limited to scope by the biological material deposited since the deposited embodiments are intended as illustrations of the individual aspects of the invention, and any biological material, or constructs which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein; these ate incorporated by reference in their entirety.

What is claimed is:

1. A recombinant expression construct comprising:
    a nucleotide sequence encoding a mammalian lysosomal enzyme and a promoter that regulates the expression of the nucleotide sequence in a plant cell;
    wherein the lysosomal enzyme is lipase.

2. A recombinant expression construct comprising:
    a nucleotide sequence encoding a mammalian lysosomal enzyme and a promoter that regulates the expression of the nucleotide sequence in a plant cell;
    wherein said recombinant expression construct is a recombinant viral expression construct, and the lysosomal enzyme is lipase.

3. A recombinant expression construct comprising:
    a nucleotide sequence encoding a mammalian lysosomal enzyme and a promoter that regulates the expression of the nucleotide sequence in part cell; and
    wherein the lysosomal enzyme is glucocerebrosidase.

4. A recombinant plant viral expression construct comprising a nucleotide sequence encoding a human lysosomal enzyme and a promoter that regulates the expression on the nucleotide sequence in a plant cell, in which the human lysosomal enzyme is a human .alpha.-L-iduronidase.

5. A plant or plant cell which is transfected with a recombinant plant viral expression that comprising a nucleotide sequence encoding a human lysosomal enzyme and a promoter that regulates the expression of the nucleotide sequence in which the lysosomal enzyme is a human .alpha.-L-iduronidase.

6. A leaf, stem, root, flower or a seed of the plant of claim 5.

7. A method for producing a human glucocerebrosidase which is enzymatically active, comprising:
    recovering the human glucocerebrosidase from (i) a transgenic plant cell or (ii) a cell, tissue or organ of a transgenic plant, which transgenic plant cell or plant is transformed with a recombinant expression construct comprising a nucleotide sequence encoding the human glucocerebrosidase and a promoter that regulates expression of the nucleotide sequence so that the human glucocerebrosidase is expressed by the transgenic plant cell or plant.

* * * * *

```
                        SEQUENCE LISTING

<160> NUMBER OF SEQ ID NOS: 18

<210> SEQ ID NO 1
<211> LENGTH: 15
<212> TYPE: PRT
<213> ORGANISM: rice

<400> SEQUENCE: 1

Ser Asn Leu Thr Ala Gly Met Leu Asp Asn Gly Leu Ala Arg Thr
1               5                   10                  15

<210> SEQ ID NO 2
<211> LENGTH: 14
<212> TYPE: PRT
<213> ORGANISM: Homo sapiens

<400> SEQUENCE: 2

Asp Ile Pro Gly Ala Arg Ala Leu Asn Gly Leu Ala Arg Thr
1               5                   10

<210> SEQ ID NO 3
<211> LENGTH: 30
<212> TYPE: PRT
<213> ORGANISM: Homo sapiens

<400> SEQUENCE: 3

Thr Ser Arg Leu Arg Ser His Ile Asn Pro Thr Gly Thr Val Leu Leu
1               5                   10                  15

Gln Leu Glu Asn Thr Met Gln Met Ser Leu Lys Asp Leu Leu
            20                  25                  30

<210> SEQ ID NO 4
<211> LENGTH: 36
<212> TYPE: PRT
<213> ORGANISM: Homo sapiens

<400> SEQUENCE: 4

Thr Ser Arg Leu Arg Ser His Ile Asn Pro Thr Gly Thr Val Leu Leu
1               5                   10                  15

Gln Leu Glu Asn Thr Met Gln Met Ser Leu Lys Asp Leu Leu Ser Glu
            20                  25                  30

Lys Asp Glu Leu
            35

<210> SEQ ID NO 5
<211> LENGTH: 26
<212> TYPE: PRT
<213> ORGANISM: Homo sapiens

<400> SEQUENCE: 5

Thr Ser Arg Leu Arg Ser His Ile Asn Pro Thr Gly Thr Val Leu Leu
1               5                   10                  15

Gln Leu Glu Asn Thr Met Gln Met Ser Leu
            20                  25
```

```
<210> SEQ ID NO 6
<211> LENGTH: 32
<212> TYPE: PRT
<213> ORGANISM: Homo sapiens

<400> SEQUENCE: 6

Thr Ser Arg Leu Arg Ser His Ile Asn Pro Thr Gly Thr Val Leu Leu
1               5                   10                  15
Gln Leu Glu Asn Thr Met Gln Met Ser Leu Ser Glu Lys Asp Glu Leu
            20                  25                  30

<210> SEQ ID NO 7
<211> LENGTH: 22
<212> TYPE: PRT
<213> ORGANISM: Homo sapiens

<400> SEQUENCE: 7

Thr Ser Arg Leu Arg Ser His Ile Asn Pro Thr Gly Thr Val Leu Leu
1               5                   10                  15
Gln Leu Glu Asn Thr Met
            20

<210> SEQ ID NO 8
<211> LENGTH: 28
<212> TYPE: PRT
<213> ORGANISM: Homo sapiens

<400> SEQUENCE: 8

Thr Ser Arg Leu Arg Ser His Ile Asn Pro Thr Gly Thr Val Leu Leu
1               5                   10                  15
Gln Leu Glu Asn Thr Met Ser Glu Lys Asp Glu Leu
            20                  25

<210> SEQ ID NO 9
<211> LENGTH: 18
<212> TYPE: PRT
<213> ORGANISM: Homo sapiens

<400> SEQUENCE: 9

Thr Ser Arg Leu Arg Ser His Ile Asn Pro Thr Gly Thr Val Leu Leu
1               5                   10                  15
Gln Leu

<210> SEQ ID NO 10
<211> LENGTH: 24
<212> TYPE: PRT
<213> ORGANISM: Homo sapiens

<400> SEQUENCE: 10

Thr Ser Arg Leu Arg Ser His Ile Asn Pro Thr Gly Thr Val Leu Leu
1               5                   10                  15
Gln Leu Ser Glu Lys Asp Glu Leu
            20

<210> SEQ ID NO 11
<211> LENGTH: 5
<212> TYPE: PRT
<213> ORGANISM: Homo sapiens

<400> SEQUENCE: 11

Thr Ser Arg Leu Arg
1               5
```

```
<210> SEQ ID NO 12
<211> LENGTH: 11
<212> TYPE: PRT
<213> ORGANISM: Homo sapiens

<400> SEQUENCE: 12

Thr Ser Arg Leu Arg Ser Glu Lys Asp Glu Leu
1               5                   10

<210> SEQ ID NO 13
<211> LENGTH: 11641
<212> TYPE: DNA
<213> ORGANISM: Tobacco mosaic virus

<400> SEQUENCE: 13 gtattttac  aacaattacc  aacaacaaca  aacaacaaac  aacattacaa  ttactattta      60
caattacaat  ggcatacaca  cagacagcta  ccacatcagc  tttgctggac  actgtccgag     120
gaaacaactc  cttggtcaat  gatctagcaa  agcgtcgtct  ttacgacaca  gcggttgaag     180
agtttaacgc  tcgtgaccgc  aggcccaagg  tgaacttttc  aaaagtaata  agcgaggagc     240
agacgcttat  tgctacccgg  gcgtatccag  aattccaaat  tacattttat  aacacgcaaa     300
atgccgtgca  ttcgcttgca  ggtggattgc  gatctttaga  actggaatat  ctgatgatgc     360
aaattcccta  cggatcattg  acttatgaca  taggcgggaa  ttttgcatcg  catctgttca     420
agggacgagc  atatgtacac  tgctgtatgc  ccaacctgga  cgttcgagac  atcatgcggc     480
acgaaggcca  gaaagacagt  attgaactat  acctttctag  gctagagaga  gggggaaaa     540 cagtccccaa  cttccaaaag  gaagcatttg  acagatacgc  agaaattcct  gaagacgctg     600
tctgtcacaa  tacttcccag  acaatgcgac  atcagccgat  gcagcaatca  ggcagagtgt     660
atgccattgc  gctacacagc  atatatgaca  taccagccga  tgagttcggg  gcggcactct     720
tgaggaaaaa  tgtccatacg  tgctatgccg  ctttccactt  ctctgagaac  ctgcttcttg     780
aagattcata  cgtcaatttg  gacgaaatca  acgcgtgttt  tcgcgcgat  ggagacaagt     840 tgacctttc  ttttgcatca  gagagtactc  ttaattattg  tcatagttat  tctaatattc     900
ttaagtatgt  gtgcaaaact  tacttcccgg  cctctaatag  agaggtttac  atgaaggagt     960
ttttagtcac  cagagttaat  acctggtttt  gtaagttttc  tagaatagat  acttttctt    1020 tgtacaaagg  tgtggcccat  aaaagtgtag  atagtgagca  gttttatact  gcaatggaag    1080
acgcatggca  ttacaaaaag  acttcttgcaa  tgtgcaacag  cgagagaatc  ctccttgagg    1140
attcatcatc  agtcaattac  tggtttccca  aaatgaggga  tatggtcatc  gtaccattat    1200
tcgacatttc  tttggagact  agtaagagga  cgcgcaagga  agtcttagtg  tccaaggatt    1260
tcgtgtttac  agtgcttaac  cacattcgaa  cataccaggc  gaaagctctt  acatacgcaa    1320
atgttttgtc  ctttgtcgaa  tcgattcgat  cgagggtaat  cattaacggt  gtgacagcga    1380
ggtccgaatg  ggatgtggac  aaatctttgt  tacaatcctt  gtccatgacg  ttttacctgc    1440
atactaagct  tgccgttcta  aaggatgact  actgattag  caagtttagt  ctcggttcga    1500
aaacggtgtg  ccagcatgtg  tgggatgaga  tttcgctggc  gtttgggaac  gcatttcct    1560 ccgtgaaaga  gaggctcttg  aacaggaaac  ttatcagagt  ggcaggcgac  gcattagaga    1620
tcagggtgcc  tgatctatat  gtgaccttcc  acgacagatt  agtgactgag  tacaaggcct    1680
ctgtggacat  gcctgcgctt  gacattagga  agaagatgga  agaaacggaa  gtgatgtaca    1740
atgcactttc  agagttatcg  gtgttaaggg  agtctgacaa  attcgatgtt  gatgttttt    1800
```

-continued

```
cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc tttggtagtt acctcaagag    1980
aagttgaaga accgtccatg aagggttcga tggccagagg agagttacaa ttagctggtc    2040
ttgctggaga tcatccggag tcgtcctatt ctaagaacga ggagatagag tctttagagc    2100
agtttcatat ggcaacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag gaagtatcat gtggcgcttt    2400
tggaatatga tgagcagggt gtggtgacat gcgatgattg gagaagagta gctgtcagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
ggaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa acccttgcat ggcaagatcc    3120
tgacttttac ccaatcggat aaagaagctc tgctttcaag agggtattca gatgttcaca    3180
ctgtgcatga agtgcaaggc gagacatact ctgatgtttc actagttagg ttaaccccta    3240
caccagtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat ttcattgaat gtcaaagatt    3600
gcatattgga tatgtctaag tctgttgctg cgcctaagga tcaaatcaaa ccactaatac    3660
ctatggtacg aacggcggca gaaatgccac gccagactgg actattggaa aatttagtgg    3720
cgatgattaa aaggaacttt aacgcacccg agttgtctgg catcattgat attgaaaata    3780
ctgcatcttt agttgtagat aagttttttg atagttattt gcttaaagaa aaagaaaac    3840 caaataaaaa tgtttctttg ttcagtagag agtctctcaa tagatggtta gaaaagcagg    3900
aacaggtaac aataggccag ctcgcagatt tgattttgt agatttgcca gcagttgatc    3960
agtacagaca catgattaaa gcacaaccca agcaaaaatt ggacacttca atccaaacgg    4020
agtacccggc tttgcagacg attgtgtacc attcaaaaaa gatcaatgca atatttggcc    4080
cgttgtttag tgagcttact aggcaattac tggacagtgt tgattcgagc agattttgt    4140 ttttcacaag aaagacacca gcgcagattg aggatttctt cggagatctc gacagtcatg    4200
```

-continued

```
tgccgatgga tgtcttggag ctggatatat caaaatacga caaatctcag aatgaattcc    4260
actgtgcagt agaatacgag atctggcgaa gattgggttt tgaagacttc ttgggagaag    4320
tttgaaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcagaggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgctttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtaatgatc ggtcagtgcc gaacaagaac tatagaaatg ttaaggattt tggaggaatg    5640
agttttaaaa agaataattt aatcgatgat gattcggagg ctactgtcgc cgaatcggat    5700 tcgtttaaa tagatcttac agtatcacta ctccatctca gttcgtgttc ttgtcattaa    5760
tatgcaggtg ctgaacacca tggtgaacaa acacttcttg tcccttttcgg tcctcatcgt    5820 cctccttggc ctctcctcca acttgacagc cggcatgctg acaatggat tggcaaggac    5880 gcctaccatg ggctggctgc actgggagcg cttcatgtgc aaccttgact gccaggaaga    5940
gccagattcc tgcatcagtg agaagctctt catggagatg gcagagctca tggtctcaga    6000
aggctggaag gatgcaggtt atgagtacct ctgcattgat gactgttgga tggctcccca    6060
aagagattca gaaggcagac ttcaggcaga ccctcagcgc tttcctcatg ggattcgcca    6120
gctagctaat tatgttcaca gcaaaggact gaagctaggg atttatgcag atgttggaaa    6180
taaaacctgc gcaggcttcc ctgggagttt tggatactac gacattgatg cccagacctt    6240
tgctgactgg ggagtagatc tgctaaaatt tgatggttgt tactgtgaca gtttggaaaa    6300
tttggcagat ggttataagc acatgtcctt ggccctgaat aggactggca gaagcattgt    6360
gtactcctgt gagtggcctc tttatatgtg gccctttcaa aagcccaatt atacagaaat    6420
ccgacagtac tgcaatcact ggcgaaattt tgctgacatt gatgattcct ggaaaagtat    6480
aaagagtatc ttggactgga catcttttaa ccaggagaga attgttgatg ttgctggacc    6540
```

-continued

```
aggggttgg aatgacccag atatgttagt gattggcaac tttggcctca gctggaatca    6600
gcaagtaact cagatggccc tctgggctat catggctgct cctttattca tgtctaatga    6660
cctccgacac atcagccctc aagccaaagc tctccttcag gataaggacg taattgccat    6720
caatcaggac cccttgggca agcaagggta ccagcttaga cagggagaca actttgaagt    6780
gtgggaacga cctctctcag gcttagcctg ggctgtagct atgataaacc ggcaggagat    6840
tggtggacct cgctcttata ccatcgcagt tgcttccctg ggtaaaggag tggcctgtaa    6900
tcctgcctgc ttcatcacac agctcctccc tgtgaaaagg aagctagggt tctatgaatg    6960
gacttcaagg ttaagaagtc acataaatcc cacaggcact gttttgcttc agctatctga    7020
aaaggacgaa ttatgaccta ggctcgcaaa gtttcgaacc aaatcctcaa aaagaggtcc    7080
gaaaataat aataatttag gtaaggggcg ttcaggcgga aggcctaaac caaaagttt    7140
tgatgaagtt gaaaagagt ttgataattt gattgaagat gaagccgaga cgtcggtcgc    7200
ggattctgat tcgtattaaa tatgtcttac tcaatcactt ctccatcgca atttgtgttt    7260
ttgtcatctg tatgggctga ccctatagaa ttgttaaacg tttgtacaaa ttcgttaggt    7320
aaccagtttc aaacacagca agcaagaact actgttcaac agcagttcag cgaggtgtgg    7380
aaaccttcc ctcagagcac cgtcagattt cctggcgatg tttataaggt gtacaggtac    7440
aatgcagttt tagatcctct aattactgcg ttgctggggg cttttgatac taggaataga    7500
ataatcgaag tagaaaacca gcagagtccg acaacagctg aaacgttaga tgctacccgc    7560
agggtagacg acgctacggt tgcaattcgg tctgctataa ataatttagt taatgaacta    7620
gtaagaggta ctggactgta caatcagaat acttttgaaa gtatgtctgg gttggtctgg    7680
acctctgcac ctgcatctta aatgcatagg tgctgaaata taaagtttgt gtttctaaaa    7740
cacacgtggt acgtacgata acgtacagtg ttttccctc cacttaaatc gaagggtagt    7800
gtcttggagc gcgcggagta acatatatg gttcatatat gtccgtaggc acgtaaaaaa    7860
agcgagggat tcgaattccc ccggaacccc cggttggggc ccaggtacca attcttgaag    7920
acgaagggc ctcgtgatac gcctattttt ataggttaat gtcatgataa taatggtttc    7980
ttagacgtca ggtggcactt ttcggggaaa tgtgcgcgga accctatttt gtttattttt    8040
ctaaatacat tcaaatatgt atccgctcat gagacaataa ccctgataaa tgcttcaata    8100
atattgaaaa aggaagagta tgagtattca acatttccgt gtcgccctta ttcccttttt    8160
tgcggcattt tgccttcctg tttttgctca cccagaaacg ctggtgaaag taaaagatgc    8220
tgaagatcag ttgggtgcac gagtgggtta catcgaactg gatctcaaca gcggtaagat    8280
ccttgagagt tttcgccccg aagaacgttt tccaatgatg agcactttta aagttctgct    8340
atgtggcgcg gtattatccc gtgttgacgc cgggcaagag caactcggtc gccgcataca    8400
ctattctcag aatgacttgg ttgagtactc accagtcaca gaaaagcatc ttacggatgg    8460
catgacagta agagaattat gcagtgctgc cataaccatg agtgataaca ctgcggccaa    8520
cttacttctg acaacgatcg gaggaccgaa ggagctaacc gcttttttgc acaacatggg    8580
ggatcatgta actcgccttg atcgttggga accggagctg aatgaagcca taccaaacga    8640
cgagcgtgac accacgatgc ctgcagcaat ggcaacaacg ttgcgcaaac tattaactgg    8700
cgaactactt actctagctt cccggcaaca attaatagac tggatggagg cggataaagt    8760
tgcaggacca cttctgcgct cggcccttcc ggctggctgg tttattgctg ataaatctgg    8820
agccggtgag cgtgggtctc gcggtatcat tgcagcactg gggccagatg gtaagccctc    8880
ccgtatcgta gttatctaca cgacggggag tcaggcaact atggatgaac gaaatagaca    8940
```

-continued

```
gatcgctgag ataggtgcct cactgattaa gcattggtaa ctgtcagacc aagtttactc    9000
atatatactt tagattgatt taaaacttca tttttaattt aaaaggatct aggtgaagat    9060
ccttttgat aatctcatga ccaaaatccc ttaacgtgag ttttcgttcc actgagcgtc    9120
agacccgta gaaaagatca aaggatcttc ttgagatcct ttttttctgc gcgtaatctg    9180
ctgcttgcaa acaaaaaaac caccgctacc agcggtggtt tgtttgccgg atcaagagct    9240
accaactctt tttccgaagg taactggctt cagcagagcg cagataccaa atactgtcct    9300
tctagtgtag ccgtagttag gccaccactt caagaactct gtagcaccgc ctacatacct    9360
cgctctgcta atcctgttac cagtggctgc tgccagtggc gataagtcgt gtcttaccgg    9420
gttggactca agacgatagt taccggataa ggcgcagcgg tcgggctgaa cggggggttc    9480
gtgcacacag cccagcttgg agcgaacgac ctacaccgaa ctgagatacc tacagcgtga    9540
gctatgagaa agcgccacgc ttcccgaagg gagaaaggcg acaggtatc cggtaagcgg    9600
cagggtcgga acaggagagc gcacgaggga gcttccaggg ggaaacgcct ggtatcttta    9660
tagtcctgtc gggtttcgcc acctctgact tgagcgtcga ttttgtgat gctcgtcagg    9720
ggggcggagc ctatggaaaa acgccagcaa cgcggccttt ttacgttcc tggccttttg    9780
ctggcctttt gctcacatgt tctttcctgc gttatcccct gattctgtgg ataaccgtat    9840
taccgccttt gagtgagctg ataccgctcg ccgcagccga acgaccgagc gcagcgagtc    9900
agtgagcgag gaagcggaag agcgcctgat gcggtatttt ctccttacgc atctgtgcgg    9960
tatttcacac cgcatatggt gcactctcag tacaatctgc tctgatgccg catagttaag   10020
ccagtataca ctccgctatc gctacgtgac tgggtcatgg ctgcgccccg acacccgcca   10080
acacccgctg acgcgccctg acgggcttgt ctgctcccgg catccgctta cagacaagct   10140
gtgaccgtct ccgggagctg catgtgtcag aggttttcac cgtcatcacc gaaacgcgcg   10200
aggcagctgc ggtaaagctc atcagcgtgg tcgtgaagcg attcacagat gtctgcctgt   10260
tcatccgcgt ccagctcgtt gagtttctcc agaagcgtta atgtctggct tctgataaag   10320
cgggccatgt taagggcggt ttttttcctgt ttggtcactt gatgcctccg tgtaaggggg   10380
aatttctgtt catgggggta atgataccga tgaaacgaga gaggatgctc acgatacggg   10440
ttactgatga tgaacatgcc cggttactgg aacgttgtga gggtaaacaa ctggcggtat   10500
ggatgcggcg ggaccagaga aaaatcactc agggtcaatg ccagcgcttc gttaatacag   10560
atgtaggtgt tccacagggt agccagcagc atcctgcgat gcagatccgg aacataatgg   10620
tgcagggcgc tgacttccgc gtttccagac tttacgaaac acggaaaccg aagaccattc   10680
atgttgttgc tcaggtcgca gacgttttgc agcagcagtc gcttcacgtt cgctcgcgta   10740
tcggtgattc attctgctaa ccagtaaggc aaccccgcca gcctagccgg gtcctcaacg   10800
acaggagcac gatcatgcgc acccgtggcc aggacccaac gctgcccgag atgcgccgcg   10860
tgcggctgct ggagatggcg gacgcgatgg atatgttctg ccaagggttg gtttgcgcat   10920
tcacagttct ccgcaagaat tgattggctc caattcttgg agtggtgaat ccgttagcga   10980
ggtgccgccg gcttccattc aggtcgaggt ggcccggctc catgcaccgc gacgcaacgc   11040
ggggaggcag acaaggtata gggcggcgcc tacaatccat gccaacccgt tccatgtgct   11100
cgccgaggcg gcataaatcg ccgtgacgat cagcggtcca gtgatcgaag ttaggctggt   11160
aagagccgcg agcgatcctt gaagctgtcc ctgatggtcg tcatctacct gcctggacag   11220
catggcctgc aacgcgggca tcccgatgcc gccggaagcg agaagaatca taatgggaa    11280
```

-continued

| | |
|---|---|
| ggccatccag cctcgcgtcg cgaacgccag caagacgtag cccagcgcgt cggccgccat | 11340 |
| gccggcgata atggcctgct tctcgccgaa acgtttggtg gcgggaccag tgacgaaggc | 11400 |
| ttgagcgagg gcgtgcaaga ttccgaatac cgcaagcgac aggccgatca tcgtcgcgct | 11460 |
| ccagcgaaag cggtcctcgc cgaaaatgac ccagagcgct gccggcacct gtcctacgag | 11520 |
| ttgcatgata agaagacag tcataagtgc ggcgacgata gtcatgcccc gcgcccaccg | 11580 |
| gaaggagctg actgggttga aggctctcaa gggcatcggt cgagatttag gtgacactat | 11640 |
| a | 11641 |

<210> SEQ ID NO 14
<211> LENGTH: 8234
<212> TYPE: DNA
<213> ORGANISM: Tobacco mosaic virus

<400> SEQUENCE: 14

| | |
|---|---|
| gtattttac aacaattacc aacaacaaca acaacagac aacattacaa ttactattta | 60 |
| caattacaat ggcatacaca cagacagcta ccacatcagc tttgctggac actgtccgag | 120 |
| gaaacaactc cttggtcaat gatctagcaa agcgtcgtct ttacgacaca gcggttgaag | 180 |
| agtttaacgc tcgtgaccgc aggcccaagg tgaacttttc aaaagtaata agcgaggagc | 240 |
| agacgcttat tgctacccgg gcgtatccag aattccaaat tacatttat aacacgcaaa | 300 |
| atgccgtgca ttcgcttgca ggtggattgc gatctttaga actggaatat ctgatgatgc | 360 |
| aaattcccta cggatcattg acttatgaca taggcgggaa ttttgcatcg catctgttca | 420 |
| agggacgagc atatgtacac tgctgcatgc ccaacctgga cgttcgagac atcatgcggc | 480 |
| acgaaggcca gaaagacagt attgaactat acctttctag gctagagaga gggggaaaa | 540 |
| cagtccccaa cttccaaaag gaagcatttg acagatacgc agaaattcct gaagacgctg | 600 |
| tctgtcacaa tactttccag acatgcgaac atcagccgat gcagcaatca ggcagagtgt | 660 |
| atgccattgc gctacacagc atatatgaca taccagccga tgagttcggg gcggcactct | 720 |
| tgaggaaaaa tgtccatacg tgctatgccg ctttccactt ctccgagaac ctgcttcttg | 780 |
| aagattcatg cgtcaatttg gacgaaatca acgcgtgttt ttcgcgcgat ggagacaagt | 840 |
| tgacctttc ttttgcatca gagagtactc ttaattactg tcatagttat tctaatattc | 900 |
| ttaagtatgt gtgcaaaact tacttcccgg cctctaatag agaggtttac atgaaggagt | 960 |
| ttttagtcac cagagttaat acctggtttt gtaagttttc tagaatagat acttttctt | 1020 |
| tgtacaaagg tgtgcccat aaaagtgtag atagtgagca gttttatact gcaatggaag | 1080 |
| acgcatggca ttacaaaag actcttgcaa tgtgcaacag cgagagaatc ctccttgggg | 1140 |
| attcatcatc agtcaattac tggtttccca aaatgagga tatggtcatc gtaccattat | 1200 |
| tcgacatttc tttggagact agtaagagga cgcgcaagga agtcttagtg tccaaggatt | 1260 |
| tcgtgttcac agtgcttaac cacattcgaa cataccaggc gaaagctctt acatacgcaa | 1320 |
| atgtttttgtc cttcgtcgaa tcgattcgat cgagggtaat cattaacggt gtgacagcga | 1380 |
| ggtccgaatg ggatgtggac aaatctttgt acaatccttg tccatgacg ttttacctgc | 1440 |
| atactaagct tgccgttcta aaggatgact tactgattag caagtttagt ctcggttcga | 1500 |
| aaacggtgtg ccagcatgtg tgggatgaga tttcgctggc gtttgggaac gcatttccct | 1560 |
| ccgtgaaaga gaggctcttg aacaggaaac ttatcagagt ggcaggcgac gcattagaga | 1620 |
| tcagggtgcc tgatctatat gtgaccttcc acgacagatt agtgactgag tacaaggcct | 1680 |
| ctgtggacat gcctgcgctt gacattagga agaagatgga agaaacggaa gtgatgtaca | 1740 |

-continued

```
atgcactttc agaattatcg gtgttaaggg agtctgacaa attcgatgtt gatgtttttt    1800
cccagatgtg ccaatctttg aagttgacc  caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc attggtagtt acctcaagag    1980
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag ggagtatcat gtggcgcttt    2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa acccttgcat ggcaagatcc    3120
tgacttttac ccaatcggat aaagaagctc tgctttcaag agggtattca gatgttcaca    3180
ctgtgcatga agtgcaaggc gagacatact ctgatgtttc actagttagg ttaaccccta    3240
caccggtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat ttcattgaat gtcaaagatt    3600
gcatattgga tatgtctaag tctgttgctg cacctaagga tcaaatcaaa ccactaatac    3660
ctatggtacg aacggcggca gaaatgccac gccagactgg actattggaa aatttagtgg    3720
cgatgattaa aagaaacttt aacgcacccg agttgtctgg catcattgat attgaaaata    3780
ctgcatcttt ggttgtagat aagtttttg  atagttattt gcttaaagaa aaaagaaaac    3840
caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca aacaaaagtt ggacacttca atccaaacgg    4020
agtacccggc tttgcagacg attgtgtacc attcaaaaaa gatcaatgca atattcggcc    4080
```

```
cgttgtttag tgagcttact aggcaattac tggacagtgt tgattcgagc agatttttgt    4140
ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattggtttt cgaagacttc ttgggagaag    4320
tttggaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaataat ggttcatgag    5040 aatgagtcat tgtcaggggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cattctcgga    5220
tcttactaca cagcagctgc aaagaaaaga tttcagttca aggtcgttcc caattatgct    5280
ataaccaccc aggacgcgat gagaaacgtc tggcaagttt tagttaatat tagaaatgtg    5340
aagatgtcag cgggtttctg tccgcttcct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtagtgatc ggtcagtgcc gaacaagaac tatagaaatg ttaaggattt tggaggaatg    5640
agttttaaaa agaataattt aatcgatgat gattcggagg ctactgtcgc cgaatcggat    5700 tcgtttttaaa tagatcttac agtatcacta ctccatctca gttcgtgttc ttgtcattaa    5760
ttaaaatgca gctgaggaac ccagaactac atctgggctg cgcgcttgcg cttcgcttcc    5820
tggccctcgt ttcctgggac atccctgggg ctagagcact ggacaatgga ttggcaagga    5880
cgcctaccat gggctggctg cactgggagc gcttcatgtg caaccttgac tgccaggaag    5940
agccagattc ctgcatcagt gagaagctct tcatggagat ggcagagctc atggtctcag    6000
aaggctggaa ggatgcaggt tatgagtacc tctgcattga tgactgttgg atggctcccc    6060
aaagagattc agaaggcaga cttcaggcag accctcagcg ctttcctcat gggattcgcc    6120
agctagctaa ttatgttcac agcaaaggac tgaagctagg gatttatgca gatgttggaa    6180
ataaaacctg cgcaggcttc cctgggagtt ttggatacta cgacattgat gcccagacct    6240
ttgctgactg gggagtagat ctgctaaaat ttgatggttg ttactgtgac agtttggaaa    6300
atttggcaga tggttataag cacatgtcct ggccctgaa taggactggc agaagcattg    6360
tgtactcctg tgagtggcct ctttatatgt ggcccttca aaagcccaat tatacagaaa    6420
tccgacagta ctgcaatcac tggcgaaatt ttgctgacat tgatgattcc tggaaaagta    6480
```

-continued

```
taaagagtat cttggactgg acatctttta accaggagag aattgttgat gttgctggac    6540 caggggttg gaatgaccca gatatgttag tgattggcaa ctttggcctc agctggaatc     6600
agcaagtaac tcagatggcc ctctgggcta tcatggctgc tcctttattc atgtctaatg    6660
acctccgaca catcagccct caagccaaag ctctccttca ggataaggac gtaattgcca    6720
tcaatcagga ccccttgggc aagcaagggt accagcttag acaggagac aactttgaag     6780 tgtgggaacg acctctctca ggcttagcct gggctgtagc tatgataaac cggcaggaga    6840
ttggtggacc tcgctcttat accatcgcag ttgcttccct gggtaaagga gtggcctgta    6900
atcctgcctg cttcatcaca cagctcctcc ctgtgaaaag gaagctaggg ttctatgaat    6960
ggacttcaag gttaagaagt cataaaatc ccacaggcac tgttttgctt cagctatctg     7020
aaaaggacga attatgacct aggggtagt caagatgcat aataaataac ggattgtgtc     7080
cgtaatcaca cgtggtgcgt acgataacgc atagtgtttt tccctccact taaatcgaag    7140
ggttgtgtct tggatcgcgc gggtcaaatg tatatggttc atatacatcc gcaggcacgt    7200
aataaagcga ggggtcggg tcgaggtcgg ctgtgaaact cgaaaaggtt ccggaaaaca     7260 aaaagagag tggtaggtaa tagtgttaat aataagaaaa taaataatag tggtaagaaa     7320
ggtttgaaag ttgaggaaat tgaggataat gtaagtgatg acgagtctat cgcgtcatcg    7380
agtacgtttt aatcaatatg ccttatacaa tcaactctcc gagccaattt gtttacttaa    7440
gttccgctta tgcagatcct gtgcagctga tcaatctgtg tacaaatgca ttgggtaacc    7500
agtttcaaac gcaacaagct aggacaacag tccaacagca atttgcggat gcctggaaac    7560
ctgtgcctag tatgacagtg agatttcctg catcggattt ctatgtgtat agatataatt    7620
cgacgcttga tccgttgatc acggcgttat taaatagctt cgatactaga aatagaataa    7680
tagaggttga taatcaaccc gcaccgaata ctactgaaat cgttaacgcg actcagaggg    7740
tagacgatgc gactgtagct ataagggctt caatcaataa tttggctaat gaactggttc    7800
gtggaactgg catgttcaat caagcaagct ttgagactgc tagtggactt gtctggacca    7860
caactccggc tacttagcta ttgttgtgag atttcctaaa ataaagtcac tgaagactta    7920
aaattcaggg tggctgatac caaaatcagc agtggttgtt cgtccactta aatataacga    7980
ttgtcatatc tggatccaac agttaaacca tgtgatggtg tatactgtgg tatggcgtaa    8040
aacaacggaa aagtcgctga agacttaaaa ttcagggtgg ctgataccaa aatcagcagt    8100
ggttgttcgt ccactaaaaa ataacgattg tcatatctgg atccaacagt taaaccatgt    8160
gatggtgtat actgtggtat ggcgtaaaac aacggagagg ttcgaatcct cccctaaccg    8220
cgggtagcgg ccca                                                      8234
```

<210> SEQ ID NO 15
<211> LENGTH: 11
<212> TYPE: PRT
<213> ORGANISM: Tobacco
<220> FEATURE:
<221> NAME/KEY: MISC_FEATURE
<222> LOCATION: (1)..(4)
<223> OTHER INFORMATION: Xaa = any

<400> SEQUENCE: 15

Xaa Xaa Pro Xaa Ile Pro Lys Ser Phe Gly Tyr
1               5                   10

<210> SEQ ID NO 16
<211> LENGTH: 11

```
<212> TYPE: PRT
<213> ORGANISM: Homo sapiens

<400> SEQUENCE: 16

Ala Arg Pro Cys Ile Pro Lys Ser Phe Gly Tyr
1               5                   10

<210> SEQ ID NO 17
<211> LENGTH: 8
<212> TYPE: DNA
<213> ORGANISM: Tobacco mosaic virus

<400> SEQUENCE: 17 gagggtat                                                                    8

<210> SEQ ID NO 18
<211> LENGTH: 6
<212> TYPE: PRT
<213> ORGANISM: plant

<400> SEQUENCE: 18

Ser Glu Lys Asp Glu Leu
1               5
```